US011559587B2

(12) United States Patent
Sahin et al.

(10) Patent No.: US 11,559,587 B2
(45) Date of Patent: Jan. 24, 2023

(54) RNA FORMULATION FOR IMMUNOTHERAPY

(71) Applicants: BioNTech SE, Mainz (DE); TRON—Translationale Onkologie an der Universitätsmedizin der Johannes Gutenberg—Universität Mainz gGmbH, Mainz (DE)

(72) Inventors: Ugur Sahin, Mainz (DE); Heinrich Haas, Mainz (DE); Sebastian Kreiter, Mainz (DE); Mustafa Diken, Mainz (DE); Daniel Fritz, Mainz (DE); Martin Meng, Mainz (DE); Lena Mareen Kranz, Mainz (DE); Kerstin Reuter, Darmstadt (DE)

(73) Assignees: TRON-Translationale Onkologie an der Universitätsmedizin der Johannes Gutenberg-Universität Mainz gGmbH, Mainz (DE); BioNTech SE, Mainz (DE)

( * ) Notice: Subject to any disclaimer, the term of this patent is extended or adjusted under 35 U.S.C. 154(b) by 382 days.

(21) Appl. No.: 16/578,601

(22) Filed: Sep. 23, 2019

(65) Prior Publication Data

US 2020/0085974 A1    Mar. 19, 2020

Related U.S. Application Data

(60) Division of application No. 14/388,192, filed as application No. PCT/EP2013/000902 on Mar. 25, 2013, now Pat. No. 10,485,884, which is a continuation-in-part of application No. PCT/EP2012/001319, filed on Mar. 26, 2012.

(51) Int. Cl.
  *A61K 48/00* (2006.01)
  *A61K 39/00* (2006.01)
  *A61K 9/127* (2006.01)

(52) U.S. Cl.
  CPC ........ *A61K 48/0033* (2013.01); *A61K 9/1272* (2013.01); *A61K 39/0011* (2013.01); *A61K 48/0025* (2013.01); *A61K 2039/53* (2013.01); *A61K 2039/55555* (2013.01)

(58) Field of Classification Search
  CPC ...... A61K 2039/53; A61K 2039/55555; A61K 39/0011; A61K 48/0025; A61K 48/0033; A61K 9/1272; A61P 31/00; A61P 35/00
  USPC .................. 424/277.1, 450, 489, 490, 93.21
  See application file for complete search history.

(56) References Cited

U.S. PATENT DOCUMENTS

| 4,897,355 A | 1/1990 | Eppstein et al. |
|---|---|---|
| 5,264,618 A | 11/1993 | Felgner et al. |
| 5,580,859 A | 12/1996 | Feigner et al. |
| 5,703,055 A | 12/1997 | Felgner et al. |
| 6,251,399 B1 | 6/2001 | Diamond et al. |
| 6,472,176 B2 | 10/2002 | Kovesdi et al. |
| 6,500,641 B1 | 12/2002 | Chen et al. |
| 6,586,410 B1 | 7/2003 | Wheeler et al. |
| 7,303,881 B2 | 12/2007 | Huang et al. |
| 7,462,354 B2 | 12/2008 | Sette et al. |
| 7,790,696 B2 | 9/2010 | Gregoriadis |
| 8,140,270 B2 | 3/2012 | Kingsmore et al. |
| 8,217,016 B2 | 7/2012 | Hoerr et al. |
| 8,349,558 B2 | 1/2013 | Fatho et al. |
| 8,703,142 B2 | 4/2014 | Diamond et al. |
| 8,853,283 B2 | 10/2014 | Platscher et al. |
| 8,877,206 B2 | 11/2014 | Chen et al. |
| 9,115,402 B2 | 8/2015 | Hacohen et al. |
| 10,485,884 B2 | 11/2019 | Sahin et al. |
| 2007/0025968 A1 | 2/2007 | Van Der Burg et al. |
| 2009/0055944 A1 | 2/2009 | Korman et al. |
| 2009/0217401 A1 | 8/2009 | Korman et al. |
| 2011/0092574 A1* | 4/2011 | Kowalska .............. C12N 15/67 435/68.1 |
| 2011/0300205 A1 | 12/2011 | Geall et al. |
| 2011/0311584 A1 | 12/2011 | Sahin et al. |
| 2012/0237975 A1 | 9/2012 | Schrum et al. |
| 2013/0115272 A1 | 5/2013 | de Fougerolles et al. |
| 2013/0123481 A1 | 5/2013 | de Fougerolles et al. |
| 2013/0156849 A1 | 6/2013 | de Fougerolles et al. |
| 2013/0203115 A1 | 8/2013 | Schrum et al. |
| 2013/0237593 A1 | 9/2013 | de Fougerolles et al. |
| 2013/0237594 A1 | 9/2013 | de Fougerolles et al. |
| 2013/0244278 A1 | 9/2013 | de Fougerolles et al. |

(Continued)

FOREIGN PATENT DOCUMENTS

| CN | 102133404 A | 7/2011 |
|---|---|---|
| EP | 0839912 A1 | 5/1998 |

(Continued)

OTHER PUBLICATIONS

Pilla, L. et al. "Multipeptide vaccination in cancer patients" Expert Opinion on Biological Therapy, 9: 1043-1055, 2009.
Pleasance, E. et al. "A comprehensive catalogue of somatic mutaitons from a human cancer genome." Nature, 463:191-196, 2010.
Pleasance, E. et al. "A small-cell lung cancer genome with complex signatures of tobacco exposure." Nature, 463:184-190, 2010.
Rammensee (2006). "Some considerations on the use of peptides and mRNA for therapeutic vaccination against cancer," Immunol Cell Biol. 84(3):290-4.
Rammensee 2008, Chapter 50: Cancer Vaccines: Some Basic Considerations, Genomic and Personalized Medicine, Hungtington and Ginsburg. E-published on Nov. 11, 2008.

(Continued)

*Primary Examiner* — Janet L Epps -Smith
(74) *Attorney, Agent, or Firm* — Choate, Hall & Stewart LLP; Brenda Herschbach Jarrell; Michael A. Shinall

(57) ABSTRACT

The present invention is in the field of immunotherapy, in particular tumor immunotherapy. The present invention provides pharmaceutical formulations for delivering RNA to antigen presenting cells such as dendrite cells (DCs) in the spleen after systemic administration. In particular, the formulations described herein enable to induce an immune response after systemic administration of antigen-coding RNA.

44 Claims, 38 Drawing Sheets

(56) References Cited

U.S. PATENT DOCUMENTS

Figure 1:
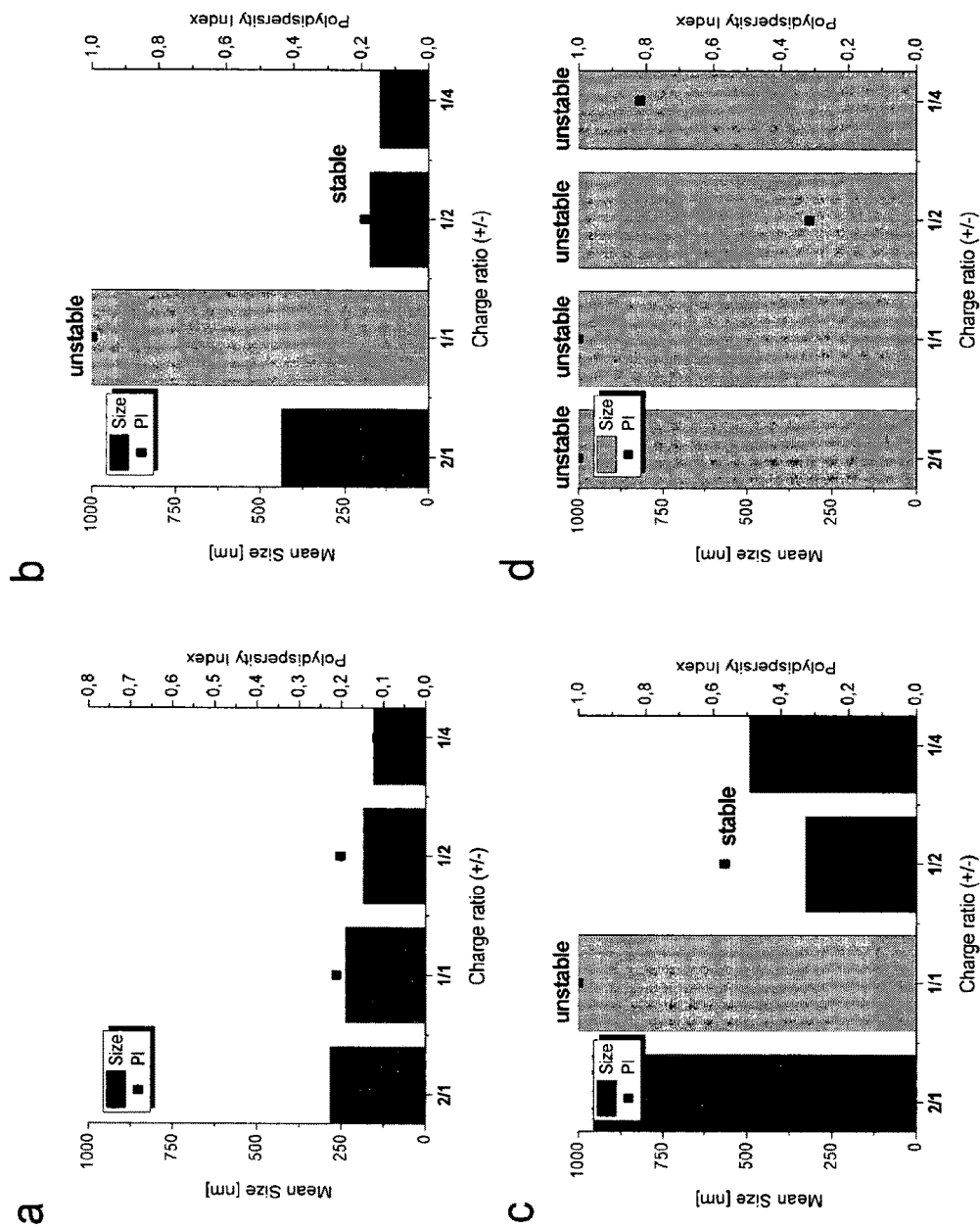

| | | |
|---|---|---|
| 2013/0244279 A1 | 9/2013 | de Fougerolles et al. |
| 2013/0245106 A1 | 9/2013 | de Fougerolles et al. |
| 2013/0245107 A1 | 9/2013 | de Fougerolles et al. |
| 2013/0255281 A1 | 10/2013 | Bray |
| 2013/0266640 A1 | 10/2013 | de Fougerolles et al. |
| 2014/0004199 A1 | 1/2014 | Xiao |
| 2014/0010861 A1 | 1/2014 | Bancel et al. |
| 2014/0147454 A1 | 5/2014 | Chakraborty et al. |
| 2014/0212498 A1 | 7/2014 | Brito et al. |
| 2015/0017211 A1 | 1/2015 | de Fougerolles et al. |
| 2015/0030576 A1 | 1/2015 | Bancel |
| 2015/0167017 A1 | 6/2015 | Roy et al. |

FOREIGN PATENT DOCUMENTS

| | | |
|---|---|---|
| EP | 1242108 A1 | 9/2002 |
| EP | 2569633 A2 | 3/2013 |
| EP | 2830593 A1 | 2/2015 |
| JP | H11-504631 A | 4/1999 |
| JP | H11504631 A | 4/1999 |
| JP | H11-510046 A | 9/1999 |
| JP | H11510046 A | 9/1999 |
| JP | 2010059064 A | 3/2010 |
| WO | 1994023031 A1 | 10/1994 |
| WO | 199634109 A1 | 10/1996 |
| WO | WO-96/34109 A1 | 10/1996 |
| WO | 199703703 A1 | 2/1997 |
| WO | WO-97/03703 A1 | 2/1997 |
| WO | 1998014464 A1 | 4/1998 |
| WO | 1999024566 A1 | 5/1999 |
| WO | 1999052503 A2 | 10/1999 |
| WO | 2000/20029 A1 | 4/2000 |
| WO | 2000067761 A1 | 11/2000 |
| WO | 2001047959 A2 | 7/2001 |
| WO | 2001093902 A2 | 12/2001 |
| WO | 2002048377 A2 | 6/2002 |
| WO | 2002083714 A2 | 10/2002 |
| WO | 02/098443 A2 | 12/2002 |
| WO | 2003051401 A2 | 6/2003 |
| WO | 2003068257 A1 | 8/2003 |
| WO | 2003106692 A2 | 12/2003 |
| WO | 2004004743 A1 | 1/2004 |
| WO | 2005030250 A2 | 4/2005 |
| WO | 2005039533 A1 | 5/2005 |
| WO | 2005040816 A1 | 5/2005 |
| WO | 2005110338 A2 | 11/2005 |
| WO | 2006121168 A1 | 11/2006 |
| WO | 2007024708 A2 | 3/2007 |
| WO | 2007025760 A2 | 3/2007 |
| WO | 2007031222 A2 | 3/2007 |
| WO | 2007101227 A2 | 9/2007 |
| WO | 2008080468 A1 | 7/2008 |
| WO | 2008083174 A2 | 7/2008 |
| WO | 2008085562 A2 | 7/2008 |
| WO | 08093195 A2 | 8/2008 |
| WO | 2008096321 A1 | 8/2008 |
| WO | WO 2008096321 A1 * | 8/2008 |
| WO | 2008116078 A2 | 9/2008 |
| WO | 2008156712 A1 | 12/2008 |
| WO | 2009053041 A2 | 4/2009 |
| WO | 2009118296 A2 | 10/2009 |
| WO | 2009129227 A1 | 10/2009 |
| WO | 2010014895 A2 | 2/2010 |
| WO | 2010037539 A1 | 4/2010 |
| WO | 2010066418 A1 | 6/2010 |
| WO | 11005799 A2 | 1/2011 |
| WO | 2011012316 A2 | 2/2011 |
| WO | WO-2011/127255 A1 | 10/2011 |
| WO | 2011/143656 A2 | 11/2011 |
| WO | 12006378 A1 | 1/2012 |
| WO | 2012045075 A1 | 4/2012 |
| WO | 2012045082 A2 | 4/2012 |
| WO | 2012135805 A2 | 10/2012 |
| WO | 2012159729 A1 | 11/2012 |
| WO | 2013006825 A1 | 1/2013 |
| WO | 2013040142 A2 | 3/2013 |
| WO | 2013052523 A1 | 4/2013 |
| WO | 2013090648 A1 | 6/2013 |
| WO | 2013113502 A1 | 8/2013 |
| WO | 2013124701 A2 | 8/2013 |
| WO | WO 2013113502 A1 * | 8/2013 |
| WO | 2013151663 A1 | 10/2013 |
| WO | 2013151664 A1 | 10/2013 |
| WO | 2013151665 A2 | 10/2013 |
| WO | 2013151672 A2 | 10/2013 |
| WO | 2014012051 A1 | 1/2014 |
| WO | 2014071219 A1 | 5/2014 |
| WO | 2014093924 A1 | 6/2014 |
| WO | 2014144039 A1 | 9/2014 |
| WO | 2014144711 A1 | 9/2014 |
| WO | 2014144767 A1 | 9/2014 |
| WO | 2014152027 A1 | 9/2014 |
| WO | 2014152030 A1 | 9/2014 |
| WO | 2014152031 A1 | 9/2014 |
| WO | 2014152211 A1 | 9/2014 |
| WO | 2014159813 A1 | 10/2014 |
| WO | 2014160243 A1 | 10/2014 |
| WO | 2014164253 A1 | 10/2014 |
| WO | 2014168874 A2 | 10/2014 |
| WO | 2015014375 A1 | 2/2015 |
| WO | 2015034925 A1 | 3/2015 |
| WO | 2015034928 A1 | 3/2015 |
| WO | 2015038892 A1 | 3/2015 |
| WO | 2015043613 A1 | 4/2015 |
| WO | 2015051169 A2 | 4/2015 |
| WO | 2015051173 A2 | 4/2015 |
| WO | 2015058780 A1 | 4/2015 |
| WO | 2015085318 A2 | 6/2015 |
| WO | 2015089511 A2 | 6/2015 |
| WO | 2015117620 A1 | 8/2015 |
| WO | 2015164674 A1 | 10/2015 |
| WO | 2015172843 A1 | 11/2015 |
| WO | 2016062323 A1 | 4/2016 |
| WO | 2016/091391 A1 | 6/2016 |
| WO | 2016107877 A1 | 7/2016 |
| WO | 2016155809 A1 | 10/2016 |

OTHER PUBLICATIONS

Rammensee et al. (2002). "Toward patient-specific tumor antigen selection for vaccination," Immunol. Rev. 188:164-176.

Rammensee et al., Immunogenentics, 50 (1999), 213-219.

Rao (1994). "Epitope-based vaccines: One step at a time," Proc. Indian natn. Sci. Acad. B60: 419-424.

Ressing, M. et al. "Human CTL epitopes encoded by human papillomavirus types 16E6 . . . " J. Immunol. 154:5934-5943, 1995.

Saenz-Badillos et al. (2001). "RNA as a tumor vaccine: a review of the literature," Exp Dermatol. 10(3):143-54.

Segal et al. (2008). "Epitope landscape in breast and colorectal cancer," Cancer Res. 68: 889-892.

Sensi and Aanichini, Unique Tumor Antigens: Evidence for Immune Control of Genome Integrity and Immunogenic Targets for T cell-mediated Patient-Specific Immunotherapy, Clin. Cancer Res. 2006:12(17), 5023.

Sette, A. et al. "Peptide Binding to the Most Frequent HLA-A Class I Alleles Measured by Quantitative Molecular Binding Assays" Mol Immunol. 31: 813-822, 1994.

Sette, A. et al. "The Relationship Between Class I Binding Affinity and Immunogenicity of Potential Cytotoxic T cell Epitopes." J. Immunol. 153: 5586-5592, 1994.

Shah et al. (2009). "Mutation of FOXL2 in granulosa-cell tumors of the ovary," N. Eng. J. Med. 360: 2719-2729.

Sjöblom et al. (2006). "The consensus coding sequences of human breast and colorectal cancers," Science 314: 268-274.

Stephens et al. (2005). "A screen of the complete protein kinase gene family identifies diverse patterns of somatic mutations in human breast cancer," Nature Genetics, 37: 590-592.

Thomson et al., J. Virology (1998), 72(3):2246-2252.

Toes et al. (1997). "Protective anti-tumor immunity induced by vaccination with recombinant adenoviruses encoding multiple tumor-

(56) References Cited

OTHER PUBLICATIONS associated cytotoxic T lymphocyte epitopes in a string-of-beads fashion," Proc. Natl. Acad. Sci. USA 94:14660-14665.
UniProtKB, "Print-outs from the UniProtKB database concerning the CEP170, PARVA and FLT3 genes".
van der Bruggen et al. (1991). "A gene encoding an antigen recognized by cytolytic T lymphocytes on a human melanoma," Science 254: 1643-1647.
Van Laere AS, Nguyen M, Braunschweig M. et al. A regulatory mutation in IGF2 causes a major QTL effect on muscle growth in the pig. Nature. 2003;425(6960):832-836.
Weinschenk et al. (2002). "Integrated functional genomics approach for the design of patient-individual antitumor vaccines," Cancer Res 62: 5818-5827.
Wolff et al. (1990). "Direct gene transfer into mouse muscle in vivo," Science 247: 1465-1468.
Wood et al. (2007). "The genomic landscapes of human breast and colorectal cancers," Science 318: 1108-1113.
Wortzel et al. (1983). "Multiple tumour-specific antigens expressed on a single tumour cell," Nature 304: 165-167.
Zhou et al., Hum. Gene Ther., 10(16):2719-24, 1999.
Provisional application U.S. Appl. No. 61/334,866, filed May 14, 2010.
Japanese Notice of Reasons for Rejection issued in related Japanese Application No. 2017-219079, dated Aug. 6, 2018.
Canadian Office Action issued in related Canadian Application No. 2,864,253 dated Aug. 28, 2018.
Kranz et al. "Systemic RNA delivery to dendritic cells exploits antiviral defence for cancer immunotherapy" Nature, 2016.
Extended data figure 1 of Kranz et al.
Sep. 10, 2019—(IN) Office Action—App 6907/CHENP/2014.
Miartinon et al., "Induction of virus-specific cytotoxic T lymphocytes in vivo by liposome-entrapped mRNA", European Journal of Immunology, 1993, 23(1), 1719-1722.
Yadava et al., "Effect of Lyophilization and Freeze-thawing on the Stability of siRNA-liposome Complexes", AAPS Pharmscitech, 2008, 9(2), 335-341.
International Preliminary Report of Patentability Chapter I, dated Oct. 1, 2014, 2012, Filed in relation to PCT Application No. PCT/EP2012/001319, Filed Mar. 26, 2012, Entitled "RNA formulation for immunotherapy," By applicant "BioNTech AG," 9 pages.
International Search Report (ISR), dated Mar. 7, 2013, Filed in relation to PCT Application No. PCT/EP2012/001319, Filed Mar. 26, 2012, Entitled "RNA formulation for immunotherapy," By applicant "BioNTech AG," 4 pages.
Written Opinion of the International Search Authority, dated Mar. 7, 2013, Filed in relation to PCT Application No. PCT/EP2012/001319, Filed Mar. 26, 2012, Entitled RNA formulation for immunotherapy, By applicant "BioNTech AG," 8 pages.
International Preliminary Report of Patentability Chapter I, dated Oct. 1, 2014, Filed in relation to PCT Application No. PCT/EP2013/000902, Filed Mar. 25, 2013, Entitled "RNA formulation for immunotherapy," By applicant "BioNTech AG," 10 pages.
International Search Report (ISR), dated Jun. 17, 2013, Filed in relation to PCT Application No. PCT/EP2013/000902, Filed Mar. 25, 2013, Entitled "RNA formulation for immunotherapy," By applicant "BioNTech AG," 4 pages.
Written Opinion of the International Search Authority, dated Jun. 17, 2013, Filed in relation to PCT Application No. PCT/EP2013/000902, Filed Mar. 25, 2013, Entitled "RNA formulation for immunotherapy," By applicant "BioNTech AG," 9 pages.
Markov et al., "Novel cationic liposomes provide highly efficient delivery of DNA and RNA into dendritic cell progenitors and their immature offsets," Journal of Controlled Release, 160 (2012) 200-210.
Office Action dated Oct. 30, 2017 in related European Application No. 13713356.7.
Agrawal et al., Trend in Biotechnology, 14(10): 376-387, 1996.
Mayer et al., Anticancer Research 25:3917-3924 (2005).
Bei et al.J Immunother. May 1998;21(3):159-69.

Boczkowski et al. (1996). "Dendritic cells pulsed with RNA are potent antigen-presenting cells in vitro and in vivo," J. Exp. Med. 184: 465-472.
Bowerman, NA. "Engineering the binding properties of the T cell receptor: peptide: MHC ternary complex that governs T cell activity." Mol. Immun. 46: 3000-3008, 2009.
Brickner et al. J. Exp. Med 193(2) 195-205 (2001).
Del Val et al., Cell, vol. 66, Issue 6, Sep. 20, 1991, pp. 1145-1153.
Conry et al. (1994). "Immune response to a carcinoembryonic antigen polynucleotide vaccine," Cancer Res. 54: 1164-1168.
Conry et al. (1995). "Characterization of a messenger RNA polynucleotide vaccine vector," Cancer Res. 55: 1397-1400.
Coulie et al. (1995). "A mutated intron sequence codes for an antigenic peptide recognized by cytolytic T lymphocytes on a human melanoma," Proc. Natl. Acad. Sci. USA 92: 7976-7980.
Dengjel, J. et al. "Glycan side chains on naturally presented MHC class II ligands" J. Mass Spectrom, 2005.
Ding et al. "Genome remodeling in a basal-like breast cancer metastatis and xenograft." Nature, 464: 999-1005, 2010.
Dolgin, "The Billion-Dollar Biotech," Nature, vol. 522, pp. 26-28, Jun. 4, 2015.
Fritsch, E. F. et al. "HLA-Binding Properties of Tumor Neoepitopes in Humans" Cancer Immunology Research, 2: 522-529, 2014.
Gnirke, A. "Solution hybrid selection with ultra-long oligonucleotides for massively parallel targeted sequencing" Nat. Biotechnol, 2009.
Goya, R. et al. "SNVMix: predicting single nucleotide variants from next-generation sequencing of tumors, Bioinformatics" Bioinformatics, 26: 730-736, 2010.
Gryaznov et al., Biochim. Biophys. Acta, 1489: 131-140, 1999.
Guyre et al., Cancer Immunother (1997) 45:146-148.
Hacohen Decl. dated Feb. 16, 2014 filed in U.S. Appl. No. 13/108,610, 10 pages.
Hoerr et al. (2000). "In vivo application of RNA leads to induction of specific cytotoxic T lymphocytes and antibodies," Eur. J. Immunol. 30: 1-7.
Johanning et al. Nucleic Acids Res. May 11, 1995; 23(9): 1495-1501.
Kenter, G. G. et al. "Phase I Immunotherapeutic Trial with Long Peptides Spanning the E6 and E7 sequences of High-risk human papillomavirus 16 in End-stage cervical cancer patients shows low toxicity and robust immunogenicity." Clinical Cancer Research, 14: 169-177, 2008.
Keogh, E. et al. "Identification of New Epitopes from Four Different Tumor-Associated Antigens: Recognition of Naturally Processed Epitopes Correlates with HLA-A*0201-Binding Affinity" J. Immunol. 167: 787-796, 2001.
Lemmel, Claudia et al., "Differential quantitative analysis of MHC ligands by mass spectrometry using stable isotope labeling" Nat Biotechnol, 2004.
Lennerz et al. (2005). "The response of autologous T cells to a human melanoma is dominated by mutated neoantigens," Proc. Natl. Acad. Sci. USA 102: 16013-16018.
Ley et al. (2008). "DNA sequencing of a cytogenetically normal acute myeloid leukaemia genome," Nature 456: 66-72.
Li et al., Cancer Genome Sequencing and Its Implications for Personalized Cancer Vaccine, Cancers 2011, 3, 4191-4211.
Maksyutov and Zagrebelnaya (1993). "ADEPT: a computer program for prediction of protein antigenic determinants," Comput. Appl. Biosci. 9: 291-297.
Mandelboim et al. (1995). "Regression of established murine carcinoma metastases following vaccination with tumour-associated antigen peptides," Nature Medicine 1: 1179-1183.
Mardis, ER. "Recurring Mutations Found by Seuencing an Acute Myeloid Leukemia Genome" New England J. Med. 361: 1058-1066, 2009.
Margulies, Marcel et al., "Genome Sequencing in Open Microfabricated High Density Picoliter Reactors" Nature, 2005.
Martinon et al. (1993). Induction of virus-specific cytotoxic T lymphocytes in vivo by liposome-entrapped mRNA. Eur. J. Immunol 23, 1719-1722.

(56) References Cited

OTHER PUBLICATIONS

Meyerson, M. et al. "Advances in understanding cancer genomes through second-generation sequencing" Nature Rev. Genetics. 11:685-695, 2010.

Monach et al. (1995). "A unique tumor antigen produced by a single amino acid substitution," Immunity 2: 45-59.

Mortazavi (2008). "Mapping and quantifying mammalian transcriptomes by RNA-Seq," Nature Methods 5: 621-628.

Parker et al., J. Immunol. 152 (1994), 163-175.

Parkhurst, MR. et al. "Improved Induction of Melanoma-reactive CTL with peptides from the melanoma antigen gp100 modified at HLA-A*0201-binding residues" J. Immunol. 157: 2549-2548, 1996.

Parmiani, G. et al. "Unique Human Tumor Antigens: Immunobiology and Use in Clinical Trials." The Journal of Immunology, 178: 1975-1979, 2007.

Perissi et al., Electron Spin Resonance and Differential Scanning Calorimetry as Combined Tools for the Study of Liposomes in the Presence of Long Chain Nitroxides, 106 J. of Phys. Chem. B 10468 (2002).

Pfohl et al., Biological Polyelectrolyte Complexes in Solution and Confined on Patterned Surfaces, 198-200 Colloids & Surfaces A: Physicochemical and Eng. Aspects 613 (2002).

Liu, J. et al., Electrostatically Mediated Liposome Fusion and Lipid Exchange with a Nanoparticle-Supported Bilayer for Control of Surface Charge, Drug Containment, and Delivery, J. Am. Chem. Soc., 131:7567-7569 (2009).

\* cited by examiner a)

b)

Lipo:RNA 1:1

RNA FORMULATION FOR IMMUNOTHERAPY

TECHNICAL FIELD OF THE INVENTION

The present invention is in the field of immunotherapy, in particular tumor immunotherapy. The present invention relates to the provision of pharmaceutical formulations for delivering RNA with high selectivity to antigen presenting cells such as dendritic cells (DCs) in the spleen after systemic administration. In particular, the formulations described herein enable to induce an immune response after systemic administration of antigen-coding RNA.

BACKGROUND OF THE INVENTION

Nucleic acids like DNA, siRNA or RNA are of interest for various therapeutic interventions in patients. A relatively new immunological approach in tumor therapy is based on tumor antigen expression by coding RNA in antigen presenting cells (APCs) in order to induce a T-cell response to the tumor (Weide, B. et al. (2008) *Journal of Immunotherapy* 31(2): 180-188; Weide, B. et al. (2009) *Journal of Immunotherapy* 32(5): 498-507; Kreiter, S. et al. (2010) *Cancer Res* 70(22): 9031-9040; Kuhn, A. N. et al. (2010) *Gene Ther* 17(8): 961-971). Target cells for such intervention are dendritic cells (DCs) which reside, for example, in the lymph nodes (LNs) or in the spleen.

In order to provide sufficient uptake of the RNA by DCs, local administration of RNA to lymph nodes has proven to be successful. However, such local administration requires specific skills by the physician. Therefore, there is a need for RNA formulations which can be administered systemically, for example intravenously (i.v.), subcutaneously (s.c.), intradermally (i.d.) or by inhalation. From the literature, various approaches for systemic administration of nucleic acids are known. In non-viral gene transfer, cationic liposomes are used to induce DNA/RNA condensation and to facilitate cellular uptake. The cationic liposomes usually consist of a cationic lipid, like DOTAP, and one or more helper lipids, like DOPE. So-called lipoplexes' can be formed from the cationic (positively charged) liposomes and the anionic (negatively charged) nucleic acid. In the simplest case, the lipoplexes form spontaneously by mixing the nucleic acid with the liposomes with a certain mixing protocol, however various other protocols may be applied. Electrostatic interactions between the positively charged liposomes and the negatively charged nucleic acid are the driving force for the lipoplex formation. Besides the lipid composition, the charge ratio between cationic and anionic moieties plays a key role for efficient condensation and transfection. Generally, an excess positive charge of the lipoplexes is considered necessary for efficient transfection (Templeton, N. S. et al. (1997) *Nature Biotechnology* 15(7): 647-652; Zhdanov, R. I. et al. (2002) *Bioelectrochemistry* 58(1): 53-64; Templeton, N. S. (2003) *Current Medicinal Chemistry* 10(14): 1279-1287). Most natural membranes are negatively charged, and therefore the attractive electrostatic interaction between the positively charged lipoplexes and the negatively charged biomembrane may play a role in cell binding and uptake of the lipoplexes. Typical ranges of +/− ratios which are considered optimal for transfection are between 2 and 4. With lower excess positive charge, the transfection efficacy goes drastically down to virtually zero. Unfortunately, for positively charged liposomes and lipoplexes elevated toxicity has been reported, which can be a problem for the application of such preparations as pharmaceutical products.

The above described lipoplexes have proven to enable transfection in various organs. The detailed organ distribution of expression depends on the formulation and administration parameters (lipid composition, size, administration route) in a complex manner. So far, selective expression in a given target organ or cellular moiety, avoiding expression in off-target organs, could not be realized sufficiently. Using luciferase DNA or RNA as a reporter, for example, transfection in lung, liver, spleen, kidneys, and heart has been reported. Avoiding targeting of lung and liver has proven to be particularly difficult, because, in many cases, lung and liver targeting are predominant. Lung has a very large surface and it is the first organ which the i.v. injected compounds pass after administration. Liver is a typical target organ for liposomes and formulations with lipophilic compounds like the lipids present in the lipoplexes.

For RNA based immunotherapy, lung or liver targeting can be detrimental, because of the risk of an immune response against these organs. Therefore, for such therapy, a formulation with high selectivity only for the DCs, such as in the spleen is required. Certain ligands have been proposed to improve targeting selectivity. For example, liposomes which comprise mannose functionalized lipids are considered to improve macrophage targeting. However, such components make the formulations more complex, which makes practical pharmaceutical development more complicated. Furthermore, the selectivity is limited and a certain fraction of the liposomes is still taken up by other organs. Another problem is serum interactions and RNA degradation in serum, which is favored by positively charged lipoplexes. Also, for therapeutic applicability, requirements for pharmaceutical products such as chemical and physical stability, need to be fulfilled. In addition, products for intraperitoneal application need to be sterile and have to fulfill certain requirements regarding particle characteristics. Additionally, the products have to be suitable for manufacturing.

Summarizing, the problem of development of an injectable RNA formulation with high spleen selectivity, which fulfills the criteria for products for application to patients, still needs to be solved.

The present invention provides a solution to the above described problem. According to the invention, nanoparticulate RNA formulations with defined particle size are provided wherein the net charge of the particles is close to zero or negative. In one particularly preferred embodiment, said RNA nanoparticles are RNA lipoplexes. Surprisingly it was found that electro-neutral or negatively charged lipoplexes from RNA and liposomes lead to substantial RNA expression in spleen DCs after systemic administration. A strong expression of reporter gene in the target cells (spleen) was determined while the expression in other organs was low. Furthermore, a strong immune response against a model antigen could be induced. This was unexpected, because usually, excess positive charge is considered a prerequisite for successful uptake and expression. Here we have found that, although the absolute amount of expression decreases with decreasing excess of positive charge, the expression is still sufficiently high to provide therapeutic efficacy of the lipoplexes after systemic administration.

According to the invention it was possible to form the lipoplexes with a well-defined particle size distribution profile as measured by dynamic light scattering and with low fraction of subvisible particles, which is required for intravenous administration to patients. If formed by incubation of liposomes with RNA by self-assembly, the particle size of the original liposomes is only little affected, and no undesired moieties of large aggregates are found. Different sizes can be obtained by selecting the size of the precursor liposomes and the mixing conditions. This was surprising because usually formation of large aggregates on incubation of RNA with cationic liposomes is observed. This aggregate formation is one major obstacle for developing lipoplex formulations which are acceptable for intravenous or subcutaneous administration. The particles were stable for at least 24 hours and did not tend to aggregate over time. The particles could be frozen and thawed without formation of aggregates, while maintaining the original particle size profile, and maintaining the biological activity. The particles could be lyophilized and reconstituted with water without formation of aggregates, while maintaining the original particle size profile and maintaining the biological activity. The particles can be manufactured by different protocols which are scalable and which can be performed under controlled conditions. With such properties the lipoplex formulations of the invention fulfill important requirements for pharmaceutical formulations for application to patients, in terms of particle size distribution profile and stability. Furthermore, compared to positively charged lipopexes, the RNA nanoparticles described herein are expected to be less toxic and to display less undesired serum interactions. In particular, the formulations are suitable for parenteral administration, including intravenous and subcutaneous administration.

DESCRIPTION OF INVENTION

Summary of the Invention

Immunotherapeutic strategies are promising options for the treatment of e.g. infectious diseases and cancer diseases. The identification of a growing number of pathogen- and tumor-associated antigens (also termed tumor antigens herein) led to a broad collection of suitable targets for immunotherapy.

The present invention generally embraces the immunotherapeutic treatment of diseases by targeting diseased cells. The invention provides for the selective eradication of cells that express an antigen thereby minimizing adverse effects to normal cells not expressing said antigens. Thus, preferred diseases for a therapy are those in which one or more antigens are expressed such as cancer diseases or infectious diseases.

The present invention aims at specifically targeting antigen-expressing cells by active immunization inducing and expanding T cells in the patient, which are able to specifically recognize and kill diseased cells. Specifically, the present invention enables selective incorporation of an antigen represented as RNA into antigen-presenting cells such as dendritic cells in vivo. The antigen may be processed to produce a peptide partner for the MHC molecule or may be presented without the need for further processing, if it can bind to MHC molecules. Preference is given to administration forms in which the complete antigen is processed in vivo by antigen-presenting cells, since this may also produce T helper cell responses which are needed for an effective immune response. Thus, the compositions provided according to the invention when administered to a patent provide one or more MHC presented epitopes for stimulating, priming and/or expanding T cells directed against cells expressing antigens from which the MHC presented epitopes are derived. Accordingly, the compositions described herein are preferably capable of inducing or promoting a cellular response, preferably cytotoxic T cell activity, against a disease characterized by presentation of antigens with class I MHC.

In particular, the present invention relates to a pharmaceutical composition comprising nanoparticles which comprise RNA encoding at least one antigen, wherein:

(i) the number of positive charges in the nanoparticles does not exceed the number of negative charges in the nanoparticles and/or (ii) the nanoparticles have a neutral or net negative charge and/or (iii) the charge ratio of positive charges to negative charges in the nanoparticles is 1.4:1 or less and/or (iv) the zeta potential of the nanoparticles is 0 or less.

Preferably, the nanoparticles described herein are colloidally stable for at least 2 hours in the sense that no aggregation, precipitation or increase of size and polydispersity index by more than 30% as measured by dynamic light scattering takes place In one embodiment, the charge ratio of positive charges to negative charges in the nanoparticles is between 1.4:1 and 1:8, preferably between 1.2:1 and 1:4, e.g. between 1:1 and 1:3 such as between 1:1.2 and 1:2, 1:1.2 and 1:1.8, 1:1.3 and 1:1.7, in particular between 1:1.4 and 1:1.6, such as about 1:1.5.

In one embodiment, the zeta potential of the nanoparticles is −5 or less, −10 or less, −15 or less, −20 or less or −25 or less. In various embodiments, the zeta potential of the nanoparticles is −35 or higher, −30 or higher or −25 or higher. In one embodiment, the nanoparticles have a zeta potential from 0 mV to −50 mV, preferably 0 mV to −40 mV or −10 mV to −30 mV.

In one embodiment, the nanoparticles comprise at least one lipid. In one embodiment, the nanoparticles comprise at least one cationic lipid. The cationic lipid can be monocationic or polycationic. Any cationic amphiphilic molecule, eg, a molecule which comprises at least one hydrophilic and lipophilic moiety is a cationic lipid within the meaning of the present invention. In one embodiment, the positive charges are contributed by the at least one cationic lipid and the negative charges are contributed by the RNA. In one embodiment, the nanoparticles comprises at least one helper lipid. The helper lipid may be a neutral or an anionic lipid. The helper lipid may be a natural lipid, such as a phospholipid or an analogue of a natural lipid, or a fully synthetic lipid, or lipid-like molecule, with no similarities with natural lipids. In one embodiment, the cationic lipid and/or the helper lipid is a bilayer forming lipid.

In one embodiment, the at least one cationic lipid comprises 1,2-di-O-octadecenyl-3-trimethylammonium propane (DOTMA) or analogs or derivatives thereof and/or 1,2-dioleoyl-3-trimethylammonium-propane (DOTAP) or analogs or derivatives thereof.

In one embodiment, the at least one helper lipid comprises 1,2-di-(9Z-octadecenoyl)-sn-glycero-3-phosphoethanolamine (DOPE) or analogs or derivatives thereof, cholesterol (Chol) or analogs or derivatives thereof and/or 1,2-dioleoyl-sn-glycero-3-phosphocholine (DOPC) or analogs or derivatives thereof.

In one embodiment, the molar ratio of the at least one cationic lipid to the at least one helper lipid is from 10:0 to 3:7, preferably 9:1 to 3:7, 4:1 to 1:2, 4:1 to 2:3, 7:3 to 1:1, or 2:1 to 1:1, preferably about 1:1. In one embodiment, in this ratio, the molar amount of the cationic lipid results from the molar amount of the cationic lipid multiplied by the number of positive charges in the cationic lipid.

In various embodiments, the lipids are not functionalized such as functionalized by mannose, histidine and/or imidazole, the nanoparticles do not comprise a targeting ligand such as mannose functionalized lipids and/or the nanoparticles do not comprise one or more of the following: pH dependent compounds, cationic polymers such as polymers containing histidine and/or polylysine, wherein the polymers may optionally be PEGylated and/or histidylated, or divalent ions such as $Ca^{2+}$.

In various embodiments, the RNA nanoparticles may comprise peptides, preferentially with a molecular weight of up to 2500 Da.

In the nanoparticles described herein the lipid may form a complex with and/or may encapsulate the RNA. In one embodiment, the nanoparticles comprise a lipoplex or liposome. In one embodiment, the lipid is comprised in a vesicle encapsulating said RNA. The vesicle may be a multilamellar vesicle, an unilamellar vesicle, or a mixture thereof. The vesicle may be a liposome.

In one embodiment, the nanoparticles are lipoplexes comprising DOTMA and DOPE in a molar ratio of 10:0 to 1:9, preferably 8:2 to 3:7, and more preferably of 7:3 to 5:5 and wherein the charge ratio of positive charges in DOTMA to negative charges in the RNA is 1.8:2 to 0.8:2, more preferably 1.6:2 to 1:2, even more preferably 1.4:2 to 1.1:2 and even more preferably about 1.2:2.

In one embodiment, the nanoparticles are lipoplexes comprising DOTMA and Cholesterol in a molar ratio of 10:0 to 1:9, preferably 8:2 to 3:7, and more preferably of 7:3 to 5:5 and wherein the charge ratio of positive charges in DOTMA to negative charges in the RNA is 1.8:2 to 0.8:2, more preferably 1.6:2 to 1:2, even more preferably 1.4:2 to 1.1:2 and even more preferably about 1.2:2.

In one embodiment, the nanoparticles are lipoplexes comprising DOTAP and DOPE in a molar ratio of 10:0 to 1:9, preferably 8:2 to 3:7, and more preferably of 7:3 to 5:5 and wherein the charge ratio of positive charges in DOTMA to negative charges in the RNA is 1.8:2 to 0.8:2, more preferably 1.6:2 to 1:2, even more preferably 1.4:2 to 1.1:2 and even more preferably about 1.2:2.

In one embodiment, the nanoparticles are lipoplexes comprising DOTMA and DOPE in a molar ratio of 2:1 to 1:2, preferably 2:1 to 1:1, and wherein the charge ratio of positive charges in DOTMA to negative charges in the RNA is 1.4:1 or less.

In one embodiment, the nanoparticles are lipoplexes comprising DOTMA and cholesterol in a molar ratio of 2:1 to 1:2, preferably 2:1 to 1:1, and wherein the charge ratio of positive charges in DOTMA to negative charges in the RNA is 1.4:1 or less.

In one embodiment, the nanoparticles are lipoplexes comprising DOTAP and DOPE in a molar ratio of 2:1 to 1:2, preferably 2:1 to 1:1, and wherein the charge ratio of positive charges in DOTAP to negative charges in the RNA is 1.4:1 or less.

In one embodiment, the nanoparticles have an average diameter in the range of from about 50 nm to about 1000 nm, preferably from about 50 nm to about 400 nm, preferably about 100 nm to about 300 nm such as about 150 nm to about 200 nm. In one embodiment, the nanoparticles have a diameter in the range of about 200 to about 700 nm, about 200 to about 600 nm, preferably about 250 to about 550 nm, in particular about 300 to about 500 nm or about 200 to about 400 nm.

In one embodiment, the polydispersity index of the nanoparticles described herein as measured by dynamic light scattering is 0.5 or less, preferably 0.4 or less or even more preferably 0.3 or less.

In one embodiment, the nanoparticles described herein are obtainable by one or more of the following: (i) incubation of liposomes in an aqueous phase with the RNA in an aqueous phase, (ii) incubation of the lipid dissolved in an organic, water miscible solvent, such as ethanol, with the RNA in aqueous solution, (iii) reverse phase evaporation technique, (iv) freezing and thawing of the product, (v) dehydration and rehydration of the product, (vi) lyophilization and rehydration of the of the product, or (vii) spray drying and rehydration of the product.

In one embodiment, the nanoparticles are produced by a process comprising a step of incubating the RNA with bivalent cations preferably at a concentration of between 0.1 mM to 5 mM such as 0.1 mM to 4 mM or 0.3 mM to 1 mM prior to incorporation into said nanoparticles and/or by incubating the RNA with monovalent ions preferably at a concentration of between 1 mM to 500 mM such as 100 mM to 200 mM or 130 mM to 170 mM prior to incorporation into said nanoparticles and/or by incubating the RNA with buffers prior to incorporation into said nanoparticles.

In one embodiment, after incubation of the bivalent cations to RNA a step of dilution by adding liposomes and/or other aqueous phases by at least a factor of more than 1.5, preferably by a factor of more than 2, or by a factor of more than 5 is involved.

In one embodiment, the bivalent cations are calcium ions, where the final concentration of said calcium ions is less than 4 mM, preferably less than 3 mM and even more preferably 2.2 mM or less.

In one embodiment, the nanoparticles described herein are produced by a process comprising a step of extruding and/or a step of filtration and/or a step of lyophilizing the nanoparticles.

In one embodiment, after systemic administration of the nanoparticles, RNA expression in the spleen occurs. In one embodiment, after systemic administration of the nanoparticles, no or essentially no RNA expression in the lung and/or liver occurs. In one embodiment, after systemic administration of the nanoparticles, RNA expression in the spleen is at least 5-fold, preferably at least 8-fold, preferably at least 10-fold, preferably at least 20-fold, preferably at least 50-fold, preferably at least 100-fold, preferably at least 1000-fold or even more the amount of RNA expression in the lung. In one embodiment, after systemic administration of the nanoparticles, RNA expression in antigen presenting cells, preferably professional antigen presenting cells in the spleen occurs.

In one embodiment, the nanoparticles when administered systemically target or accumulate in the spleen. Preferably, the nanoparticles when administered systemically deliver the RNA to antigen presenting cells, preferably professional antigen presenting cells such as dendritic cells and/or macrophages in the spleen. Preferably the nanoparticles release the RNA at the target organ or tissue and/or enter cells at the target organ or tissue. Preferably, the target organ or tissue is spleen and the cells at the target organ or tissue are antigen presenting cells such as dendritic cells. In one embodiment, the nanoparticles when administered systemically do not or do not essentially target or accumulate in the lung and/or liver. In one embodiment, the amount of the nanoparticles targeting or accumulating in the spleen is at least 5-fold, preferably at least 8-fold, preferably at least 10-fold, preferably at least 20-fold, preferably at least 50-fold, preferably at least 100-fold, preferably at least 1000-fold or even more the amount targeting or accumulating in the lung.

According to the invention, systemic administration is preferably by parenteral administration, preferably by intravenous administration, subcutaneous administration, intradermal administration or intraarterial administration.

The antigen encoded by the RNA comprised in the nanoparticles described herein preferably is a disease-associated antigen or elicts an immune response against a disease-associated antigen or cells expressing a disease-associated antigen.

The pharmaceutical composition of the invention may further comprise one or more pharmaceutically acceptable carriers, diluents and/or excipients. The pharmaceutical composition of the invention may further comprise at least one adjuvant.

The pharmaceutical composition of the invention may be formulated for systemic administration.

The pharmaceutical composition of the invention may be used for inducing an immune response, in particular an immune response against a disease-associated antigen or cells expressing a disease-associated antigen, such as an immune response against cancer. Accordingly, the pharmaceutical composition may be used for prophylactic and/or therapeutic treatment of a disease involving a disease-associated antigen or cells expressing a disease-associated antigen, such as cancer. Preferably said immune response is a T cell response. In one embodiment, the disease-associated antigen is a tumor antigen.

In one embodiment, the RNA comprised in the nanoparticles described herein does not comprise pseudouridine residues and preferably does not comprise modified nucleosides.

The present invention also relates to a method for delivering an antigen to antigen presenting cells, preferably professional antigen presenting cells such as dendritic cells and/or macrophages in the spleen or expressing an antigen in antigen presenting cells, preferably professional antigen presenting cells such as dendritic cells and/or macrophages in the spleen comprising administering to a subject a pharmaceutical composition of the invention.

The present invention also relates to a method for inducing an immune response, preferably an immune response against cancer, in a subject comprising administering to the subject a pharmaceutical composition of the invention.

The present invention also relates to a method for stimulating, priming and/or expanding T cells in a subject comprising administering to the subject a pharmaceutical composition of the invention.

The present invention also relates to a method of treating or preventing a disease involving an antigen, preferably a cancer disease, in a subject comprising administering to the subject a pharmaceutical composition of the invention.

In the above aspects, the disease may be tumor growth and/or tumor metastasis. Accordingly, the present invention also relates to a method of treating or preventing tumor growth and/or tumor metastasis in a subject that has or is at risk of developing tumors and/or tumor metastases comprising administering to the subject a pharmaceutical composition of the invention.

In one aspect, the invention also provides the agents and compositions described herein for use in the methods of treatment described herein.

The present invention also relates to particles as set forth herein.

The present invention also relates to a method for producing RNA-containing nanoparticles comprising the steps of: (a) providing RNA formulated in sodium chloride solution and (b) adding liposomes to the RNA. The sodium chloride solution may be an aqueous solution. Water may be used for preparing the sodium chloride solution and in one embodiment may be the only solvent used. In one embodiment, the sodium chloride solution contains about 50 to about 300 mM, preferably about 100 to about 200 mM, preferably about 150 mM sodium chloride. In one embodiment, the sodium chloride solution is an isotonic sodium chloride solution. The liposomes may be formulated in water. In one embodiment, the liposomes are added to the RNA by injection of the liposomes into the RNA formulation. The nanoparticles produced according to the above method may be nanoparticles as set forth herein.

Other features and advantages of the instant invention will be apparent from the following detailed description and claims.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., (1995) Helvetica Chimica Acta, CH-4010 Basel, Switzerland.

The practice of the present invention will employ, unless otherwise indicated, conventional methods of biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The present invention describes agents and compositions that upon administration induce an immune response, in particular a cellular immune response, directed against a disease-associated antigen or cells expressing a disease-associated antigen such as cancer cells. In particular, the present invention envisions the use of RNA encoding antigenic proteins or peptides (also termed "antigen" herein) inducing an immune response, in particular a T cell response, against the disease-associated antigen or cells expressing the disease-associated antigen. These antigenic proteins or peptides may comprise a sequence essentially corresponding to or being identical to the sequence of the disease-associated antigen or one or more fragments thereof. In one embodiment, the antigenic protein or peptide comprises the sequence of an MHC presented peptide derived from the disease-associated antigen. Immunisation with RNA encoding intact or substantially intact disease-associated antigen or fragments thereof such as MHC class I and class II peptides makes it possible to elicit a MHC class I and/or a class II type response and thus, stimulate T cells such as CD8+ cytotoxic T lymphocytes which are capable of lysing diseased cells and/or CD4+ T cells. Such immunization may also elicit a humoral immune response (B cell response) resulting in the production of antibodies against the antigen. Accordingly, the pharmaceutical composition of the present invention may be used in genetic vaccination, wherein an immune response is stimulated by introduction into a subject a suitable RNA molecule which codes for an antigenic protein or peptide. The agents and compositions disclosed herein may be used as a therapeutic or prophylactic vaccine for the treatment or prevention of a disease such as a disease as disclosed herein. In one embodiment, a disease-associated antigen is a tumor antigen. In this embodiment, the agents and compositions described herein may be useful in treating cancer or cancer metastasis. Preferably, the diseased organ or tissue is characterized by diseased cells such as cancer cells expressing a disease-associated antigen and preferably presenting the disease-associated antigen in the context of MHC molecules.

The term "immune response" refers to an integrated bodily response to an antigen or a cell expressing an antigen and preferably refers to a cellular immune response or a cellular as well as a humoral immune response. The immune response may be protective/preventive/prophylactic and/or therapeutic.

"Inducing an immune response" may mean that there was no immune response against a particular antigen or a cell expressing an antigen before induction, but it may also mean that there was a certain level of immune response against a particular antigen or a cell expressing an antigen before induction and after induction said immune response is enhanced. Thus, "inducing an immune response" also includes "enhancing an immune response". Preferably, after inducing an immune response in a subject, said subject is protected from developing a disease such as an infectious disease or a cancer disease or the disease condition is ameliorated by inducing an immune response. For example, an immune response against a viral antigen may be induced in a patient having a viral disease or in a subject being at risk of developing a viral disease. For example, an immune response against a tumor antigen may be induced in a patient having a cancer disease or in a subject being at risk of developing a cancer disease. Inducing an immune response in this case may mean that the disease condition of the subject is ameliorated, that the subject does not develop metastases, or that the subject being at risk of developing a cancer disease does not develop a cancer disease.

A "cellular immune response", a "cellular response", a "cellular response against an antigen" or a similar term is meant to include a cellular response directed to cells expressing an antigen and being characterized by presentation of an antigen with class I or class II MHC. The cellular response relates to cells called T cells or T lymphocytes which act as either "helpers" or "killers". The helper T cells (also termed CD4$^+$ T cells) play a central role by regulating the immune response and the killer cells (also termed cytotoxic T cells, cytolytic T cells, CD8$^+$ T cells or CTLs) kill diseased cells such as infected cells or cancer cells, preventing the production of more diseased cells. In preferred embodiments, the present invention involves the stimulation of an anti-tumor CTL response against cancer cells expressing one or more tumor antigens and preferably presenting such tumor antigens with class I MHC.

According to the present invention, the term "antigen" comprises any molecule, preferably a peptide or protein, which comprises at least one epitope that will elicit an immune response and/or against which an immune response is directed. Preferably, an antigen in the context of the present invention is a molecule which, optionally after processing, induces an immune response, which is preferably specific for the antigen or cells expressing the antigen. In particular, an "antigen" relates to a molecule which, optionally after processing, is presented by MHC molecules and reacts specifically with T lymphocytes (T cells).

Thus, an antigen or fragments thereof should be recognizable by a T cell receptor. Preferably, the antigen or fragment if recognized by a T cell receptor is able to induce in the presence of appropriate co-stimulatory signals, clonal expansion of the T cell carrying the T cell receptor specifically recognizing the antigen or fragment. In the context of the embodiments of the present invention, the antigen or fragment is preferably presented by a cell, preferably by an antigen presenting cell and/or a diseased cell, in the context of MHC molecules, which results in an immune response against the antigen or cells expressing the antigen.

According to the present invention, any suitable antigen is envisioned which is a candidate for an immune response, wherein the immune response is preferably a cellular immune response.

An antigen is preferably a product which corresponds to or is derived from a naturally occurring antigen. Such naturally occurring antigens may include or may be derived from allergens, viruses, bacteria, fungi, parasites and other infectious agents and pathogens or an antigen may also be a tumor antigen. According to the present invention, an antigen may correspond to a naturally occurring product, for example, a viral protein, or a part thereof.

The term "pathogen" relates to pathogenic microorganisms and comprises viruses, bacteria, fungi, unicellular organisms, and parasites. Examples for pathogenic viruses are human immunodeficiency virus (HIV), cytomegalovirus (CMV), herpes virus (HSV), hepatitis A-virus (HAV), HBV, HCV, papilloma virus, and human T-lymphotrophic virus (HTLV). Unicellular organisms comprise plasmodia, trypanosomes, amoeba, etc.

The term "disease-associated antigen" refers to all antigens that are of pathological significance and includes "tumor antigens". According to the invention it is desired to induce an immune response to a disease-associated antigen or cells expressing a disease-associated antigen and preferably presenting a disease-associated antigen in the context of MHC molecules. Preferably, a disease-associated antigen is a naturally occurring antigen. In one embodiment, a disease-associated antigen is expressed in a diseased cell and preferably presented by MHC molecules of the cell.

An antigen encoded by the RNA comprised in the nanoparticles described herein should induce an immune response which is directed against the disease-associated antigen to be targeted or cells expressing the disease-associated antigen to be targeted. Thus, an antigen encoded by the RNA comprised in the nanoparticles described herein may correspond to or may comprise a disease-associated antigen or one or more immunogenic fragments thereof such as one or more MHC binding peptides of the disease-associated antigen. Thus, the antigen encoded by the RNA comprised in the nanoparticles described herein may be a recombinant antigen.

The term "recombinant" in the context of the present invention means "made through genetic engineering". Preferably, a "recombinant object" such as a recombinant nucleic acid in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

In a preferred embodiment, an antigen may be a tumor antigen, i.e., a constituent of cancer cells such as a protein or peptide expressed in a cancer cell which may be derived from the cytoplasm, the cell surface or the cell nucleus, in particular those which primarily occur intracellularly or as surface antigens on cancer cells. For example, tumor antigens include the carcinoembryonal antigen, α1-fetoprotein, isoferritin, and fetal sulphoglycoprotein, α2-H-ferroprotein and γ-fetoprotein. According to the present invention, a tumor antigen preferably comprises any antigen which is expressed in and optionally characteristic with respect to type and/or expression level for tumors or cancers as well as for tumor or cancer cells. In the context of the present invention, the term "tumor antigen" or "tumor-associated antigen" preferably relates to proteins that are under normal conditions specifically expressed in a limited number of tissues and/or organs or in specific developmental stages, for example, the tumor antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2 or 1. The tumor antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor antigen is preferably not or only rarely expressed in normal tissues. Preferably, the tumor antigen or the aberrant expression of the tumor antigen identifies cancer cells. In the context of the present invention, the tumor antigen that is expressed by a cancer cell in a subject, e.g., a patient suffering from a cancer disease, is preferably a self-protein in said subject. In preferred embodiments, the tumor antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, the amino acid sequence of the tumor antigen is identical between the tumor antigen which is expressed in normal tissues and the tumor antigen which is expressed in cancer tissues. Preferably, a tumor antigen is presented by a cancer cell in which it is expressed.

Examples for tumor antigens that may be useful in the present invention are p53, ART-4, BAGE, beta-catenin/m, Bcr-abL CAMEL, CAP-1, CASP-8, CDC27/m, CDK4/m, CEA, the cell surface proteins of the claudin family, such as CLAUDIN-6, CLAUDIN-18.2 and CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Pml/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT, preferably WT-1.

The term "epitope" refers to an antigenic determinant in a molecule such as an antigen, i.e., to a part in or fragment of the molecule that is recognized by the immune system, for example, that is recognized by a T cell, in particular when presented in the context of MHC molecules. An epitope of a protein such as a tumor antigen preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 9, 10, 11, 12, 13, 14, 15, 16, 17, 18, 19, 20, 21, 22, 23, 24, or 25 amino acids in length. It is particularly preferred that the epitope in the context of the present invention is a T cell epitope.

According to the invention an epitope may bind to MHC molecules such as MHC molecules on the surface of a cell and thus, may be a "MHC binding peptide". The term "MHC binding peptide" relates to a peptide which binds to an MHC class I and/or an MHC class II molecule. In the case of class I MHC/peptide complexes, the binding peptides are typically 8-10 amino acids long although longer or shorter peptides may be effective. In the case of class II MHC/peptide complexes, the binding peptides are typically 10-25 amino acids long and are in particular 13-18 amino acids long, whereas longer and shorter peptides may be effective.

According to the invention, an antigen encoded by the RNA comprised in the nanoparticles described herein may comprise an immunogenic fragment of a disease-associated antigen such as a peptide fragment of a disease-associated antigen (also termed antigen peptide herein) which preferably is a MHC binding peptide.

An "immunogenic fragment of an antigen" according to the invention preferably relates to a portion or fragment of an antigen which is capable of stimulating an immune response, preferably a cellular response against the antigen or cells expressing the antigen and preferably presenting the antigen such as diseased cells, in particular cancer cells. Preferably, an immunogenic fragment of an antigen is capable of stimulating a cellular response against a cell characterized by presentation of an antigen with class I MHC and preferably is capable of stimulating an antigen-responsive CTL. Preferably, it is a portion of an antigen that is recognized (i.e., specifically bound) by a T cell receptor, in particular if presented in the context of MHC molecules. Certain preferred immunogenic fragments bind to an MHC class I or class II molecule. As used herein, an immunogenic fragment is said to "bind to" an MHC class I or class II molecule if such binding is detectable using any assay known in the art.

Preferably, an immunogenic fragment of an antigen according to the invention is an MHC class I and/or class II presented peptide or can be processed to produce a MHC class I and/or class II presented peptide. Preferably, an immunogenic fragment of an antigen comprises an amino acid sequence substantially corresponding and preferably being identical to the amino acid sequence of a fragment of the antigen. Preferably, said fragment of an antigen is an MHC class I and/or class II presented peptide.

If a peptide is to be presented directly, i.e., without processing, in particular without cleavage, it has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length.

If a peptide is part of a larger entity comprising additional sequences, e.g. of a polypeptide, and is to be presented following processing, in particular following cleavage, the peptide produced by processing has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length. Preferably, the sequence of the peptide which is to be presented following processing is derived from the amino acid sequence of an antigen, i.e., its sequence substantially corresponds and is preferably completely identical to a fragment of an antigen.

Thus, an antigen encoded by the RNA comprised in the nanoparticles described herein may comprise a sequence of 7-20 amino acids in length, more preferably 7-12 amino acids in length, more preferably 8-11 amino acids in length, in particular 9 or 10 amino acids in length which substantially corresponds and is preferably completely identical to a MHC presented fragment of a disease-associated antigen and following processing makes up a presented peptide.

Peptides having amino acid sequences substantially corresponding to a sequence of a peptide which is presented by the class I MHC may differ at one or more residues that are not essential for TCR recognition of the peptide as presented by the class I MHC, or for peptide binding to MHC. Such substantially corresponding peptides are also capable of stimulating CTL having the desired specificity and may be considered immunologically equivalent.

A peptide when presented by MHC should be recognizable by a T cell receptor. Preferably, the presented peptide if recognized by a T cell receptor is able to induce in the presence of appropriate co-stimulatory signals, clonal expansion of the T cell carrying the T cell receptor specifically recognizing the presented peptide. Preferably, antigen peptides, in particular if presented in the context of MHC molecules, are capable of stimulating an immune response, preferably a cellular response against the antigen from which they are derived or cells expressing the antigen and preferably presenting the antigen. Preferably, an antigen peptide is capable of stimulating a cellular response against a cell presenting the antigen with class I MHC and preferably is capable of stimulating an antigen-responsive CTL. Such cell preferably is a target cell for the purposes of the invention.

"Target cell" shall mean a cell which is a target for an immune response such as a cellular immune response. Target cells include cells that express an antigen such as a disease-associated antigen and preferably present said antigen (which, in particular, means that the antigen is processed in the cells and one or more fragments of the antigen are presented in the context of MHC molecules on the cells). Target cells include any undesirable cell such as an infected cell or cancer cell. In preferred embodiments, the target cell is a cell expressing an antigen as described herein and preferably presenting said antigen with class I MHC.

"Antigen processing" refers to the degradation of an antigen into procession products, which are fragments of said antigen (e.g., the degradation of a protein into peptides) and the association of one or more of these fragments (e.g., via binding) with MHC molecules for presentation by cells, preferably antigen presenting cells to specific T cells.

An antigen-presenting cell (APC) is a cell that presents, i.e. displays, antigen in the context of major histocompatibility complex (MHC) on its surface. This, includes the situation where only one or more fragments of an antigen are presented. T cells may recognize this complex using their T cell receptor (TCR). Antigen-presenting cells process antigens and present them to T cells.

Professional antigen-presenting cells are very efficient at internalizing antigen, either by phagocytosis or by receptor-mediated endocytosis, and then displaying a fragment of the antigen, bound to a class II MHC molecule, on their membrane. The T cell recognizes and interacts with the antigen-class II MHC molecule complex on the membrane of the antigen-presenting cell. An additional co-stimulatory signal is then produced by the antigen-presenting cell, leading to activation of the T cell. The expression of co-stimulatory molecules is a defining feature of professional antigen-presenting cells.

The main types of professional antigen-presenting cells are dendritic cells, which have the broadest range of antigen presentation, and are probably the most important antigen-presenting cells, macrophages, B-cells, and certain activated epithelial cells.

Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of antitumoral immunity.

Dendritic cells are conveniently categorized as "immature" and "mature" cells, which can be used as a simple way to discriminate between two well characterized phenotypes. However, this nomenclature should not be construed to exclude all possible intermediate stages of differentiation.

Immature dendritic cells are characterized as antigen presenting cells with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g. CD54 and CD11) and costimulatory molecules (e.g., CD40, CD80, CD86 and 4-1 BB).

Dendritic cell maturation is referred to as the status of dendritic cell activation at which such antigen-presenting dendritic cells lead to T cell priming, while presentation by immature dendritic cells results in tolerance. Dendritic cell maturation is chiefly caused by biomolecules with microbial features detected by innate receptors (bacterial DNA, viral RNA, endotoxin, etc.), pro-inflammatory cytokines (TNF, IL-1, IFNs), ligation of CD40 on the dendritic cell surface by CD40L, and substances released from cells undergoing stressful cell death. The dendritic cells can be derived by culturing bone marrow cells in vitro with cytokines, such as granulocyte-macrophage colony-stimulating factor (GM-CSF) and tumor necrosis factor alpha.

Non-professional antigen-presenting cells do not constitutively express the MHC class II proteins required for interaction with naive T cells; these are expressed only upon stimulation of the non-professional antigen-presenting cells by certain cytokines such as IFNγ.

Antigen presenting cells can be loaded with MHC presented peptides by transducing the cells with nucleic acid, such as RNA, encoding a peptide or protein comprising the peptide to be presented, e.g. a nucleic acid encoding the antigen. Transfection of dendritic cells with mRNA is a promising antigen-loading technique of stimulating strong antitumor immunity.

The term "immunogenicity" relates to the relative efficiency of an antigen to induce an immune reaction.

The terms "T cell" and "T lymphocyte" are used interchangeably herein and include T helper cells (CD4+ T cells) and cytotoxic T cells (CTLs, CD8+ T cells) which comprise cytolytic T cells.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptors (TCR). The thymus is the principal organ responsible for the maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4+ T cells because they express the CD4 protein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy diseased cells, e.g. infected cells such as virally infected cells and cancer cells, and are also implicated in transplant rejection. These cells are also known as CD8+ T cells since they express the CD8 glycoprotein at their surface. These cells recognize their targets by binding to antigen associated with MHC class I, which is present on the surface of nearly every cell of the body.

A majority of T cells have a T cell receptor (TCR) existing as a complex of several proteins. The actual T cell receptor is composed of two separate peptide chains, which are produced from the independent T cell receptor alpha and beta (TCRα and TCRβ) genes and are called α- and β-TCR chains. γδ T cells (gamma delta T cells) represent a small subset of T cells that possess a distinct T cell receptor (TCR) on their surface. However, in γδ T cells, the TCR is made up of one γ-chain and one δ-chain. This group of T cells is much less common (2% of total T cells) than the αβ T cells.

All T cells originate from hematopoietic stem cells in the bone marrow. Hematopoietic progenitors derived from hematopoietic stem cells populate the thymus and expand by cell division to generate a large population of immature thymocytes. The earliest thymocytes express neither CD4 nor CD8, and are therefore classed as double-negative (CD4−CD8−) cells. As they progress through their development they become double-positive thymocytes (CD4+CD8+), and finally mature to single-positive (CD4+CD8− or CD4−CD8+) thymocytes that are then released from the thymus to peripheral tissues.

The first signal in activation of T cells is provided by binding of the T cell receptor to a short peptide presented by the major histocompatibility complex (MHC) on another cell. This ensures that only a T cell with a TCR specific to that peptide is activated. The partner cell is usually a professional antigen presenting cell (APC), usually a dendritic cell in the case of naïve responses, although B cells and macrophages can be important APCs. The peptides presented to CD8+ T cells by MHC class I molecules are 8-10 amino acids in length; the peptides presented to CD4+ T cells by MHC class II molecules are longer, as the ends of the binding cleft of the MHC class II molecule are open.

The term "clonal expansion" refers to a process wherein a specific entity is multiplied. In the context of the present invention, the term is preferably used in the context of an immunological response in which lymphocytes are stimulated by an antigen, proliferate, and the specific lymphocyte recognizing said antigen is amplified. Preferably, clonal expansion leads to differentiation of the lymphocytes.

According to the invention, cytotoxic T lymphocytes may be generated in vivo by incorporation of an antigen or an antigen peptide into antigen-presenting cells in vivo. The antigen or antigen peptide is represented as RNA. The antigen may be processed to produce a peptide partner for the MHC molecule, while a fragment thereof may be presented without the need for further processing. The latter is the case in particular, if these can bind to MHC molecules. The resulting cells present the complex of interest and are recognized by autologous cytotoxic T lymphocytes which then propagate.

Specific activation of CD4+ or CD8+ T cells may be detected in a variety of ways. Methods for detecting specific T cell activation include detecting the proliferation of T cells, the production of cytokines (e.g., lymphokines), or the generation of cytolytic activity. For CD4+ T cells, a preferred method for detecting specific T cell activation is the detection of the proliferation of T cells. For CD8+ T cells, a preferred method for detecting specific T cell activation is the detection of the generation of cytolytic activity.

The term "major histocompatibility complex" and the abbreviation "MHC" include MHC class I and MHC class II molecules and relate to a complex of genes which occurs in all vertebrates. MHC proteins or molecules are important for signaling between lymphocytes and antigen presenting cells or diseased cells in immune reactions, wherein the MHC proteins or molecules bind peptides and present them for recognition by T cell receptors. The proteins encoded by the MHC are expressed on the surface of cells, and display both self antigens (peptide fragments from the cell itself) and nonself antigens (e.g., fragments of invading microorganisms) to a T cell.

The MHC region is divided into three subgroups, class I, class II, and class III. MHC class I proteins contain an α-chain and β2-microglobulin (not part of the MHC encoded by chromosome 15). They present antigen fragments to cytotoxic T cells. On most immune system cells, specifically on antigen-presenting cells, MHC class II proteins contain α- and β-chains and they present antigen fragments to T-helper cells. MHC class III region encodes for other immune components, such as complement components and some that encode cytokines.

In humans, genes in the MHC region that encode antigen-presenting proteins on the cell surface are referred to as human leukocyte antigen (HLA) genes. However the abbreviation MHC is often used to refer to HLA gene products. HLA genes include the nine so-called classical MHC genes: HLA-A, HLA-B, HLA-C, HLA-DPA1, HLA-DPB1, HLA-DQA1, HLA-DQB1, HLA-DRA, and HLA-DRB1.

In one preferred embodiment of all aspects of the invention an MHC molecule is an HLA molecule.

By "cell characterized by presentation of an antigen", "cell presenting an antigen", "antigen presented by a cell", "antigen presented" or similar expressions is meant a cell, in particular a diseased cell or target cell such as an infected cell or a cancer cell, or an antigen presenting cell presenting the antigen it expresses or a fragment derived from said antigen, e.g. by processing of the antigen, in the context of MHC molecules, in particular MHC Class I molecules. Similarly, the terms "disease characterized by presentation of an antigen" denotes a disease involving cells characterized by presentation of an antigen, in particular with class I MHC. Presentation of an antigen by a cell may be effected by transfecting the cell with a nucleic acid such as RNA encoding the antigen.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect such as induction of a humoral and/or cellular immune response, the strength and/or duration of the induced immune reaction, or the specificity of the induced immune reaction.

The term "immune effector functions" in the context of the present invention includes any functions mediated by components of the immune system that result, for example, in the killing of infected cells or cancer cells, or in the inhibition of tumor growth and/or inhibition of tumor development, including inhibition of tumor dissemination and metastasis. Preferably, the immune effector functions in the context of the present invention are T cell mediated effector functions. Such functions comprise in the case of a helper T cell (CD4$^+$ T cell) the recognition of an antigen or an antigen peptide in the context of MHC class II molecules by T cell receptors, the release of cytokines and/or the activation of CD8$^+$ lymphocytes (CTLs) and/or B-cells, and in the case of CTL the recognition of an antigen or an antigen peptide in the context of MHC class I molecules by T cell receptors, the elimination of cells presented in the context of MHC class I molecules, i.e., cells characterized by presentation of an antigen with class I MHC, for example, via apoptosis or perforin-mediated cell lysis, production of cytokines such as IFN-γ and TNF-α, and specific cytolytic killing of antigen expressing target cells.

A nucleic acid is according to the invention preferably deoxyribonucleic acid (DNA) or ribonucleic acid (RNA), more preferably RNA, most preferably in vitro transcribed RNA (IVT RNA) or synthetic RNA. Nucleic acids include according to the invention genomic DNA, cDNA, mRNA, recombinantly produced and chemically synthesized molecules. A nucleic acid may according to the invention be in the form of a molecule which is single stranded or double stranded and linear or closed covalently to form a circle. A nucleic can be employed for introduction into, i.e. transfection of, cells, for example, in the form of RNA which can be prepared by in vitro transcription from a DNA template. The RNA can moreover be modified before application by stabilizing sequences, capping, and polyadenylation.

Nucleic acids may be comprised in a vector. The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a β-D-ribofuranosyl group. The term includes double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' non translated region (5'-UTR), a protein or peptide coding region and a 3' non translated region (3'-UTR). mRNA has a limited half-time in cells and in vitro. Preferably, mRNA is produced by in vitro transcription using a DNA template. In one embodiment of the invention, the RNA is obtained by in vitro transcription or chemical synthesis. The in vitro transcription methodology is known to the skilled person. For example, there is a variety of in vitro transcription kits commercially available.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription".

The term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, RNA may be obtained by in vitro transcription of an appropriate DNA template. The promoter for controlling transcription can be any promoter for any RNA polymerase. Particular examples of RNA polymerases are the T7, T3, and SP6 RNA polymerases. A DNA template for in vitro transcription may be obtained by cloning of a nucleic acid, in particular cDNA, and introducing it into an appropriate vector for in vitro transcription. The cDNA may be obtained by reverse transcription of RNA. Preferably cloning vectors are used for producing transcripts which generally are designated as transcription vectors.

The term "expression" is used herein in its broadest meaning and comprises the production of RNA and/or of protein or peptide. With respect to RNA, the term "expression" or "translation" relates in particular to the production of peptides or proteins. Expression may be transient or may be stable. According to the invention, the term expression also includes an "aberrant expression" or "abnormal expression".

"Aberrant expression" or "abnormal expression" means according to the invention that expression is altered, preferably increased, compared to a reference, e.g. a state in a subject not having a disease associated with aberrant or abnormal expression of a certain protein, e.g., a tumor antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa. In some embodiments, a tumor antigen may also be specifically expressed under normal conditions in more than one tissue type or organ, such as in 2 or 3 tissue types or organs, but preferably in not more than 3 different tissue or organ types. In this case, the tumor antigen is then specifically expressed in these organs. For example, if a tumor antigen is expressed under normal conditions preferably to an approximately equal extent in lung and stomach, said tumor antigen is specifically expressed in lung and stomach.

The term "translation" according to the invention relates to the process in the ribosomes of a cell by which a strand of messenger RNA directs the assembly of a sequence of amino acids to make a protein or peptide.

According to the invention, the term "RNA encoding" means that RNA, if present in the appropriate environment, preferably within a cell, such as an antigen-presenting cell, in particular a dendritic cell, can be expressed to produce a protein or peptide it encodes.

According to the invention, the stability and translation efficiency of RNA may be modified as required. The term "modification" in the context of RNA as used according to the present invention includes any modification of RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5'-cap" includes a 5'-cap analog that resembles the RNA cap structure and is modified to possess the ability to stabilize RNA and/or enhance translation of RNA if attached thereto, preferably in vivo and/or in a cell.

Preferably, the 5' end of the RNA includes a cap structure having the following general formula:

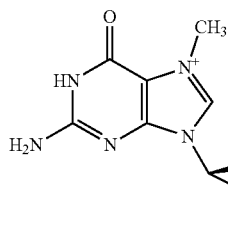 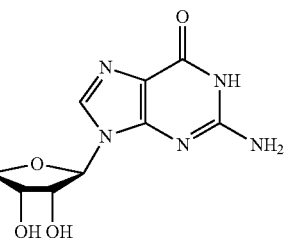

wherein $R_1$ and $R_2$ are independently hydroxy or methoxy and $W^-$, $X^-$ and $Y^-$ are independently oxygen, sulfur, selenium, or $BH_3$. In a preferred embodiment, $R_1$ and $R_2$ are hydroxy and $W^-$, $X^-$ and $Y^-$ are oxygen. In a further preferred embodiment, one of $R_1$ and $R_2$, preferably $R_1$ is hydroxy and the other is methoxy and $W^-$, $X^-$ and $Y^-$ are oxygen. In a further preferred embodiment, $R_1$ and $R_2$ are hydroxy and one of $W^-$, $X^-$ and $Y^-$, preferably $X^-$ is sulfur, selenium, or $BH_3$, preferably sulfur, while the other are oxygen. In a further preferred embodiment, one of $R_1$ and $R_2$, preferably $R_2$ is hydroxy and the other is methoxy and one of $W^-$, $X^-$ and $Y^-$, preferably $X^-$ is sulfur, selenium, or $BH_3$, preferably sulfur while the other are oxygen.

In the above formula, the nucleotide on the right hand side is connected to the RNA chain through its 3' group.

Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the exchange of the existing 3'-UTR with or the insertion of one or more, preferably two copies of a 3'-UTR derived from a globin gene, such as alpha2-globin, alpha1-globin, beta-globin, preferably beta-globin, more preferably human beta-globin.

RNA having an unmasked poly-A sequence is translated more efficiently than RNA having a masked poly-A sequence.

The term "poly(A) tail" or "poly-A sequence" relates to a sequence of adenyl (A) residues which typically is located on the 3'-end of a RNA molecule and "unmasked poly-A sequence" means that the poly-A sequence at the 3' end of an RNA molecule ends with an A of the poly-A sequence and is not followed by nucleotides other than A located at the 3' end, i.e. downstream, of the poly-A sequence. Furthermore, a long poly-A sequence of about 120 base pairs results in an optimal transcript stability and translation efficiency of RNA.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. To further increase stability and/or expression of the RNA used according to the invention, the poly-A sequence can be unmasked.

In addition, incorporation of a 3'-non translated region (UTR) into the 3'-non translated region of an RNA molecule can result in an enhancement in translation efficiency. A synergistic effect may be achieved by incorporating two or more of such 3'-non translated regions. The 3'-non translated regions may be autologous or heterologous to the RNA into which they are introduced. In one particular embodiment the 3'-non translated region is derived from the human β-globin gene.

A combination of the above described modifications, i.e. incorporation of a poly-A sequence, unmasking of a poly-A sequence and incorporation of one or more 3'-non translated regions, has a synergistic influence on the stability of RNA and increase in translation efficiency.

In order to increase expression of the RNA used according to the present invention, it may be modified within the coding region, i.e. the sequence encoding the expressed peptide or protein, preferably without altering the sequence of the expressed peptide or protein, so as to increase the GC-content to increase mRNA stability and to perform a codon optimization and, thus, enhance translation in cells.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

Of course, if according to the present invention it is desired to decrease stability and/or translation efficiency of RNA, it is possible to modify RNA so as to interfere with the function of elements as described above increasing the stability and/or translation efficiency of RNA.

The average "diameter" or "size" of the nanoparticles described herein is generally the "design size" or intended size of the nanoparticles prepared according to an established process. Size may be a directly measured dimension, such as average or maximum diameter, or may be determined by an indirect assay such as a filtration screening assay. Direct measurement of particle size is typically carried out by dynamic light scattering. Frequently, the results from dynamic light scattering measurements are expressed in terms of $Z_{average}$ (a measure for the average size) and the polydispersity index, PI or PDI (a measure for the polydispersity). As minor variations in size arise during the manufacturing process, a variation up to 40% of the stated measurement is acceptable and considered to be within the stated size. Alternatively, size may be determined by filtration screening assays. For example, a particle preparation is less than a stated size, if at least 97% of the particles pass through a "screen-type" filter of the stated size.

Preferably, RNA if delivered to, i.e. transfected into, a cell, in particular a cell present in vivo, such as a dendritic cell, expresses the protein, peptide or antigen it encodes.

The term "transfection" relates to the introduction of nucleic acids, in particular RNA, into a cell. For purposes of the present invention, the term "transfection" also includes the introduction of a nucleic acid into a cell such as an antigen-presenting cell or the uptake of a nucleic acid by such cell, wherein the cell may be present in a subject, e.g., a patient.

According to the invention it is preferred that introduction of RNA encoding an antigen into cells results in expression of said antigen.

The term "peptide" according to the invention comprises oligo- and polypeptides and refers to substances comprising two or more, preferably 3 or more, preferably 4 or more, preferably 6 or more, preferably 8 or more, preferably 9 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

The term "cell" preferably is an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transfected with an exogenous nucleic acid. The term "cell" includes according to the invention prokaryotic cells (e.g., *E. coli*) or eukaryotic cells (e.g., dendritic cells, B cells, CHO cells, COS cells, K562 cells, HEK293 cells, HELA cells, yeast cells, and insect cells). The exogenous nucleic acid may be found inside the cell (i) freely dispersed as such, (ii) incorporated in a recombinant vector, or (iii) integrated into the host cell genome or mitochondrial DNA. Mammalian cells are particularly preferred, such as cells from humans, mice, hamsters, pigs, goats, and primates. The cells may be derived from a large number of tissue types and include primary cells and cell lines. Specific examples include keratinocytes, peripheral blood leukocytes, bone marrow stem cells, and embryonic stem cells. In further embodiments, the cell is an antigen-presenting cell, in particular a dendritic cell, a monocyte, or macrophage.

As used herein, the term "nanoparticle" refers to any particle having a diameter making the particle suitable for systemic, in particular parenteral, administration, of, in particular, nucleic acids, typically a diameter of less than 1000 nanometers (nm). In some embodiments, a nanoparticle has a diameter of less than 600 nm. In some embodiments, a nanoparticle has a diameter of less than 400 nm.

As used herein, the term "nanoparticulate formulation" or similar terms refer to any substance that contains at least one nanoparticle. In some embodiments, a nanoparticulate composition is a uniform collection of nanoparticles. In some embodiments, nanoparticulate compositions are dispersions or emulsions. In general, a dispersion or emulsion is formed when at least two immiscible materials are combined.

The term, "lipoplex" or "RNA lipoplex" refers to a complex of lipids and nucleic acids such as RNA. Lipoplexes are formed spontaneously when cationic liposomes, which often also include a neutral "helper" lipid, are mixed with nucleic acids.

Zeta potential is a scientific term for electrokinetic potential in colloidal systems. From a theoretical viewpoint, zeta potential is the electric potential in the interfacial double layer at the location of the slipping plane versus a point in the bulk fluid away from the interface. In other words, zeta potential is the potential difference between the dispersion medium and the stationary layer of fluid attached to the dispersed particle. Zeta potential is widely used for quantification of the magnitude of the electrical charge at the double layer.

Zeta potential can be calculated using theoretical models and experimentally-determined electrophoretic mobility or dynamic electrophoretic mobility measurements. Electrokinetic phenomena and electroacoustic phenomena are the usual sources of data for calculation of zeta potential.

Electrophoresis may be used for estimating zeta potential of particulates. In practice, the zeta potential of a dispersion can be measured by applying an electric field across the dispersion. Particles within the dispersion with a zeta potential will migrate toward the electrode of opposite charge with a velocity proportional to the magnitude of the zeta potential. This velocity may be measured using the technique of the Laser Doppler Anemometer. The frequency shift or phase shift of an incident laser beam caused by these moving particles may be measured as the particle mobility, and this mobility may be converted to the zeta potential by inputting the dispersant viscosity and dielectric permittivity, and the application of the Smoluchowski theories.

Electrophoretic velocity is proportional to electrophoretic mobility, which is the measurable parameter. There are several theories that link electrophoretic mobility with zeta potential.

Suitable systems such as the Nicomp 380 ZLS system can be used for determining the zeta potential. Such systems usually measure the electrophoretic mobility and stability of charged particles in liquid suspension. These values are a predictor of the repulsive forces being exerted by the particles in suspension and are directly related to the stability of the colloidal system. A zeta potential may be measured according to a protocol as described below.

Electric charge is a physical property that causes a matter to experience a force when near other electrically charged matter. Electric charge comes in two types, called positive and negative. Charged particles whose charges have the same sign repel one another, and particles whose charges have different signs attract.

The electric charge of a macroscopic object such as a particle is the sum of the electric charges of the particles that make it up. The nanoparticles described herein may have equal numbers of positive and negative charges, in which case their charges cancel out, yielding a net charge of zero, thus making the nanoparticles neutral. Net charge is the charge on a whole object such as a compound.

An ion having an overall net positive charge is a cation while an ion having an overall net negative charge is an anion.

Nanoparticles described herein can be formed by adjusting a positive to negative charge, depending on the (+/−) charge ratio of the cationic lipid to the RNA and mixing the RNA and the cationic lipid. The +/− charge ratio of the cationic lipid to the RNA in the nanoparticles described herein can be calculated by the following equation. (+/− charge ratio)=[(cationic lipid amount (mol))*(the total number of positive charges in the cationic lipid)]:[(RNA amount (mol))*(the total number of negative charges in RNA)]. The RNA amount and the cationic lipid amount can be easily determined by one skilled in the art in view of a loading amount upon preparation of the nanoparticles.

According to an embodiment, the ratio of positive to negative charge in nanoparticles suitable for the invention is such that they may have a global negative charge or a global charge at or near the neutrality.

If the present invention refers to a charge such as a positive charge, negative charge or neutral charge or a cationic compound, negative compound or neutral compound this generally means that the charge mentioned is present at a selected pH, such as a physiological pH. For example, the term "cationic lipid" means a lipid having a net positive charge at a selected pH, such as a physiological pH. The term "neutral lipid" means a lipid having no net positive or negative charge and can be present in the form of a non-charge or a neutral amphoteric ion at a selected pH, such as a physiological pH. By "physiological pH" herein is meant a pH of about 7.5.

The nanoparticulate carriers such as lipid carriers contemplated for use in the present invention include any substances or vehicles with which RNA can be associated, e.g. by forming complexes with the RNA or forming vesicles in which the RNA is enclosed or encapsulated. This may result in increased stability of the RNA compared to naked RNA. In particular, stability of the RNA in blood may be increased.

Cationic lipids, cationic polymers and other substances with positive charges may form complexes with negatively charged nucleic acids. These cationic molecules can be used to complex nucleic acids, thereby forming e.g. so-called lipoplexes or polyplexes, respectively, and these complexes have been shown to deliver nucleic acids into cells.

Nanoparticulate RNA preparations can be obtained by various protocols and from various RNA complexing compounds. Lipids, polymers, oligomers, or amphipiles are typical complexing agents. In one embodiment, the complexing compound comprises at least one agent selected from the group consisting protamine, polyethyleneimine, a poly-L-lysine, a poly-L-arginine or a histone.

According to the invention, protamine is useful as cationic carrier agent. The term "protamine" refers to any of various strongly basic proteins of relatively low molecular weight that are rich in arginine and are found associated especially with DNA in place of somatic histones in the sperm cells of various animals (as fish). In particular, the term "protamine" refers to proteins found in fish sperm that are strongly basic, are soluble in water, are not coagulated by heat, and yield chiefly arginine upon hydrolysis. In purified form, they are used in a long-acting formulation of insulin and to neutralize the anticoagulant effects of heparin.

According to the invention, the term "protamine" as used herein is meant to comprise any protamine amino acid sequence obtained or derived from native or biological sources including fragments thereof and multimeric forms of said amino acid sequence or fragment thereof. Furthermore, the term encompasses (synthesized) polypeptides which are artificial and specifically designed for specific purposes and cannot be isolated from native or biological sources.

The protamine used according to the present invention can be sulfated protamine or hydrochloride protamine. In a preferred embodiment, the protamine source used for the production of the nanoparticles described herein is protamine 5000 which contains protamine at more than 10 mg/ml (5000 heparin-neutralizing units per ml) in an isotonic salt solution.

Liposomes are microscopic lipidic vesicles often having one or more bilayers of a vesicle-forming lipid, such as a phospholipid, and are capable of encapsulating a drug. Different types of liposomes may be employed in the context of the present invention, including, without being limited thereto, multilamellar vesicles (MLV), small unilamellar vesicles (SUV), large unilamellar vesicles (LUV), sterically stabilized liposomes (SSL), multivesicular vesicles (MV), and large multivesicular vesicles (LMV) as well as other bilayered forms known in the art. The size and lamellarity of the liposome will depend on the manner of preparation and the selection of the type of vesicles to be used will depend on the preferred mode of administration. There are several other forms of supramolecular organization in which lipids may be present in an aqueous medium, comprising lamellar phases, hexagonal and inverse hexagonal phases, cubic phases, micelles, reverse micelles composed of monolayers. These phases may also be obtained in the combination with DNA or RNA, and the interaction with RNA and DNA may substantially affect the phase state. The described phases may be present in the nanoparticulate RNA formulations of the present invention.

For formation of RNA lipoplexes from RNA and liposomes, any suitable method of forming liposomes can be used so long as it provides the envisaged RNA lipoplexes. Liposomes may be formed using standard methods such as the reverse evaporation method (REV), the ethanol injection method, the dehydration-rehydration method (DRV), sonication or other suitable methods.

After liposome formation, the liposomes can be sized to obtain a population of liposomes having a substantially homogeneous size range.

Bilayer-forming lipids have typically two hydrocarbon chains, particularly acyl chains, and a head group, either polar or nonpolar. Bilayer-forming lipids are either composed of naturally-occurring lipids or of synthetic origin, including the phospholipids, such as phosphatidylcholine, phosphatidylethanolamine, phosphatide acid, phosphatidylinositol, and sphingomyelin, where the two hydrocarbon chains are typically between about 14-22 carbon atoms in length, and have varying degrees of unsaturation. Other suitable lipids for use in the composition of the present invention include glycolipids and sterols such as cholesterol and its various analogs which can also be used in the liposomes.

Cationic lipids typically have a lipophilic moiety, such as a sterol, an acyl or diacyl chain, and have an overall net positive charge. The head group of the lipid typically carries the positive charge. The cationic lipid preferably has a positive charge of 1 to 10 valences, more preferably a positive charge of 1 to 3 valences, and more preferably a positive charge of 1 valence. Examples of cationic lipids include, but are not limited to 1,2-di-O-octadecenyl-3-trimethylammonium propane (DOTMA); dimethyldioctadecylammonium (DDAB); 1,2-dioleoyl-3-trimethylammonium-propane (DOTAP); 1,2-dioleoyl-3-dimethylammonium-propane (DODAP); 1,2-diacyloxy-3-dimethylammonium propanes; 1,2-dialkyloxy-3-dimethylammonium propanes; dioctadecyldimethyl ammonium chloride (DODAC), 1,2-dimyristoyloxypropyl-1,3-dimethylhydroxyethyl ammonium (DMRIE), and 2,3-dioleoyloxy-N-[2(spermine carboxamide)ethyl]-N,N-dimethyl-1-propanamium trifluoroacetate (DOSPA). Preferred are DOTMA, DOTAP, DODAC, and DOSPA. Most preferred is DOTMA.

In addition, the nanoparticles described herein preferably further include a neutral lipid in view of structural stability and the like. The neutral lipid can be appropriately selected in view of the delivery efficiency of the RNA-lipid complex. Examples of neutral lipids include, but are not limited to, 1,2-di-(9Z-octadecenoyl)-sn-glycero-3-phosphoethanolamine (DOPE), 1,2-dioleoyl-sn-glycero-3-phosphocholine (DOPC), diacylphosphatidyl choline, diacylphosphatidyl ethanol amine, ceramide, sphingoemyelin, cephalin, sterol, and cerebroside. Preferred is DOPE and/or DOPC. Most preferred is DOPE. In the case where a cationic liposome includes both a cationic lipid and a neutral lipid, the molar ratio of the cationic lipid to the neutral lipid can be appropriately determined in view of stability of the liposome and the like.

According to one embodiment, the nanoparticles described herein may comprise phospholipids. The phospholipids may be a glycerophospholipid. Examples of glycerophospholipid include, without being limited thereto, three types of lipids: (i) zwitterionic phospholipids, which include, for example, phosphatidylcholine (PC), egg yolk phosphatidylcholine, soybean-derived PC in natural, partially hydrogenated or fully hydrogenated form, dimyristoyl phosphatidylcholine (DMPC) sphingomyelin (SM); (ii) negatively charged phospholipids: which include, for example, phosphatidylserine (PS), phosphatidylinositol (PI), phosphatidic acid (PA), phosphatidylglycerol (PG) dipalmipoyl PG, dimyristoyl phosphatidylglycerol (DMPG); synthetic derivatives in which the conjugate renders a zwitterionic phospholipid negatively charged such is the case of methoxy-polyethylene, glycol-distearoyl phosphatidylethanolamine (mPEG-DSPE); and (iii) cationic phospholipids, which include, for example, phosphatidylcholine or sphingomyelin of which the phosphomonoester was O-methylated to form the cationic lipids.

Association of RNA to the lipid carrier can occur, for example, by the RNA filling interstitial spaces of the carrier, such that the carrier physically entraps the RNA, or by covalent, ionic, or hydrogen bonding, or by means of adsorption by non-specific bonds. Whatever the mode of association, the RNA must retain its therapeutic, i.e. antigen-encoding, properties.

The "polydispersity index" is a measurement of the homogeneous or heterogeneous size distribution of the individual particles such as liposomes in a particle mixture and indicates the breadth of the particle distribution in a mixture. The PI can be determined, for example, as described herein.

As used herein, the term "bivalent cation" is intended to mean a positively charged element, atom or molecule having a charge of plus 2. The term includes metal ions such as $Ca^{2+}$, $Zn^{2+}$, $Mn^{2+}$, $Mg^{2+}$, $Fe^{2+}$, $Co^{2+}$, $Ni^{2+}$ and/or $Cu^{2+}$. Bivalent cations according to the invention also include salt forms of the ions. Specific examples of bivalent salt forms include $CaCl_2$, $ZnCl_2$, $MnSO_4$, $MnCl_2$ and $MgCl_2$ and other combinations of the above exemplary divalent cations in a salt form with, for example, chloride (Cl), sulfate ($SO_4$), acetate and/or phosphate. Bivalent cations and salt forms other than those exemplified above are well known in the art and included in the meaning of the term as it is used herein.

The term "monovalent ion" includes a cation that has a charge of plus 1. Typically, the term includes alkali metals such as lithium, sodium, potassium, rubidium, and caesium.

The term "portion" refers to a fraction. With respect to a particular structure such as an amino acid sequence or protein the term "portion" thereof may designate a continuous or discontinuous fraction of said structure. Preferably, a portion of an amino acid sequence comprises at least 1%, at least 5%, at least 10%, at least 20%, at least 30%, preferably at least 40%, preferably at least 50%, more preferably at least 60%, more preferably at least 70%, even more preferably at least 80%, and most preferably at least 90% of the amino acids of said amino acid sequence. Preferably, if the portion is a discontinuous fraction said discontinuous fraction is composed of 2, 3, 4, 5, 6, 7, 8, or more parts of a structure, each part being a continuous element of the structure. For example, a discontinuous fraction of an amino acid sequence may be composed of 2, 3, 4, 5, 6, 7, 8, or more, preferably not more than 4 parts of said amino acid sequence, wherein each part preferably comprises at least 5 continuous amino acids, at least 10 continuous amino acids, preferably at least 20 continuous amino acids, preferably at least 30 continuous amino acids of the amino acid sequence.

The terms "part" and "fragment" are used interchangeably herein and refer to a continuous element. For example, a part of a structure such as an amino acid sequence or protein refers to a continuous element of said structure. A portion, a part or a fragment of a structure preferably comprises one or more functional properties of said structure. For example, a portion, a part or a fragment of an epitope, peptide or protein is preferably immunologically equivalent to the epitope, peptide or protein it is derived from. In the context of the present invention, a "part" of a structure such as an amino acid sequence preferably comprises, preferably consists of at least 10%, at least 20%, at least 30%, at least 40%, at least 50%, at least 60%, at least 70%, at least 80%, at least 85%, at least 90%, at least 92%, at least 94%, at least 96%, at least 98%, at least 99% of the entire structure or amino acid sequence.

"Reduce" or "inhibit" as used herein means the ability to cause an overall decrease, preferably of 5% or greater, 10% or greater, 20% or greater, more preferably of 50% or greater, and most preferably of 75% or greater, in the level. The term "inhibit" or similar phrases includes a complete or essentially complete inhibition, i.e. a reduction to zero or essentially to zero.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%, at least 200%, at least 500%, at least 1000%, at least 10000% or even more.

The agents, compositions and methods described herein can be used to treat a subject with a disease, e.g., a disease characterized by the presence of diseased cells expressing an antigen and presenting an antigen peptide. Examples of diseases which can be treated and/or prevented encompass all diseases expressing one of the antigens described herein. Particularly preferred diseases are infectious diseases such as viral diseases and cancer diseases. The agents, compositions and methods described herein may also be used for immunization or vaccination to prevent a disease described herein.

According to the invention, the term "disease" refers to any pathological state, including infectious diseases and cancer diseases, in particular those forms of infectious diseases and cancer diseases described herein.

A disease to be treated according to the invention is preferably a disease involving an antigen. "Disease involving an antigen" or similar expressions means according to the invention that the antigen is expressed in cells of a diseased tissue or organ. Expression in cells of a diseased tissue or organ may be increased compared to the state in a healthy tissue or organ. In one embodiment, expression is only found in a diseased tissue, while expression in a healthy tissue is repressed. According to the invention, diseases involving an antigen include infectious diseases and cancer diseases, wherein the disease-associated antigen is preferably an antigen of the infectious agent and a tumor antigen, respectively. Preferably a disease involving an antigen preferably is a disease involving cells expressing an antigen and presenting the antigen in the context of MHC molecules, in particular with class I MHC.

The terms "normal tissue" or "normal conditions" refer to healthy tissue or the conditions in a healthy subject, i.e., non-pathological conditions, wherein "healthy" preferably means non-infected or non-cancerous.

Cancer or cancer disease (medical term: malignant neoplasm) is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor, i.e. a swelling or lesion formed by an abnormal growth of cells (called neoplastic cells or tumor cells), but some, like leukemia, do not. The term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases.

Examples of cancers treatable with the nanoparticles and pharmaceutical composition of the present invention include malignant melanoma, all types of carcinoma (colon, renal cell, bladder, prostate, non-small cell and small cell lung carcinoma, etc.), lymphomas, sarcomas, blastomas, gliomas, etc.

Malignant melanoma is a serious type of skin cancer. It is due to uncontrolled growth of pigment cells, called melanocytes.

According to the invention, a "carcinoma" is a malignant tumor derived from epithelial cells. This group represents the most common cancers, including the common forms of breast, prostate, lung and colon cancer.

Lymphoma and leukemia are malignancies derived from hematopoietic (blood-forming) cells.

A sarcoma is a cancer that arises from transformed cells in one of a number of tissues that develop from embryonic mesoderm. Thus, sarcomas include tumors of bone, cartilage, fat, muscle, vascular, and hematopoietic tissues.

Blastic tumor or blastoma is a tumor (usually malignant) which resembles an immature or embryonic tissue. Many of these tumors are most common in children.

A glioma is a type of tumor that starts in the brain or spine. It is called a glioma because it arises from glial cells. The most common site of gliomas is the brain.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

Examples of infectious diseases treatable with the nanoparticles and pharmaceutical compositions of the present invention include viral infectious diseases, such as AIDS (HIV), hepatitis A, B or C, herpes, herpes zoster (chickenpox), German measles (rubella virus), yellow fever, dengue etc. flaviviruses, influenza viruses, hemorrhagic infectious diseases (Marburg or Ebola viruses), bacterial infectious diseases, such as Legionnaire's disease (*Legionella*), gastric ulcer (*Helicobacter*), cholera (*Vibrio*), infections by *E. coli, Staphylococci, Salmonella* or *Streptococci* (tetanus); infections by protozoan pathogens such as malaria, sleeping sickness, leishmaniasis; toxoplasmosis, i.e. infections by *Plasmodium, Trypanosoma, Leishmania* and *Toxoplasma*; or fungal infections, which are caused e.g. by *Cryptococcus neoformans, Histoplasma capsulatum, Coccidioides immitis, Blastomyces dermatitidis* or *Candida albicans*).

By "treat" is meant to administer a compound or composition as described herein to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject. In particular, the term "treatment of a disease" includes curing, shortening the duration, ameliorating, preventing, slowing down or inhibiting progression or worsening, or preventing or delaying the onset of a disease or the symptoms thereof.

The term "immunotherapy" relates to a treatment involving activation of a specific immune response and/or immune effector function(s). Immunotherapy may be performed using any of a variety of techniques, in which agents provided herein function to remove antigen-expressing cells from a patient. Such removal may take place as a result of enhancing or inducing an immune response and/or immune effector function(s) in a patient specific for an antigen or a cell expressing an antigen.

In the context of the present invention, terms such as "protect", "prevent", "prophylactic", "preventive", or "protective" relate to the prevention or treatment or both of the occurrence and/or the propagation of a disease in a subject and, in particular, to minimizing the chance that a subject will develop a disease or to delaying the development of a disease. For example, a person at risk for cancer would be a candidate for therapy to prevent cancer.

A prophylactic administration of an immunotherapy, for example, a prophylactic administration of the composition of the invention, preferably protects the recipient from the development of a disease. A therapeutic administration of an immunotherapy, for example, a therapeutic administration of the composition of the invention, may lead to the inhibition of the progress/growth of the disease. This comprises the deceleration of the progress/growth of the disease, in particular a disruption of the progression of the disease, which preferably leads to elimination of the disease.

By "being at risk" is meant a subject that is identified as having a higher than normal chance of developing a disease, in particular cancer, compared to the general population. In addition, a subject who has had, or who currently has, a disease, in particular cancer is a subject who has an increased risk for developing a disease, as such a subject may continue to develop a disease. Subjects who currently have, or who have had, a cancer also have an increased risk for cancer metastases.

The agents and compositions provided herein may be used alone or in combination with conventional therapeutic regimens such as surgery, irradiation, chemotherapy and/or bone marrow transplantation (autologous, syngeneic, allogeneic or unrelated).

Treatment of cancer represents a field where combination strategies are especially desirable since frequently the combined action of two, three, four or even more cancer drugs/therapies generates synergistic effects which are considerably stronger than the impact of a monotherapeutic approach. Thus, in another embodiment of the present invention, a cancer treatment which utilizes immune- or vaccination-based mechanisms such as the methods and pharmaceutical compositions of the present invention may be effectively combined with various other drugs and/or methods targeting similar or other specific mechanisms. Among those are e.g. combinations with conventional tumor therapies, multi-epitope strategies, additional immunotherapy, and treatment approaches targeting angiogenesis or apoptosis (for review see e.g. Andersen et al. 2008: Cancer treatment: the combination of vaccination with other therapies. Cancer Immunology Immunotherapy, 57(11): 1735-1743.) Sequential administration of different agents may inhibit cancer cell growth at different check points, while other agents may e.g. inhibit neo-angiogenesis, survival of malignant cells or metastases, potentially converting cancer into a chronic disease. The following list provides some non-limiting examples of anti-cancer drugs and therapies which can be used in combination with the present invention:

1. Chemotherapy

Chemotherapy is the standard of care for multiple types of cancer. The most common chemotherapy agents act by killing cells that divide rapidly, one of the main properties of cancer cells. Thus, a combination with conventional chemotherapeutic drugs such as e.g. alkylating agents, antimetabolites, anthracyclines, plant alkaloids, topoisomerase inhibitors, and other antitumour agents which either affect cell division or DNA synthesis may significantly improve the therapeutic effects of the present invention by clearing suppressor cells, reboot of the immune system, by rendering tumor cells more susceptible to immune mediated killing, or by additional activation of cells of the immune system. A synergistic anti-cancer action of chemotherapeutic and vaccination-based immunotherapeutic drugs has been demonstrated in multiple studies (see e.g. Quoix et al. 2011: Therapeutic vaccination with TG4010 and first-line chemotherapy in advanced non-small-cell lung cancer: a controlled phase 2B trial. Lancet Oncol. 12(12): 1125-33.; see also Liseth et al. 2010: Combination of intensive chemotherapy and anticancer vaccines in the treatment of human malignancies: the hematological experience. J Biomed Biotechnol. 2010: 6920979; see also Hirooka et al 2009: A combination therapy of gemcitabine with immunotherapy for patients with inoperable locally advanced pancreatic cancer. Pancreas 38(3): e69-74). There are hundreds of chemotherapeutic drugs available which are basically suitable for combination therapies. Some (non-limiting) examples of chemotherapeutic drugs which can be combined with the present invention are carboplatin (Paraplatin), cisplatin (Platinol, Platinol-AQ), cyclophosphamide (Cytoxan, Neosar), docetaxel (Taxotere), doxorubicin (Adriamycin), erlotinib (Tarceva), etoposide (VePesid), fluorouracil (5-FU), gemcitabine (Gemzar), imatinib mesylate (Gleevec), irinotecan (Camptosar), methotrexate (Folex, Mexate, Amethopterin), paclitaxel (Taxol, Abraxane), sorafinib (Nexavar), sunitinib (Sutent), topotecan (Hycamtin), vincristine (Oncovin, Vincasar PFS), and vinblastine (Velban).

2. Surgery

Cancer surgery—an operation to remove the tumor—remains the foundation of cancer treatment. Surgery can be combined with other cancer treatments in order to delete any remaining tumor cells. Combining surgical methods with subsequent immunotherapeutic treatment is a promising approach which has been demonstrated countless times.

3. Radiation

Radiation therapy remains an important component of cancer treatment with approximately 50% of all cancer patients receiving radiation therapy during their course of illness. The main goal of radiation therapy is to deprive cancer cells of their multiplication (cell division) potential. The types of radiation used to treat cancer are photons radiation (x-rays and gamma rays) and particle radiations (electron, proton and neutron beams.) There are two ways to deliver the radiation to the location of the cancer. External beam radiation is delivered from outside the body by aiming high-energy rays (photons, protons or particle radiation) to the location of the tumor. Internal radiation or brachytherapy is delivered from inside the body by radioactive sources, sealed in catheters or seeds directly into the tumor site. Radiation therapy techniques which are applicable in combination with the present invention are e.g. fractionation (radiation therapy delivered in a fractionated regime, e.g. daily fractions of 1.5 to 3 Gy given over several weeks), 3D conformal radiotherapy (3DCRT; delivering radiation to the gross tumor volume), intensity modulated radiation therapy (IMRT; computer-controlled intensity modulation of multiple radiation beams), image guided radiotherapy (IGRT; a technique comprising pre-radiotherapy imaging which allows for correction), and stereotactic body radiation therapy (SRBT, delivers very high individual doses of radiation over only a few treatment fractions). For a radiation therapy review see Baskar et al. 2012: Cancer and radiation therapy: current advances and future directions. Int. J Med Sci. 9(3): 193-199.

4. Antibodies

Antibodies (preferably monoclonal antibodies) achieve their therapeutic effect against cancer cells through various mechanisms. They can have direct effects in producing apoptosis or programmed cell death. They can block components of signal transduction pathways such as e.g. growth factor receptors, effectively arresting proliferation of tumor cells. In cells that express monoclonal antibodies, they can bring about anti-idiotype antibody formation. Indirect effects include recruiting cells that have cytotoxicity, such as monocytes and macrophages. This type of antibody-mediated cell kill is called antibody-dependent cell mediated cytotoxicity (ADCC). Antibodies also bind complement, leading to direct cell toxicity, known as complement dependent cytotoxicity (CDC). Combining surgical methods with immunotherapeutic drugs or methods is an successful approach, as e.g. demonstrated in Gadri et al. 2009: Synergistic effect of dendritic cell vaccination and anti-CD20 antibody treatment in the therapy of murine lymphoma. J Immunother. 32(4): 333-40. The following list provides some non-limiting examples of anti-cancer antibodies and potential antibody targets (in brackets) which can be used in combination with the present invention: Abagovomab (CA-125), Abciximab (CD41), Adecatumumab (EpCAM), Afutuzumab (CD20), Alacizumab pegol (VEGFR2), Altumomab pentetate (CEA), Amatuximab (MORAb-009), Anatumomab mafenatox (TAG-72), Apolizumab (HLA-DR), Arcitumomab (CEA), Bavituximab (phosphatidylserine), Bectumomab (CD22), Belimumab (BAFF), Bevacizumab (VEGF-A), Bivatuzumab mertansine (CD44 v6), Blinatumomab (CD19), Brentuximab vedotin (CD30 TNFRSF8), Cantuzumab mertansin (mucin CanAg), Cantuzumab ravtansine (MUC1), Capromab pendetide (prostatic carcinoma cells), Carlumab (CNT0888), Catumaxomab (EpCAM, CD3), Cetuximab (EGFR), Citatuzumab bogatox (EpCAM), Cixutumumab (IGF-1 receptor), Claudiximab (Claudin), Clivatuzumab tetraxetan (MUC1), Conatumumab (TRAIL-R2), Dacetuzumab (CD40), Dalotuzumab (insulin-like growth factor I receptor), Denosumab (RANKL), Detumomab (B-lymphoma cell), Drozitumab (DR5), Ecromeximab (GD3 ganglioside), Edrecolomab (EpCAM), Elotuzumab (SLAMF7), Enavatuzumab (PDL192), Ensituximab (NPC-1C), Epratuzumab (CD22), Ertumaxomab (HER2/neu, CD3), Etaracizumab (integrin $\alpha v\beta 3$), Farletuzumab (folate receptor 1), FBTA05 (CD20), Ficlatuzumab (SCH 900105), Figitumumab (IGF-1 receptor), Flanvotumab (glycoprotein 75), Fresolimumab (TGF-$\beta$), Galiximab (CD80), Ganitumab (IGF-I), Gemtuzumab ozogamicin (CD33), Gevokizumab (IL-1$\beta$), Girentuximab (carbonic anhydrase 9 (CA-IX)), Glembatumumab vedotin (GPNMB), Ibritumomab tiuxetan (CD20), Icrucumab (VEGFR-1), Igovoma (CA-125), Indatuximab ravtansine (SDC1), Intetumumab (CD51), Inotuzumab ozogamicin (CD22), Ipilimumab (CD152), Iratumumab (CD30), Labetuzumab (CEA), Lexatumumab (TRAIL-R2), Libivirumab (hepatitis B surface antigen), Lintuzumab (CD33), Lorvotuzumab mertansine (CD56), Lucatumumab (CD40), Lumiliximab (CD23), Mapatumumab (TRAIL-R1), Matuzumab (EGFR), Mepolizumab (IL-5), Milatuzumab (CD74), Mitumomab (GD3 ganglioside), Mogamulizumab (CCR4), Moxetumomab pasudotox (CD22), Nacolomab tafenatox (C242 antigen), Naptumomab estafenatox (5T4), Narnatumab (RON), Necitumumab (EGFR), Nimotuzumab (EGFR), Nivolumab (IgG4), Ofatumumab (CD20), Olaratumab (PDGF-R $\alpha$), Onartuzumab (human scatter factor receptor kinase), Oportuzumab monatox (EpCAM), Oregovomab (CA-125), Oxelumab (OX-40), Panitumumab (EGFR), Patritumab (HER3), Pemtumoma (MUC1), Pertuzuma (HER2/neu), Pintumomab (adenocarcinoma antigen), Pritumumab (vimentin), Racotumomab (N-glycolylneuraminic acid), Radretumab (fibronectin extra domain-B), Rafivirumab (rabies virus glycoprotein), Ramucirumab (VEGFR2), Rilotumumab (HGF), Rituximab (CD20), Robatumumab (IGF-1 receptor), Samalizumab (CD200), Sibrotuzumab (FAP), Siltuximab (IL-6), Tabalumab (BAFF), Tacatuzumab tetraxetan (alpha-fetoprotein), Taplitumomab paptox (CD19), Tenatumomab (tenascin C), Teprotumumab (CD221), Ticilimumab (CTLA-4), Tigatuzumab (TRAIL-R2), TNX-650 (IL-13), Tositumomab (CD20), Trastuzumab (HER2/neu), TRBS07 (GD2), Tremelimumab (CTLA-4), Tucotuzumab celmoleukin (EpCAM), Ublituximab (MS4A1), Urelumab (4-1BB), Volociximab (integrin $\alpha 5\beta 1$), Votumumab (tumor antigen CTAA16.88), Zalutumumab (EGFR), Zanolimumab (CD4).

5. Cytokines, Chemokines, Costimulatory Molecules, Fusion Proteins

Combined usage of the antigen-coding pharmaceutical compositions of the present invention with cytokines, chemokines, costimulatory molecules and/or fusion proteins thereof to evoke beneficial immune modulation or tumor inhibition effects is another embodiment of the present invention. In order to increase the infiltration of immune cells into the tumor and facilitate the movement of antigen-presenting cells to tumor-draining lymph nodes, various chemokines with C, CC, CXC and CX3C structures might be used. Some of the most promising chemokines are e.g CCR7 and its ligands CCL19 andCCL21, furthermore CCL2, CCL3, CCL5, and CCL16. Other examples are CXCR4, CXCR7 and CXCL12. Furthermore, costimulatory or regulatory molecules such as e.g. B7 ligands (B7.1 and B7.2) are useful. Also useful are other cytokines such as e.g. interleukins especially (e.g. IL-1 to IL17), interferons (e.g. IFNalpha1 to IFNalpha8, IFNalpha10, IFNalpha13, IFNalpha14, IFNalpha16, IFNalpha17, IFNalpha21, IFNbeta1, IFNW, IFNE1 and IFNK), hematopoietic factors, TGFs (e.g. TGF-$\alpha$, TGF-$\beta$, and other members of the TGF family), finally members of the tumor necrosis factor family of receptors and their ligands as well as other stimulatory molecules, comprising but not limited to 41BB, 41BB-L, CD137, CD137L, CTLA-4GITR, GITRL, Fas, Fas-L, TNFR1, TRAIL-R1, TRAIL-R2, p75NGF-R, DR6, LT.beta.R, RANK, EDAR1, XEDAR, Fn114, Troy/Trade, TAJ, TNFRII, HVEM, CD27, CD30, CD40, 4-1BB, OX40, GITR, GITRL, TACI, BAFF-R, BCMA, RELT, and CD95 (Fas/APO-1), glucocorticoid-induced TNFR-related protein, TNF receptor-related apoptosis-mediating protein (TRAMP) and death receptor-6 (DR6). Especially CD40/CD40L and OX40/OX40L are important targets for combined immunotherapy because of their direct impact on T cell survival and proliferation. For a review see Lechner et al. 2011: Chemokines, costimulatory molecules and fusion proteins for the immunotherapy of solid tumors. Immunotherapy 3 (11), 1317-1340.

6. Bacterial Treatments

Researchers have been using anaerobic bacteria, such as *Clostridium novyi*, to consume the interior of oxygen-poor tumours. These should then die when they come in contact with the tumour's oxygenated sides, meaning they would be harmless to the rest of the body. Another strategy is to use anaerobic bacteria that have been transformed with an enzyme that can convert a non-toxic prodrug into a toxic drug. With the proliferation of the bacteria in the necrotic and hypoxic areas of the tumour, the enzyme is expressed solely in the tumour. Thus, a systemically applied prodrug is metabolised to the toxic drug only in the tumour. This has been demonstrated to be effective with the nonpathogenic anaerobe *Clostridium sporogenes*.

7. Kinase Inhibitors

Another large group of potential targets for complementary cancer therapy comprises kinase inhibitors, because the growth and survival of cancer cells is closely interlocked with the deregulation of kinase activity. To restore normal kinase activity and therefor reduce tumor growth a broad range of inhibitors is in used. The group of targeted kinases comprises receptor tyrosine kinases e.g. BCR-ABL, B-Raf, EGFR, HER-2/ErbB2, IGF-IR, PDGFR-$\alpha$, PDGFR-$\beta$, c-Kit, Flt-4, Flt3, FGFR1, FGFR3, FGFR4, CSF1R, c-Met, RON, c-Ret, ALK, cytoplasmic tyrosine kinases e.g. c-SRC, c-YES, Abl, JAK-2, serine/threonine kinases e.g. ATM, Aurora A & B, CDKs, mTOR, PKCi, PLKs, b-Raf, S6K, STK11/LKB1 and lipid kinases e.g. PI3K, SK1. Small molecule kinase inhibitors are e.g. PHA-739358, Nilotinib, Dasatinib, and PD166326, NSC 743411, Lapatinib (GW-572016), Canertinib (CI-1033), Semaxinib (SU5416), Vatalanib (PTK787/ZK222584), Sutent (SU11248), Sorafenib (BAY 43-9006) and Leflunomide (SU101). For more information see e.g. Zhang et al. 2009: Targeting cancer with small molecule kinase inhibitors. Nature Reviews Cancer 9, 28-39.

8. Toll-Like Receptors

The members of the Toll-like receptor (TLRs) family are an important link between innate and adaptive immunity and the effect of many adjuvants rely on the activation of TLRs. A large number of established vaccines against cancer incorporate ligands for TLRs for boosting vaccine responses. Besides TLR2, TLR3, TLR4 especially TLR7 and TLR 8 have been examined for cancer therapy in passive immunotherapy approaches. The closely related TLR7 and TLR8 contribute to antitumor responses by affecting immune cells, tumor cells, and the tumor microenvironment and may be activated by nucleoside analogue structures. All TLR's have been used as stand-alone immunotherapeutics or cancer vaccine adjuvants and may be synergistically combined with the formulations and methods of the present invention. For more information see van Duin et al. 2005: Triggering TLR signaling in vaccination. Trends in Immunology, 27(1):49-55.

9. Angiogenesis Inhibitors

In addition to therapies which target immune modulatory receptors affected by tumor-mediated escape mechanisms and immune suppression there are therapies which target the tumor environment. Angiogenesis inhibitors prevent the extensive growth of blood vessels (angiogenesis) that tumors require to survive. The angiogenesis promoted by tumor cells to meet their increasing nutrient and oxygen demands for example can be blocked by targeting different molecules. Non-limiting examples of angiogenesis-mediating molecules or angiogenesis inhibitors which may be combined with the present invention are soluble VEGF (VEGF isoforms VEGF121 and VEGF165, receptors VEGFR1, VEGFR2 and co-receptors Neuropilin-1 and Neuropilin-2) 1 and NRP-1, angiopoietin 2, TSP-1 and TSP-2, angiostatin and related molecules, endostatin, vasostatin, calreticulin, platelet factor-4, TIMP and CDAI, Meth-1 and Meth-2, IFN-α, -β and -γ, CXCL10, IL-4, -12 and -18, prothrombin (kringle domain-2), antithrombin III fragment, prolactin, VEGI, SPARC, osteopontin, maspin, canstatin, proliferin-related protein, restin and drugs like e.g. bevacizumab, itraconazole, carboxyamidotriazole, TNP-470, CM101, IFN-α, platelet factor-4, suramin, SU5416, thrombospondin, VEGFR antagonists, angiostatic steroids+heparin, cartilage-derived angiogenesis Inhibitory factor, matrix metalloproteinase inhibitors, 2-methoxyestradiol, tecogalan, tetrathiomolybdate, thalidomide, thrombospondin, prolactina Vβ3 inhibitors, linomide, tasquinimod, For review see Schoenfeld and Dranoff 2011: Anti-angiogenesis immunotherapy. Hum Vaccin. (9):976-81.

10. Small Molecule Targeted Therapy Drugs

Small molecule targeted therapy drugs are generally inhibitors of enzymatic domains on mutated, overexpressed, or otherwise critical proteins within the cancer cell. Prominent and non-limiting examples are the tyrosine kinase inhibitors imatinib (Gleevec/Glivec) and gefitinib (Iressa). The use of small molecules e.g. sunitinib malate and/or sorafenib tosylate targeting some kinases in combination with vaccines for cancer therapy is also described in previous patent application US2009004213.

11. Virus-Based Vaccines

There are a number of virus-based cancer vaccines available or under development which can be used in a combined therapeutic approach together with the formulations of the present invention. One advantage of the use of such viral vectors is their intrinsic ability to initiate immune responses, with inflammatory reactions occurring as a result of the viral infection creating the danger signal necessary for immune activation. An ideal viral vector should be safe and should not introduce an anti-vector immune response to allow for boosting antitumour specific responses. Recombinant viruses such as vaccinia viruses, herpes simplex viruses, adenoviruses, adeno-associated viruses, retroviruses and avipox viruses have been used in animal tumour models and based on their encouraging results, human clinical trials have been initiated. Especially important virus-based vaccines are virus-like particles (VLPs), small particles that contain certain proteins from the outer coat of a virus. Virus-like particles do not contain any genetic material from the virus and cannot cause an infection but they can be constructed to present tumor antigens on their coat. VLPs can be derived from various viruses such as e.g. the hepatitis B virus or other virus families including Parvoviridae (e.g. adeno-associated virus), Retroviridae (e.g. HIV), and Flaviviridae (e.g. Hepatitis C virus). For a general review see Sorensen and Thompsen 2007: Virus-based immunotherapy of cancer: what do we know and where are we going? APMIS 115(11):1177-93; virus-like particles against cancer are reviewed in Buonaguro et al. 2011: Developments in virus-like particle-based vaccines for infectious diseases and cancer. Expert Rev Vaccines 10(11):1569-83; and in Guillén et al. 2010: Virus-like particles as vaccine antigens and adjuvants: application to chronic disease, cancer immunotherapy and infectious disease preventive strategies. Procedia in Vaccinology 2 (2), 128-133.

12. Multi-Epitope Strategies

The use of multi epitopes shows promising results for vaccination. Fast sequencing technologies combined with intelligent algorithms systems allow the exploitation of the tumor mutanome and may provide multi epitopes for individualized vaccines which can be combined with the present invention. For more information see 2007: Vaccination of metastatic colorectal cancer patients with matured dendritic cells loaded with multiple major histocompatibility complex class I peptides. J Immunother 30: 762-772; furthermore Castle et al. 2012: Exploiting the mutanome for tumor vaccination. Cancer Res 72 (5):1081-91.

13. Adoptive T Cell Transfer

For example, a combination of a tumor antigen vaccination and T cell transfer is described in: Rapoport et al. 2011: Combination immunotherapy using adoptive T-cell transfer and tumor antigen vaccination on the basis of hTERT and survivin after ASCT for myeloma. Blood 117(3):788-97.

14. Peptide-Based Target Therapies

Peptides can bind to cell surface receptors or affected extracellular matrix surrounding the tumor. Radionuclides which are attached to these peptides (e.g. RGDs) eventually kill the cancer cell if the nuclide decays in the vicinity of the cell. Especially oligo- or multimers of these binding motifs are of great interest, since this can lead to enhanced tumor specificity and avidity. For non-limiting examples see Yamada 2011: Peptide-based cancer vaccine therapy for prostate cancer, bladder cancer, and malignant glioma. Nihon Rinsho 69(9): 1657-61.

15. Other Therapies

There are numerous other cancer therapies which can be combined with the formulations and methods of the present invention in order to create synergistic effects. Non-limiting examples are treatments targeting apoptosis, hyperthermia, hormonal therapy, telomerase therapy, insulin potentiation therapy, gene therapy and photodynamic therapy.

The term "immunization" or "vaccination" describes the process of treating a subject for therapeutic or prophylactic reasons.

The term "subject" relates to mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The term "animal" as used herein also includes humans.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "heterologous" is used to describe something consisting of multiple different elements. As an example, the transfer of one individual's bone marrow into a different individual constitutes a heterologous transplant. A heterologous gene is a gene derived from a source other than the subject.

The pharmaceutical compositions of the invention are preferably sterile and contain an effective amount of the nanoparticles described herein and optionally of further agents as discussed herein to generate the desired reaction or the desired effect.

The pharmaceutical composition of the invention may be administered together with supplementing immunity-enhancing substances such as one or more adjuvants and may comprise one or more immunity-enhancing substances to further increase its effectiveness, preferably to achieve a synergistic effect of immunostimulation. The term "adjuvant" relates to compounds which prolongs or enhances or accelerates an immune response. Various mechanisms are possible in this respect, depending on the various types of adjuvants. For example, compounds which allow the maturation of the DC, e.g. lipopolysaccharides or CD40 ligand, form a first class of suitable adjuvants. Generally, any agent which influences the immune system of the type of a "danger signal" (LPS, GP96, dsRNA etc.) or cytokines, such as GM-CSF, can be used as an adjuvant which enables an immune response to be intensified and/or influenced in a controlled manner. CpG oligodeoxynucleotides can optionally also be used in this context, although their side effects which occur under certain circumstances, as explained above, are to be considered. Particularly preferred adjuvants are cytokines, such as monokines, lymphokines, interleukins or chemokines, e.g. IL-1, IL-2, IL-3, IL-4, IL-5, IL-6, IL-7, IL-8, IL-9, IL-10, IL-12, TNFα, INF-γ, GM-CSF, LT-α, or growth factors, e.g. hGH. Further known adjuvants are aluminium hydroxide, Freund's adjuvant or oil such as Montanide®, most preferred Montanide® ISA51. Lipopeptides, such as Pam3Cys, are also suitable for use as adjuvants in the pharmaceutical composition of the present invention.

Pharmaceutical compositions are usually provided in a uniform dosage form and may be prepared in a manner known per se. The pharmaceutical composition of the invention may e.g. be in the form of a solution or suspension.

The pharmaceutical composition of the invention may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may used for preparing pharmaceutically acceptable salts and are included in the invention. Pharmaceutically acceptable salts of this kind comprise in a non limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in the pharmaceutical composition of the invention include acetic acid in a salt, citric acid in a salt, boric acid in a salt and phosphoric acid in a salt.

Suitable preservatives for use in the pharmaceutical composition of the invention include benzalkonium chloride, chlorobutanol, paraben and thimerosal.

An injectible formulation may comprise a pharmaceutically acceptable excipient such as Ringer Lactate.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient" when used herein is intended to indicate all substances which may be present in a pharmaceutical composition of the present invention and which are not active ingredients such as, e.g., carriers, binders, lubricants, thickeners, surface active agents, preservatives, emulsifiers, buffers, flavoring agents, or colorants.

The agents and compositions described herein may be administered via any conventional route, such as by parenteral administration including by injection or infusion. Administration is preferably parenterally, e.g. intravenously, intraarterially, subcutaneously, intradermally or intramuscularly.

The term "parenteral administration" refers to the administration in a manner other than through the digestive tract, as by intravenous or intramuscular injection. Systemic administration is a route of administration that is either enteral, i.e. administration that involves absorption through the gastrointestinal tract, or parenteral.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The present invention is described in detail by the figures and examples below, which are used only for illustration purposes and are not meant to be limiting. Owing to the description and the examples, further embodiments which are likewise included in the invention are accessible to the skilled worker.

FIGURES

FIG. 1: Size of F4/RNA lipoplexes at different DOTMA/RNA charge ratios (2/1, 1/1, 1/2, 1/4) in water (a), PBS (b) and in PBS after addition of 2.2 mM $CaCl_2$ (c) and 22 mM $CaCl_2$ (d).

Figure 2:
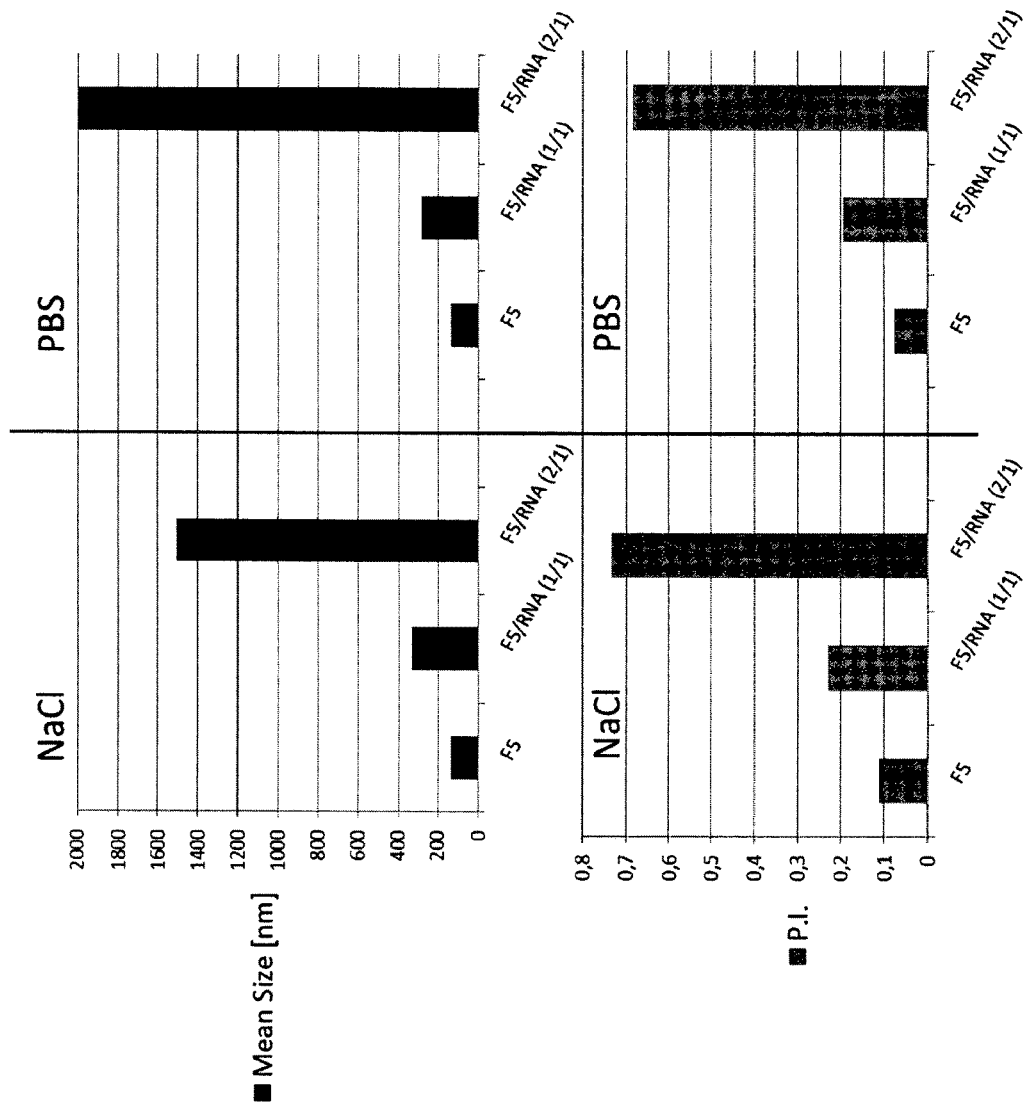

FIG. 2: Particle sizes of DOTMA/Chol liposomes (F5) and lipoplexes at different buffers and DOTMA/RNA charge ratios 1/1 and 2/1 (positive excess).

Figure 3:
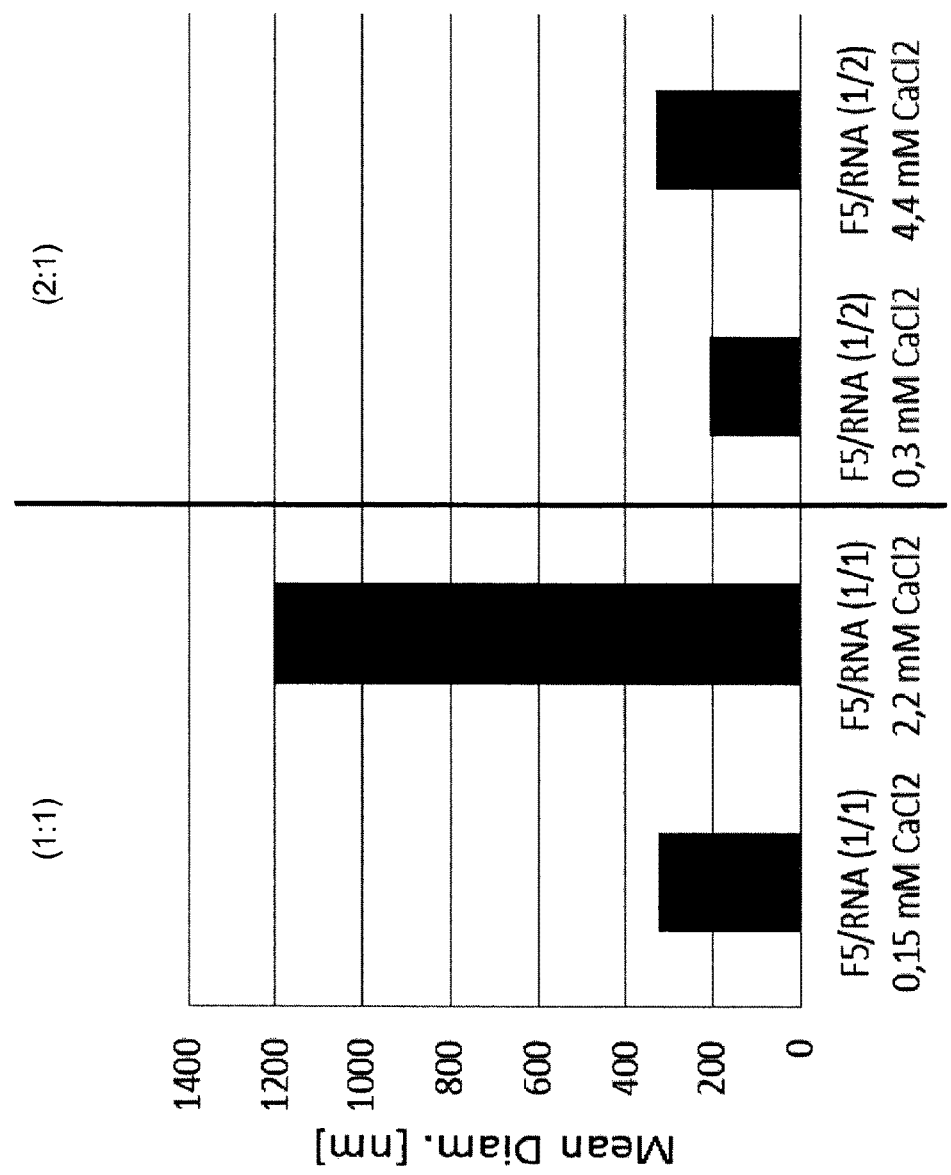

FIG. 3: Mean size of F5/RNA lipoplexes at charge ratios (1/1) and (1/2) after compaction of RNA using different amounts of $CaCl_2$.

Figure 4:
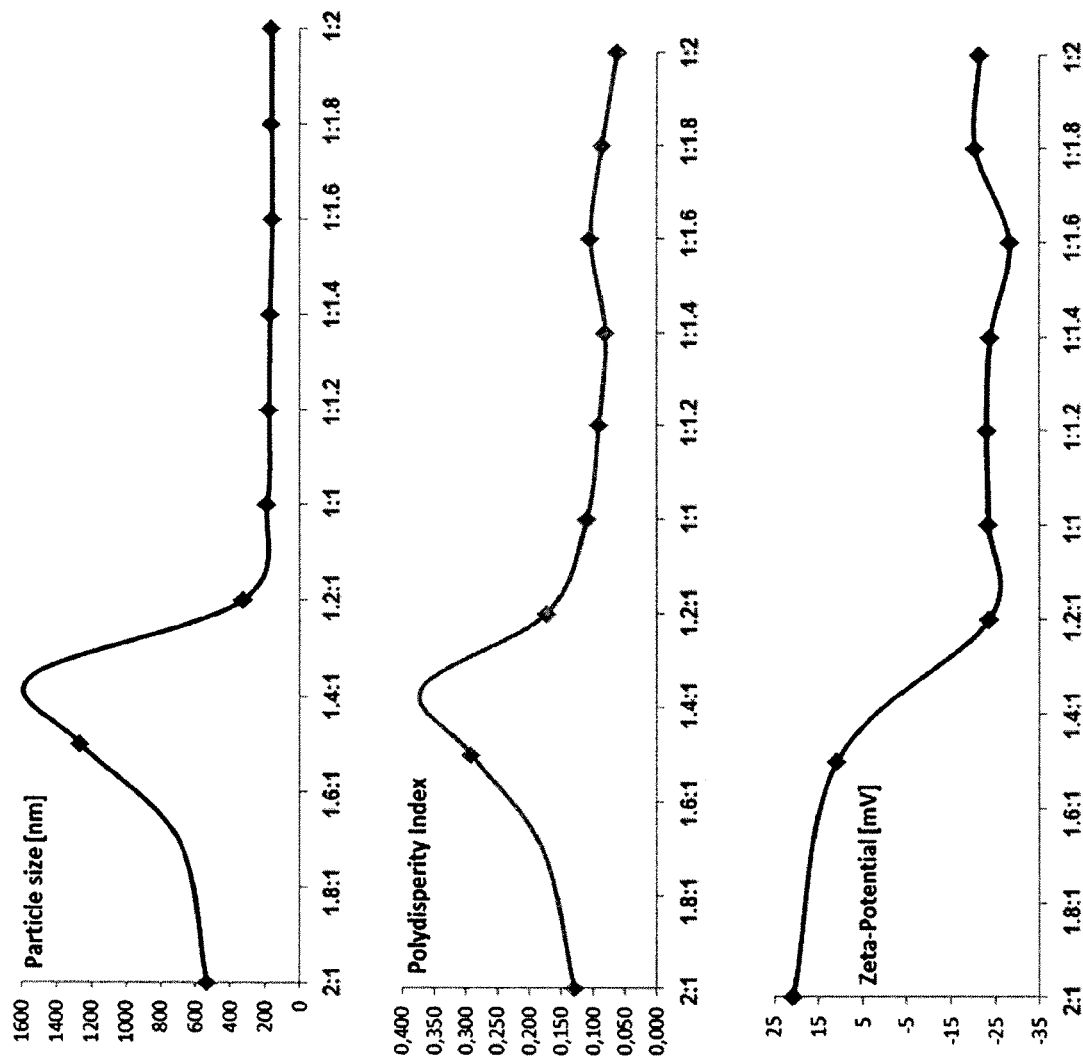

FIG. 4: Overview of selected results from physico-chemical characterization of RNA lipoplexes with DOTMA/DOPE liposomes. The x-axis gives the charge ratio between DOTMA and RNA. Top: particle size from PCS measurements, middle: polydispersity index, bottom: zeta potentials of the same formulations. The lines have been introduced to guide the eye.

Figure 5:
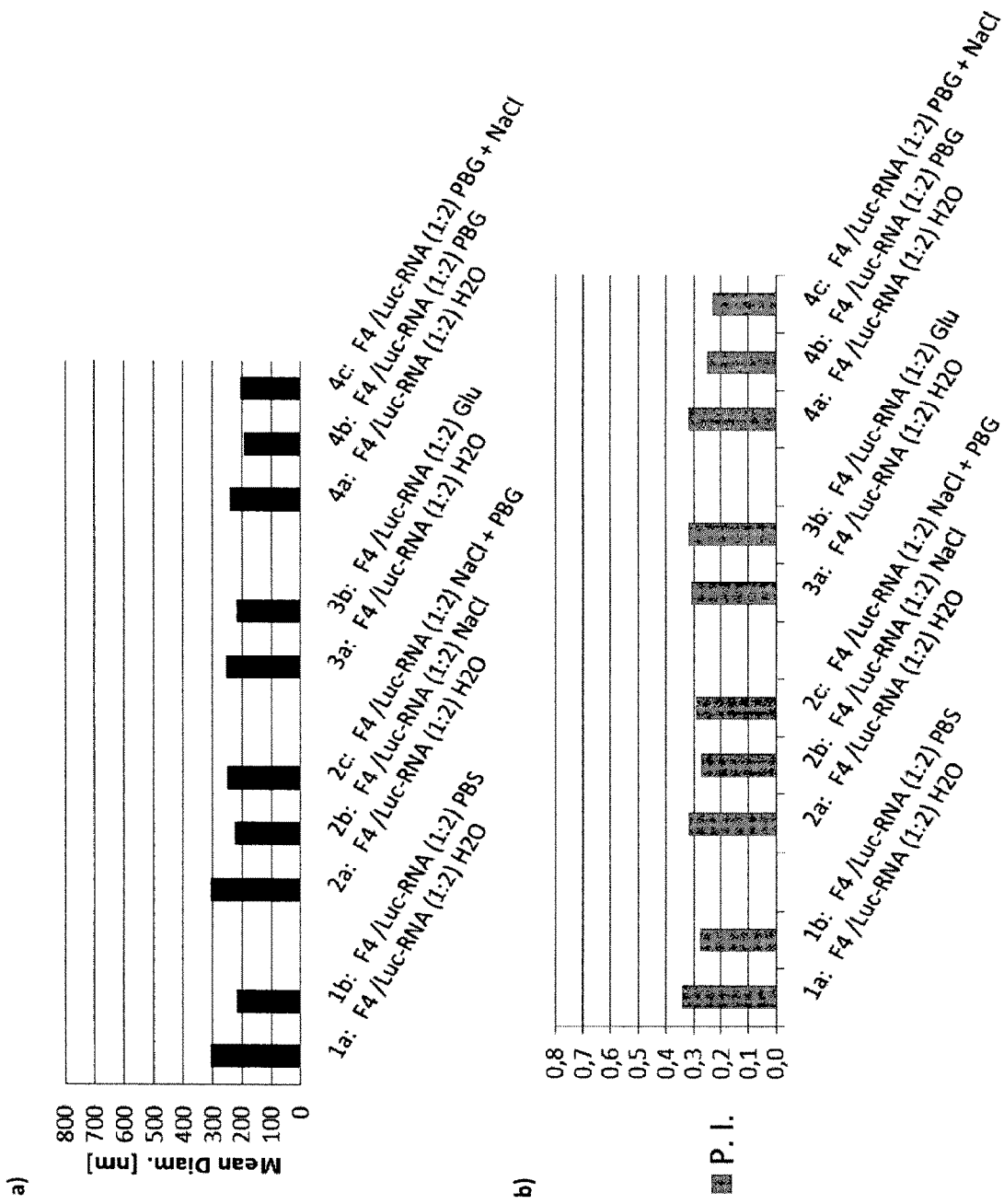

FIG. 5: (a) Mean size of F4/Luc-RNA lipoplexes at the charge ratio (1/2) in water and after addition of concentrated buffer to PBS (1×), sodium chloride (150 mM), glucose (5%) or phosphate buffered glucose. In contrast to the 1/1-ratio, which leads to aggregation under all buffer conditions (not shown here), the particle sizes of the lipoplexes at the 1/2 ratio were approximately 220 nm. (b) Polydispersity of size ranged from 0.23 to 0.34 indicating colloidal stability.

Figure 6:
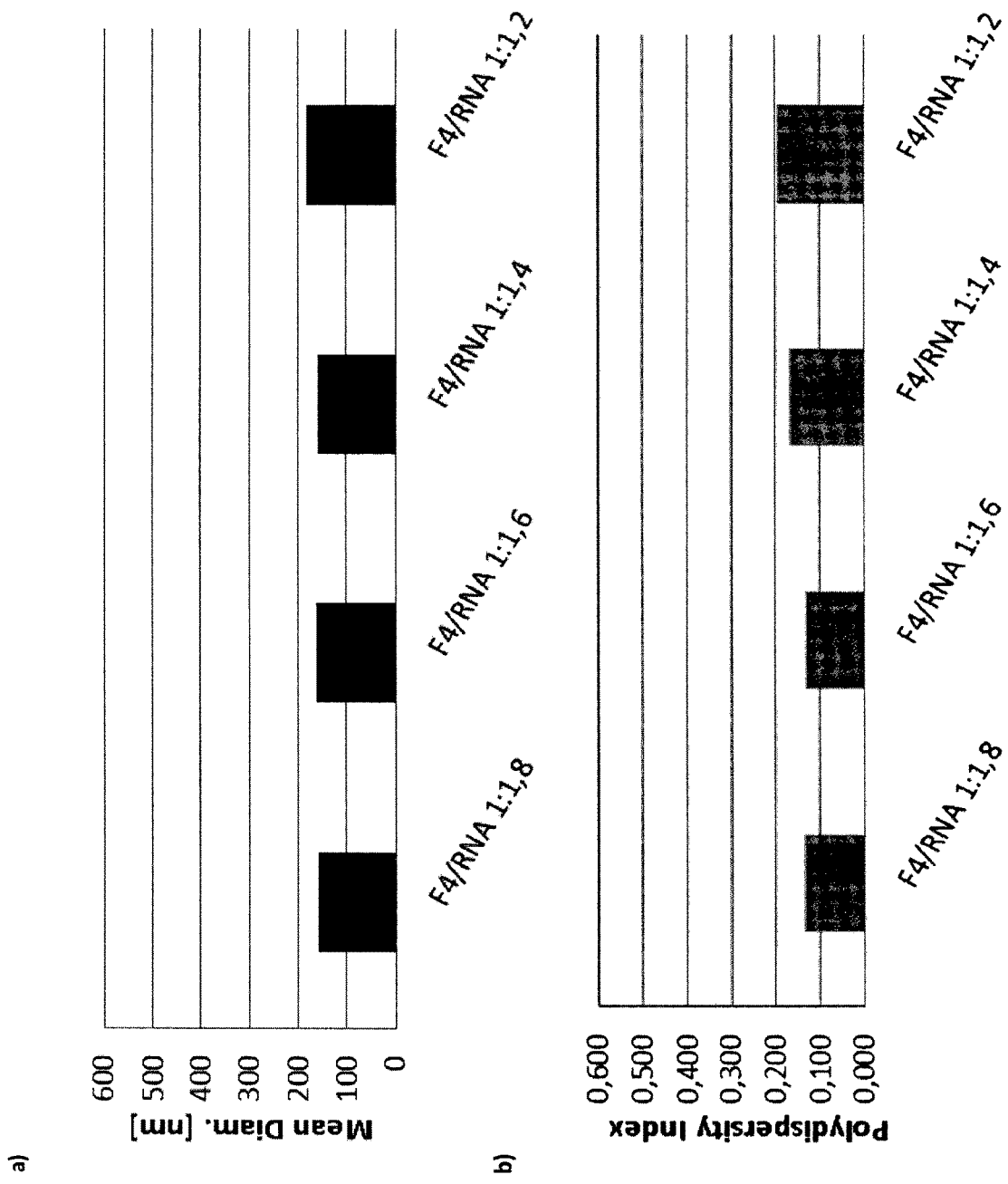

FIG. 6: (a) Mean size of F4/RNA lipoplexes at selected DOTMA/RNA charge ratios. Particle sizes of lipoplexes with charge ratios between 1:1.8 and 1:1.4 were approximately 160 nm. With decreasing negative excess (charge ratio 1:1.2) particle size was determined to 183 nm. (b) All tested charge ratios leads to lipoplexes with small polydispersity indices less than 0.2.

Figure 7:
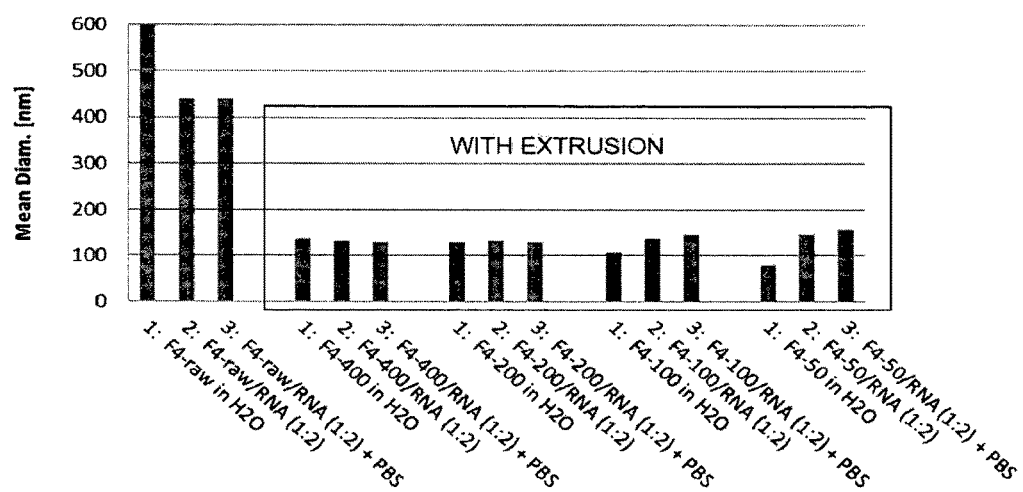
Figure 7:
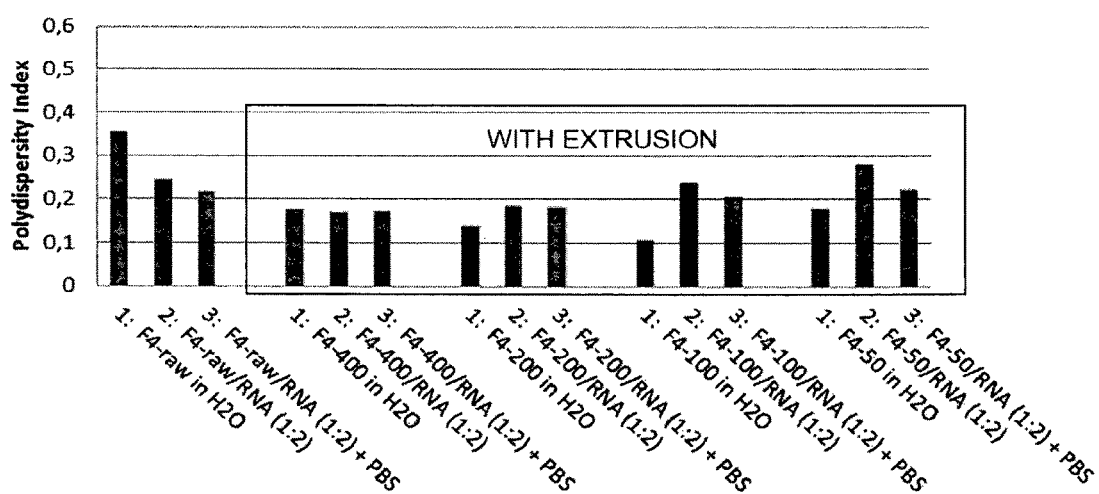

FIG. 7: (a) Mean Size of DOTMA/DOPE liposomes (1:2) in water without extrusion (F4-raw), after extrusion using a polycarbonate membrane with a pore diam. of 400 nm (F4-400), 200 nm (F4-200), 100 nm (F4-100) or 50 nm (F4-50). Corresponding lipoplexes with a DOTMA/RNA charge ratio of 1/2 in water (2:) and in PBS buffer (3:). (b) Polydispersity of size of the lipoplexes with extruded liposomes ranged from 0.10 to 0.28. However, lipoplexes formed by un-extruded liposomes also showed a sufficiently narrow size distribution.

Figure 8:
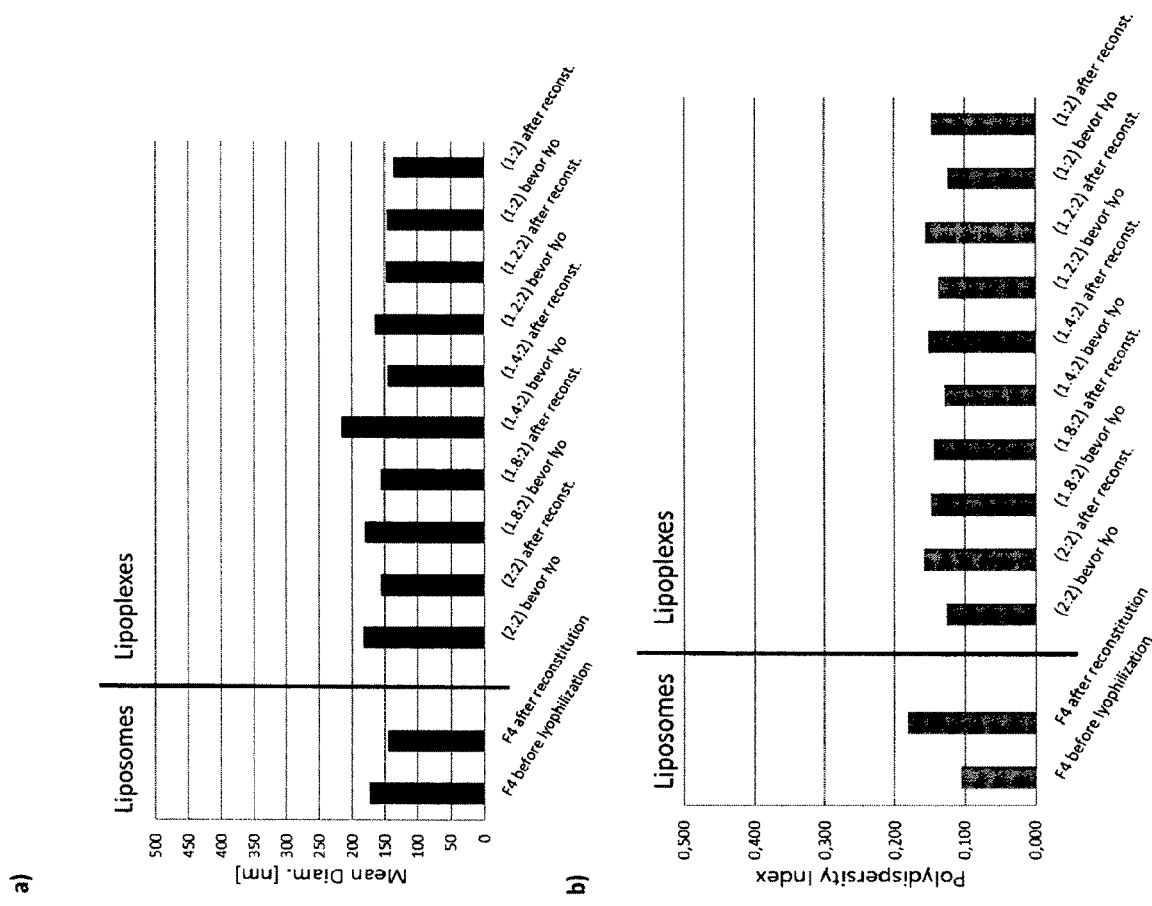

FIG. 8: Mean size (a) and Polydispersity Index (b) of DOTMA/DOPE liposomes (F4) determined before lyophilization and after lyophilization and reconstitution using water.

Figure 9:
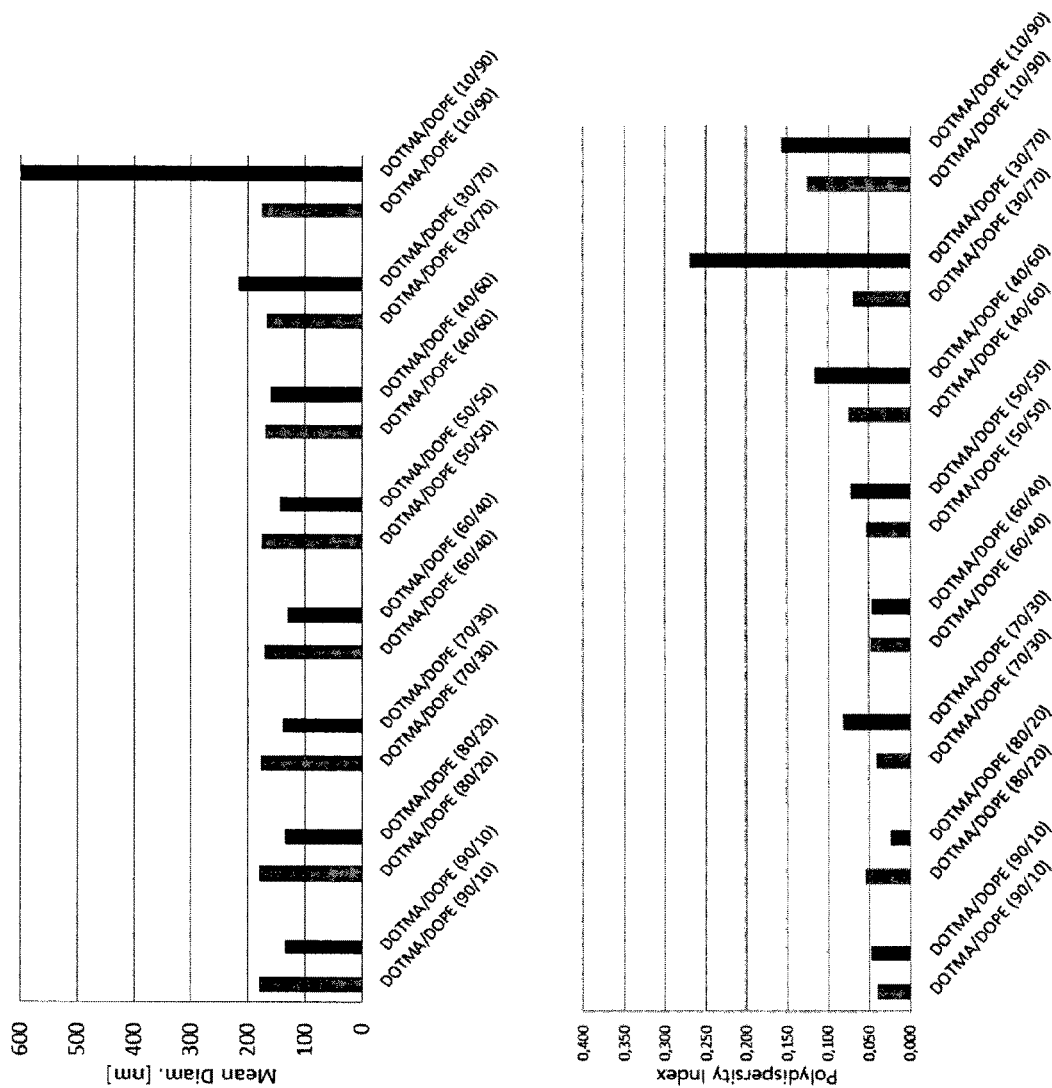

FIG. 9: Particle size of liposomes with different DOTMA/DOPE ratios. For liposomes with high DOPE (90%) fraction, the particles are unstable in PBS and aggregate.

Figure 10:
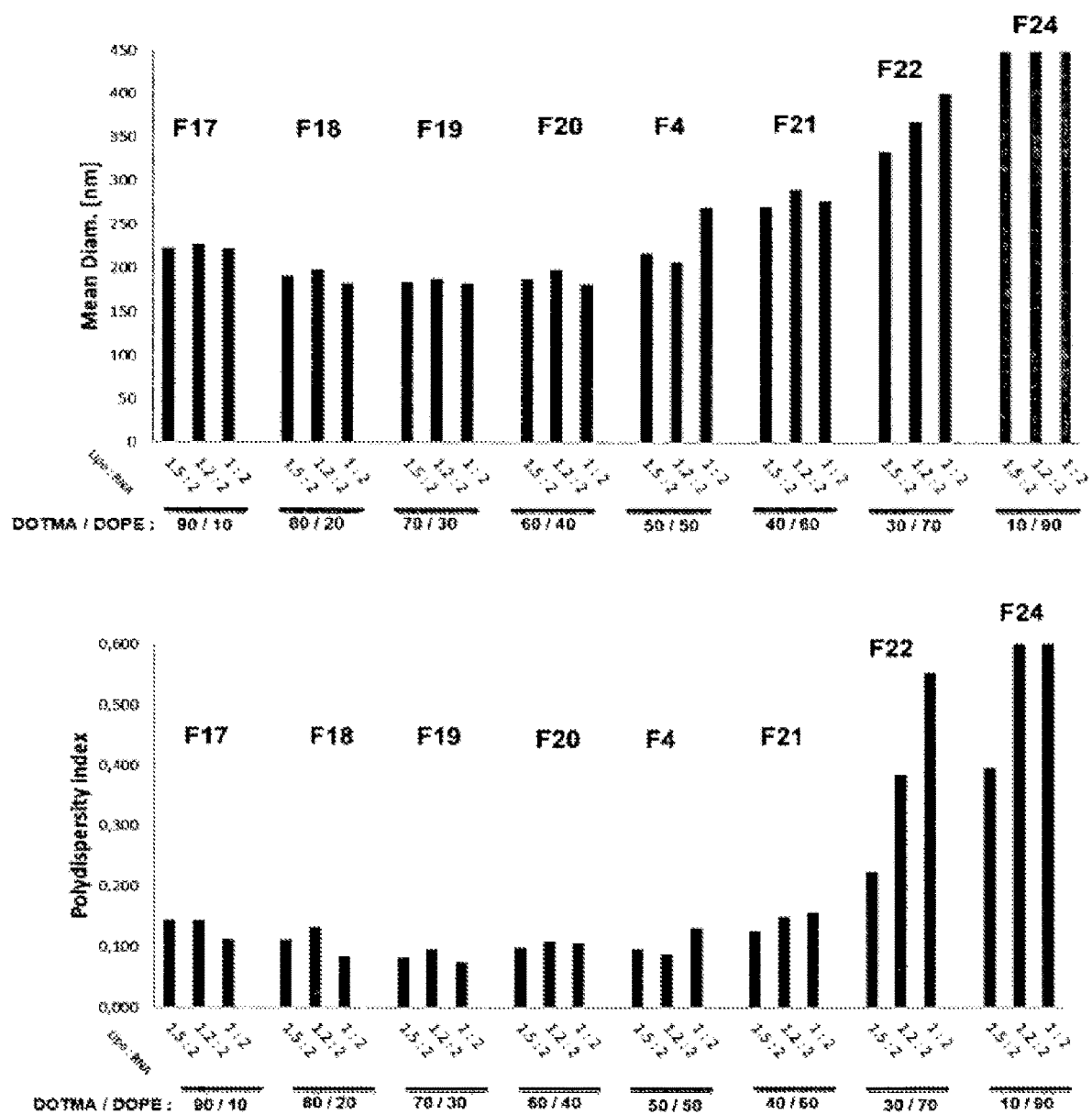

FIG. 10: Particle size of lipoplexes with liposomes comprising different DOTMA/DOPE ratios. With the DOTMA/DOPE ratio from 9/1 to 4/6, the lipoplexes have defined particle sizes (<300 nm) with low PI values (<0.2). With higher DOPE fraction, larger particle sizes with high PI values are obtained.

Figure 11:
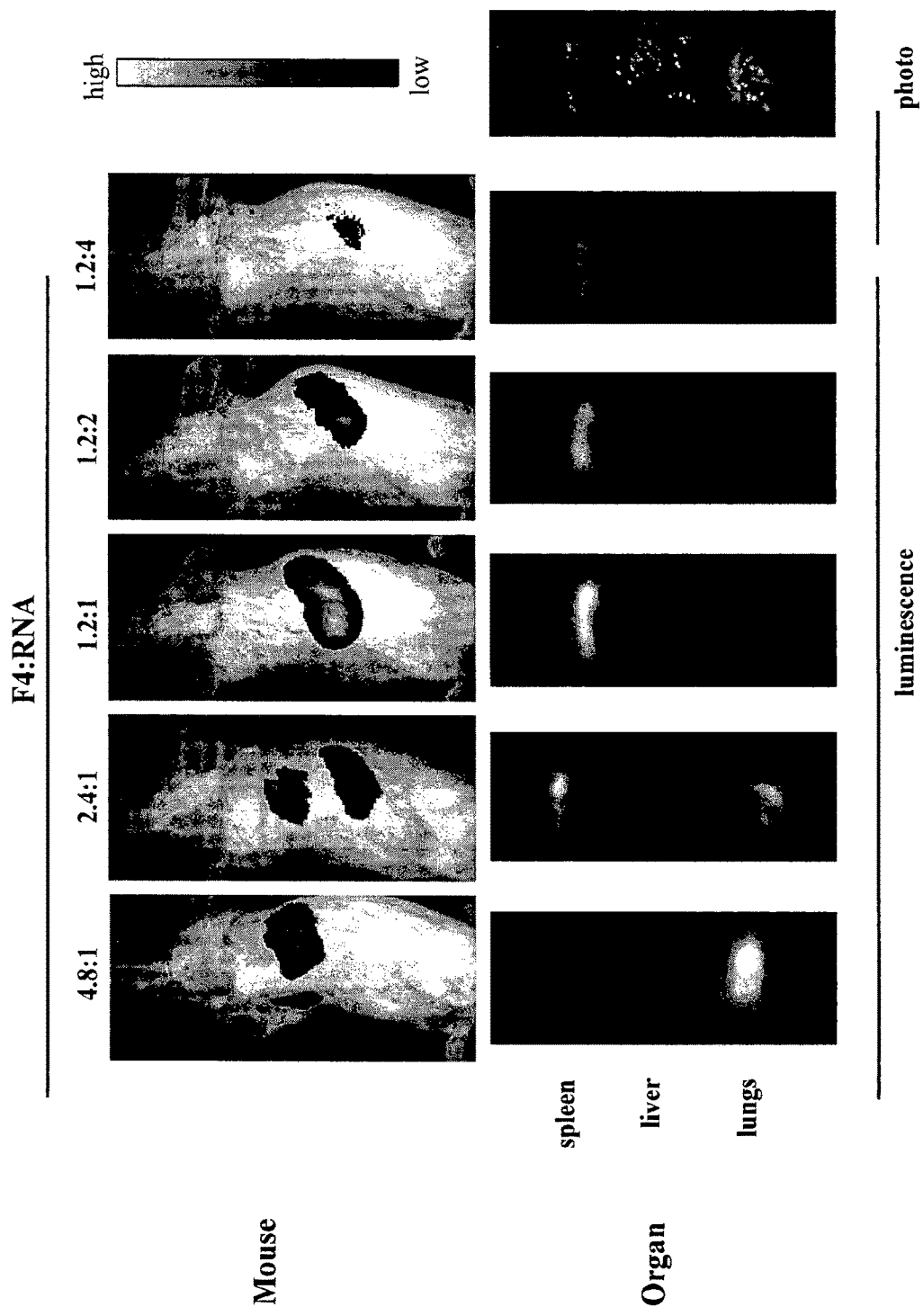

FIG. 11: Luciferase activities in vivo and ex vivo after injection into BALB/c mice of luciferase-RNA (20 µg) complexed with different amounts of F4 liposomes to yield F4:RNA ratios of 4.8:1, 2.4:1, 1.2:1, 1.2:2, 1.2:4.

Figure 12:
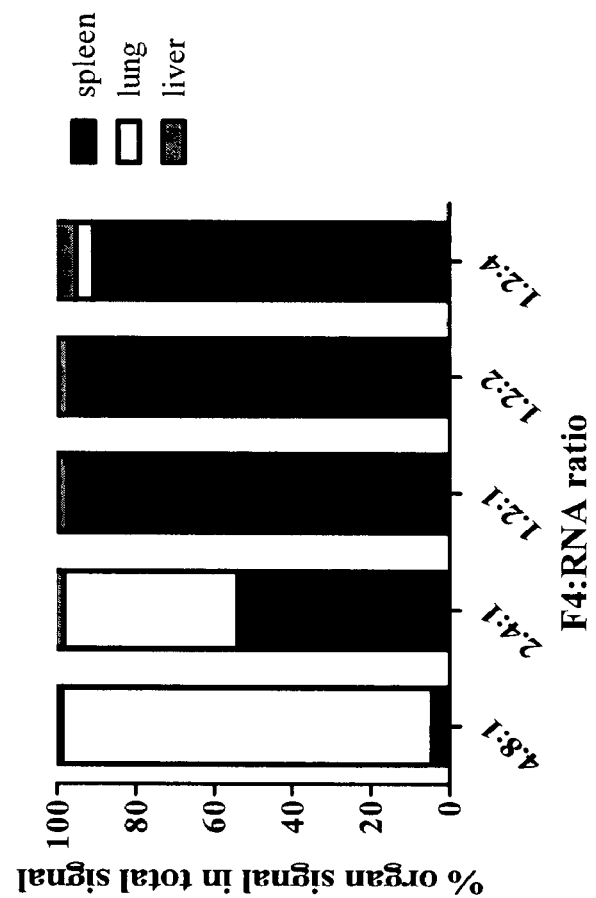

FIG. 12: Distribution of total luciferase signal among organs derived from the experiment depicted in FIG. 11.

Figure 13:
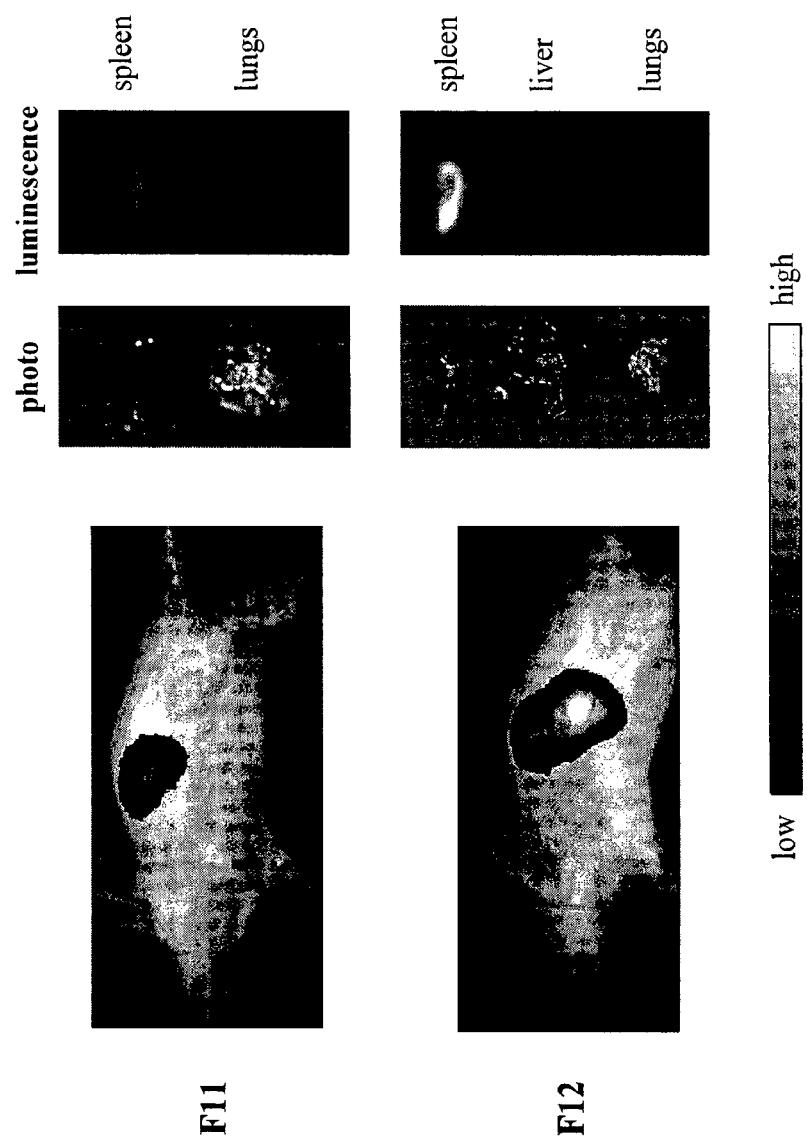

FIG. 13: Luciferase activities in vivo and ex vivo after injection into BALB/c mice of Luciferase-RNA (20 µg) complexed with F11 or F12 liposomes.

Figure 14:
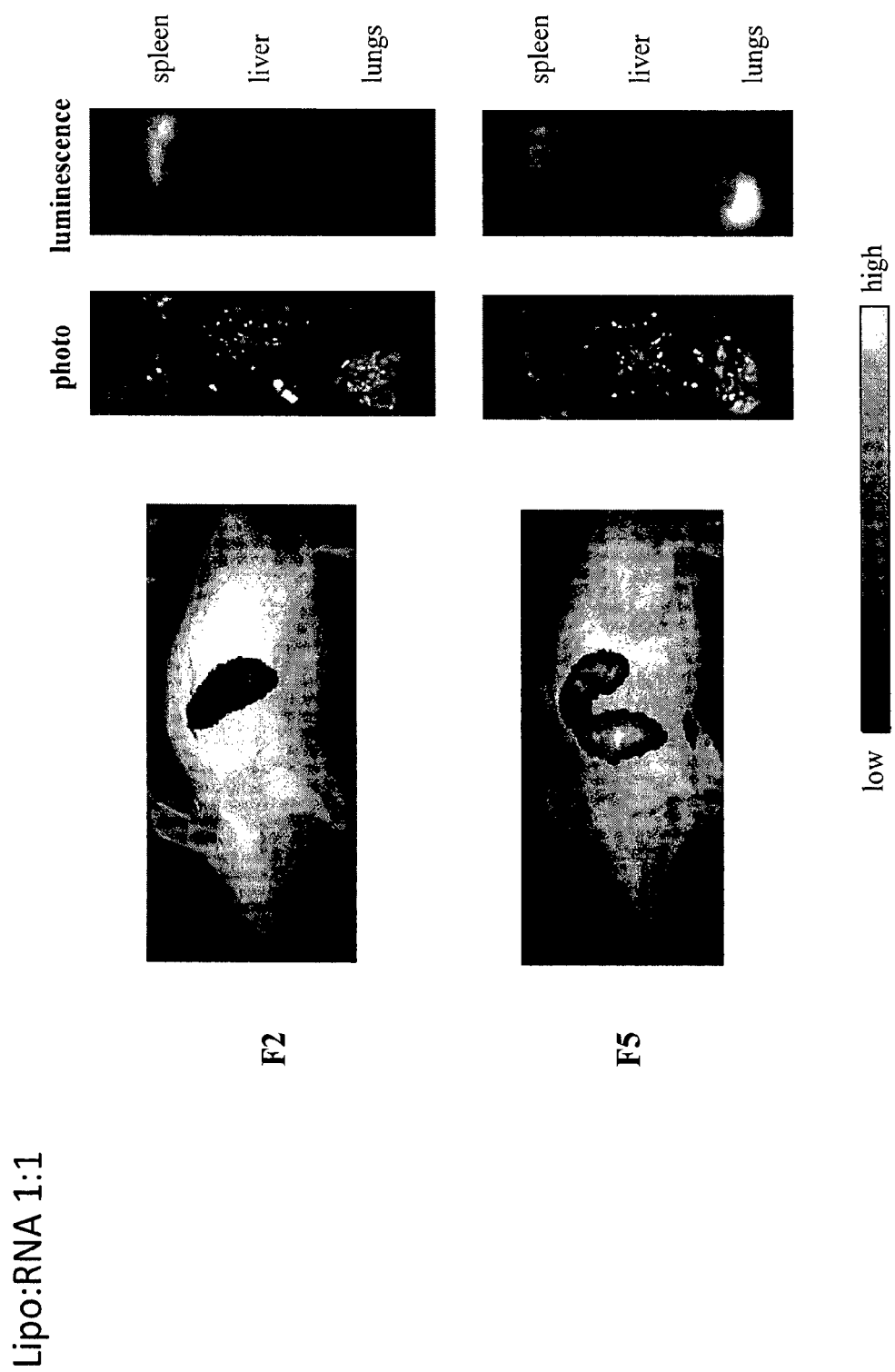

FIG. 14: Luciferase activities in vivo and ex vivo after injection into BALB/c mice of Luciferase-RNA (20 µg) complexed with F2 or F5 liposomes.

Figure 15:
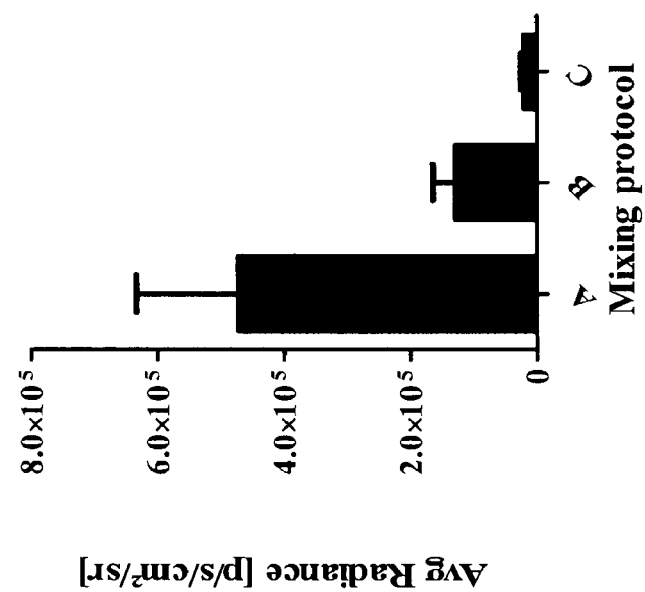

FIG. 15: Quantification of luciferase activities in spleens of mice after injection of Luciferase-RNA (20 µg) diluted in 1×PBS (A) or undiluted in water (B and C) complexed with F4 liposomes diluted in 1×PBS (B) or undiluted in water (A and C) with an F4:RNA ratio of 1.2:2. The final PBS concentrations of all complexes were set to 1×PBS.

Figure 16:
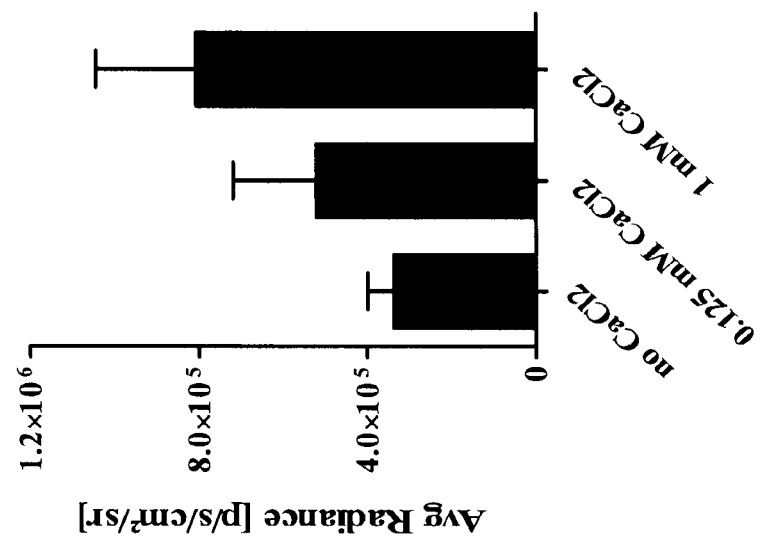

FIG. 16: Quantification of luciferase activities in spleens of mice after injection of Luciferase-RNA (20n) precomplexed with 0.125 or 1 mM $CaCl_2$ or without precomplexation and mixed with F4 liposomes with an F4:RNA ratio of 1.2:2.

Figure 17:
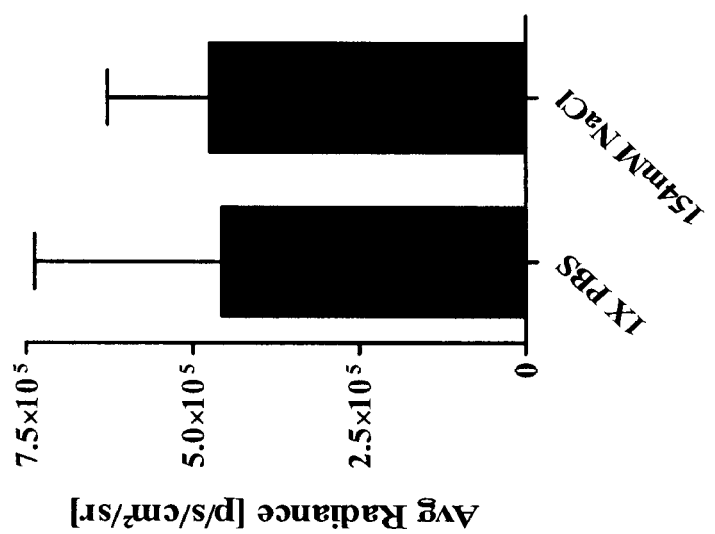

FIG. 17: Quantification of luciferase activities in spleens of mice after injection of Luciferase-RNA (20 µg) or F4 liposomes diluted in 1×PBS or 154 mM NaCl and mixed with an F4:RNA ratio of 1.2:2.

Figure 18:
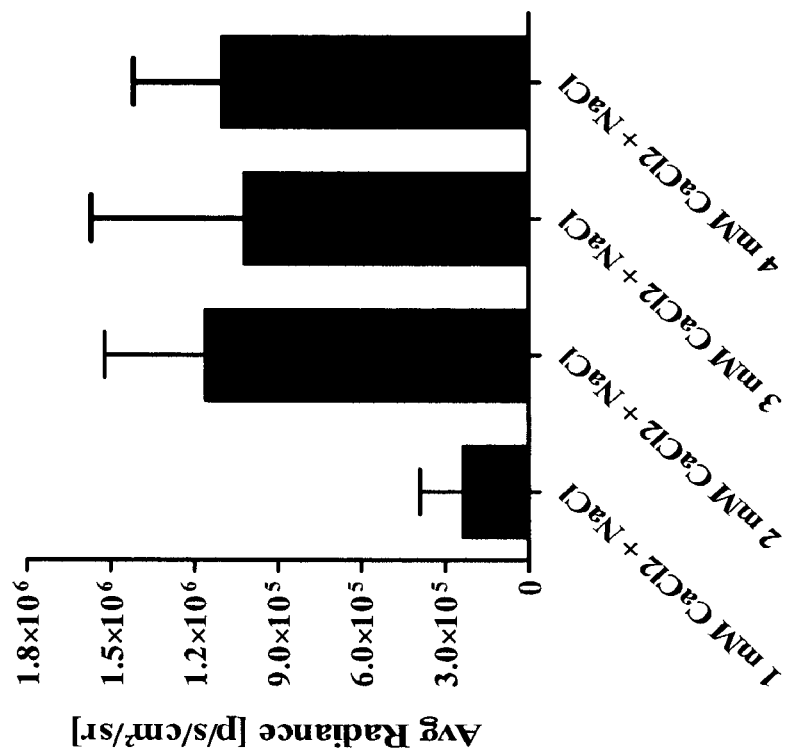

FIG. 18: Quantification of luciferase activities in spleens of mice after injection of Luciferase-RNA (20 µg) precomplexed with 1-4 mM $CaCl_2$ and mixed with F4 liposomes with an F4:RNA ratio of 1.2:2 using 154 mM NaCl instead of 1×PBS as dilution buffer.

Figure 19:
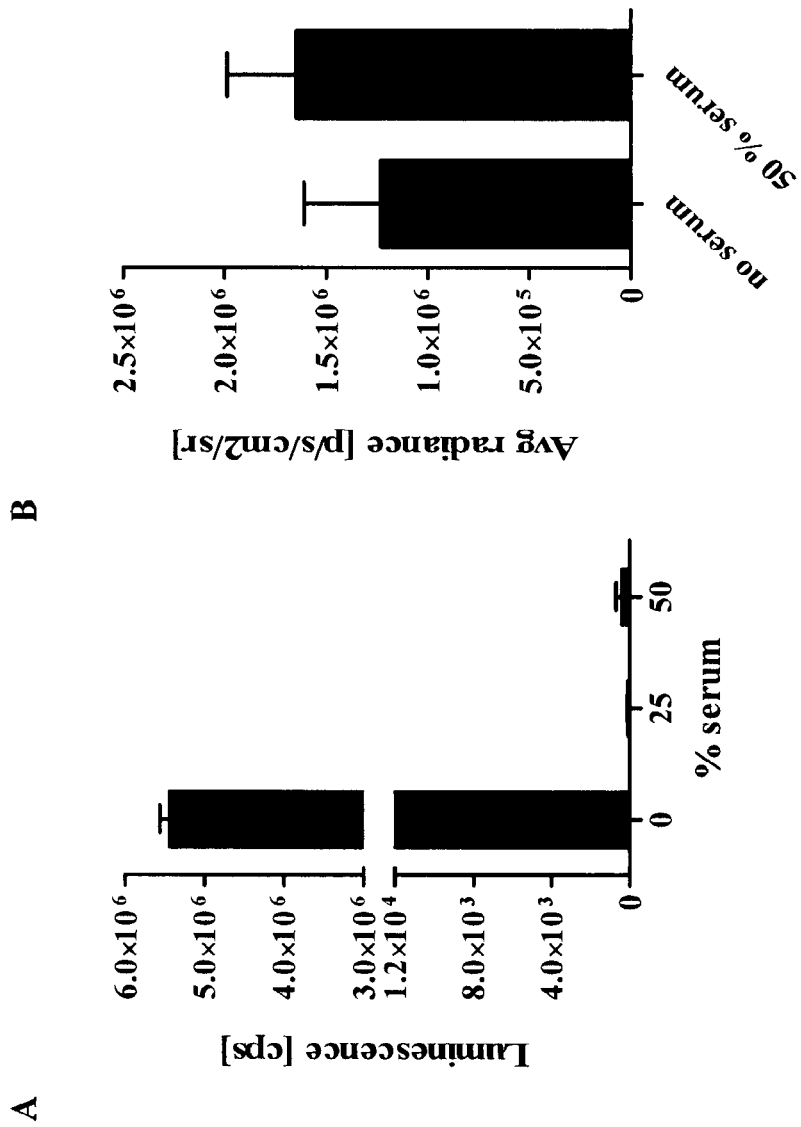

FIG. 19: (A) Luciferase-RNA (5 µg) was incubated in 25 or 50% mouse serum for 30 min. and then electroporated into human monocyte derived immature DCs. Luciferase activity was assessed 18 h later via standard in vitro luciferase assay. (B) Luciferase-RNA (20 µg) was complexed via standard protocol with F4 liposomes with an F4:RNA ratio of 1.2:2 and then incubated in the presence or absence of 50% mouse serum for 30 min. BALB/c mice were injected intravenously with these formulations and luciferase activities in vivo were quantified from spleens of mice.

Figure 20:
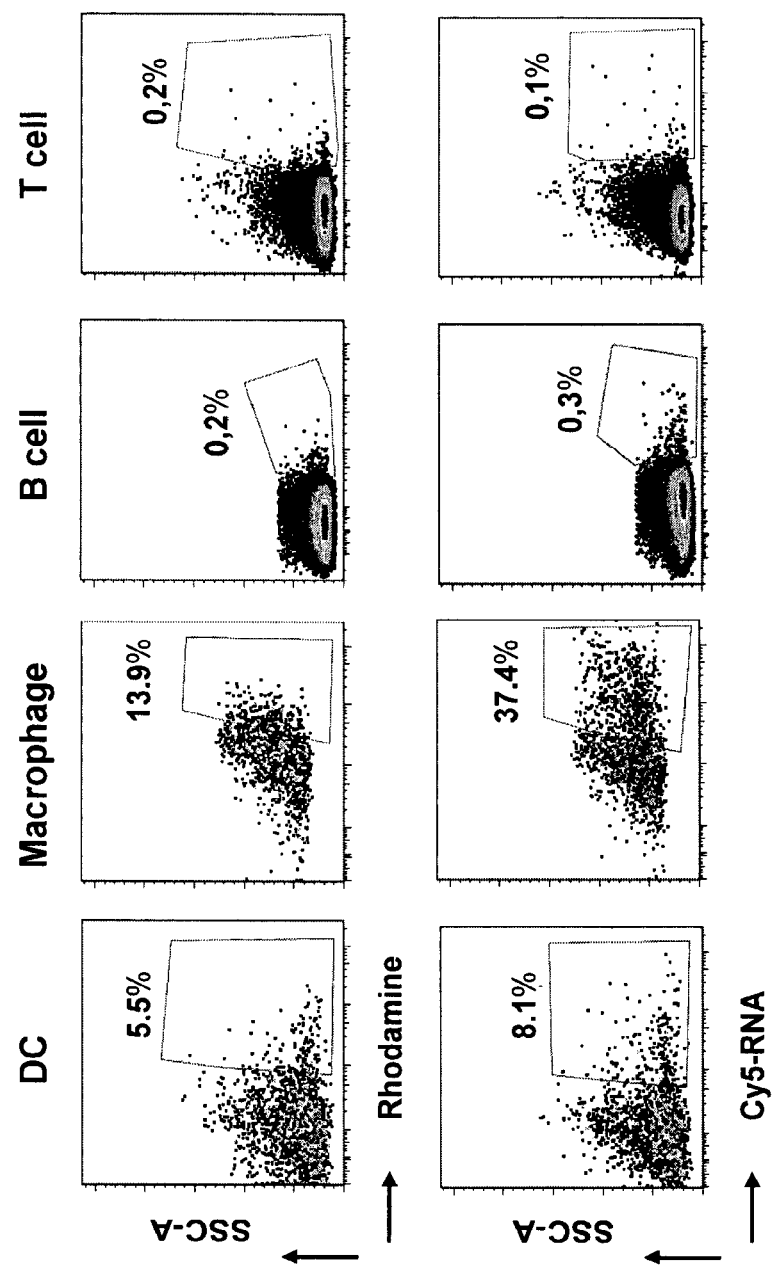

FIG. 20: Assessment of the uptake of Cy5-RNA or F4-rho by cell populations in spleen after injection into BALB/c mice of Cy5-RNA (40 µg) complexed with F4 liposomes labeled with Rhodamine (F4-rho) (1.2:2; Liposome:RNA).

Figure 21:
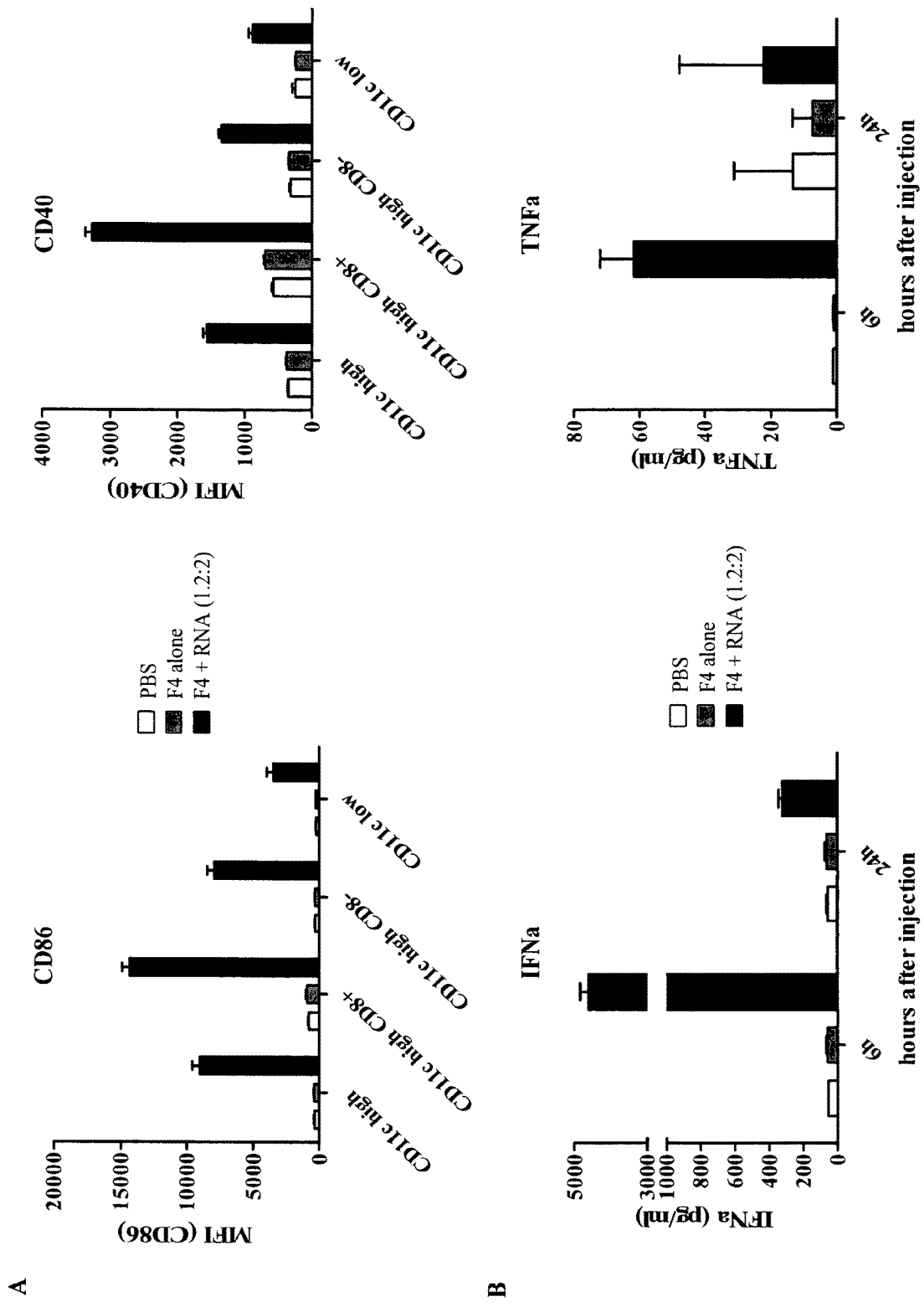

FIG. 21: Assessment of the (A) maturation status of dendritic cells (revealed by upregulation of CD86 and CD40) and (B) serum concentrations of IFNa and TNFa after injection into C57BL/6 mice of HA-RNA (40 µg) complexed with F4 (1.2:2; Liposome:RNA), F4 alone or PBS (as control).

Figure 22:
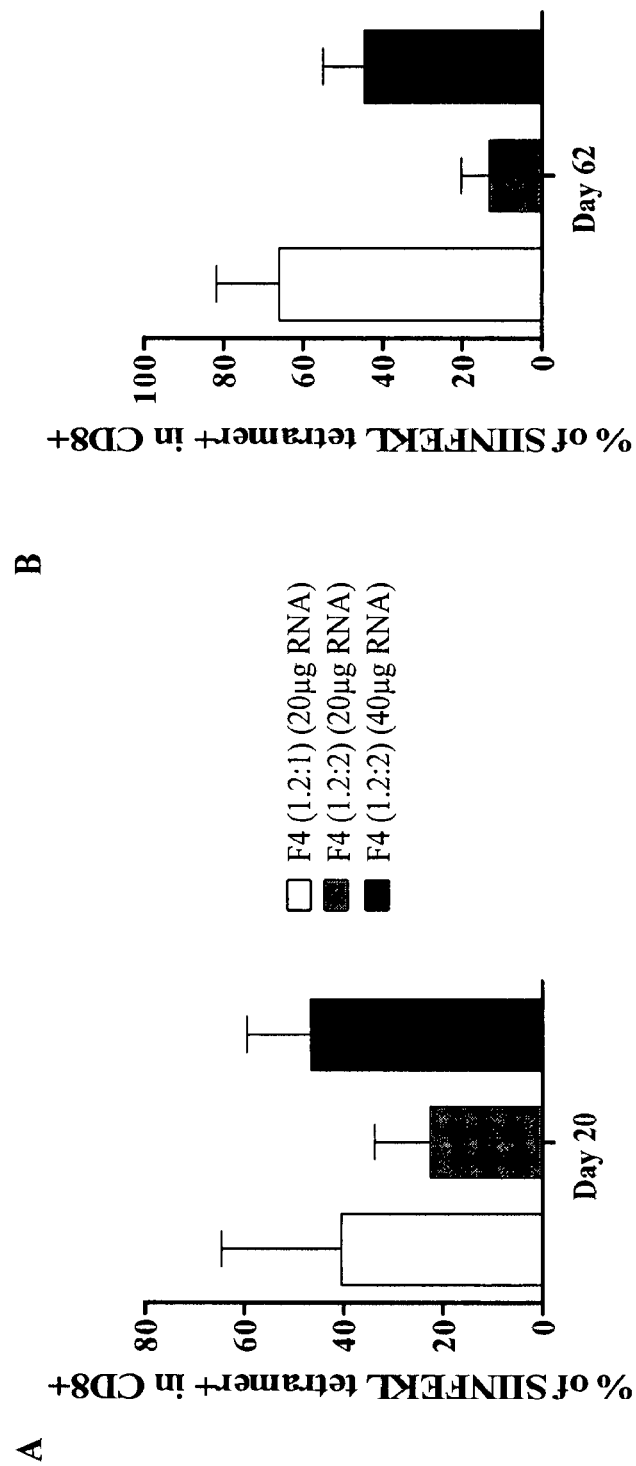

FIG. 22: Assessment of the (A) frequencies of antigen specific CD8+ T cells and (B) memory recall responses after immunization of C57BL/6 mice with SIINFEKL-RNA (20 or 40 µg) complexed with F4 liposomes at different liposome:RNA ratios.

Figure 23:
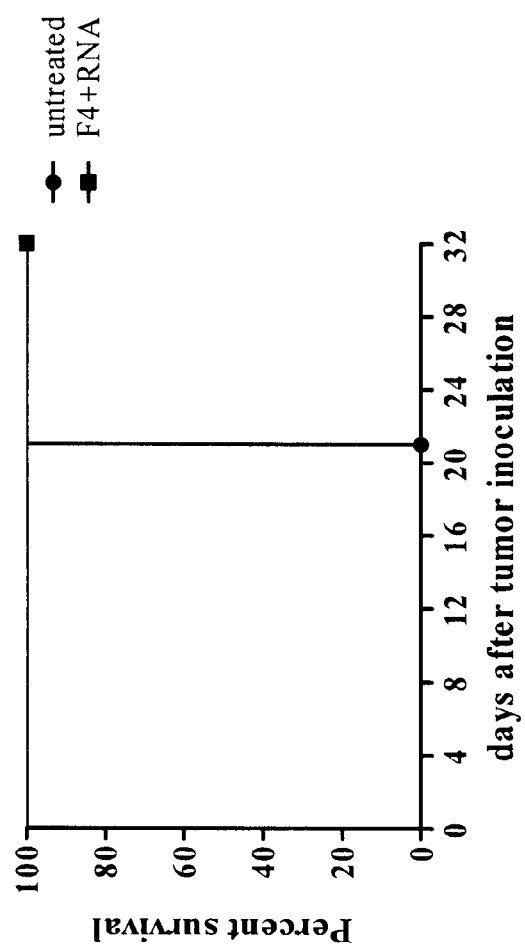

FIG. 23: Kaplan-Meier survival curves of C57BL/6 mice which received three intravenous immunizations of SIINFEKL-RNA (40 µg) complexed with F4 liposomes with an F4:RNA ratio of 1.2:2 or were left untreated and into which were injected 2×10$^5$ B16-OVA tumor cells s.c. into the flanks.

Figure 24:
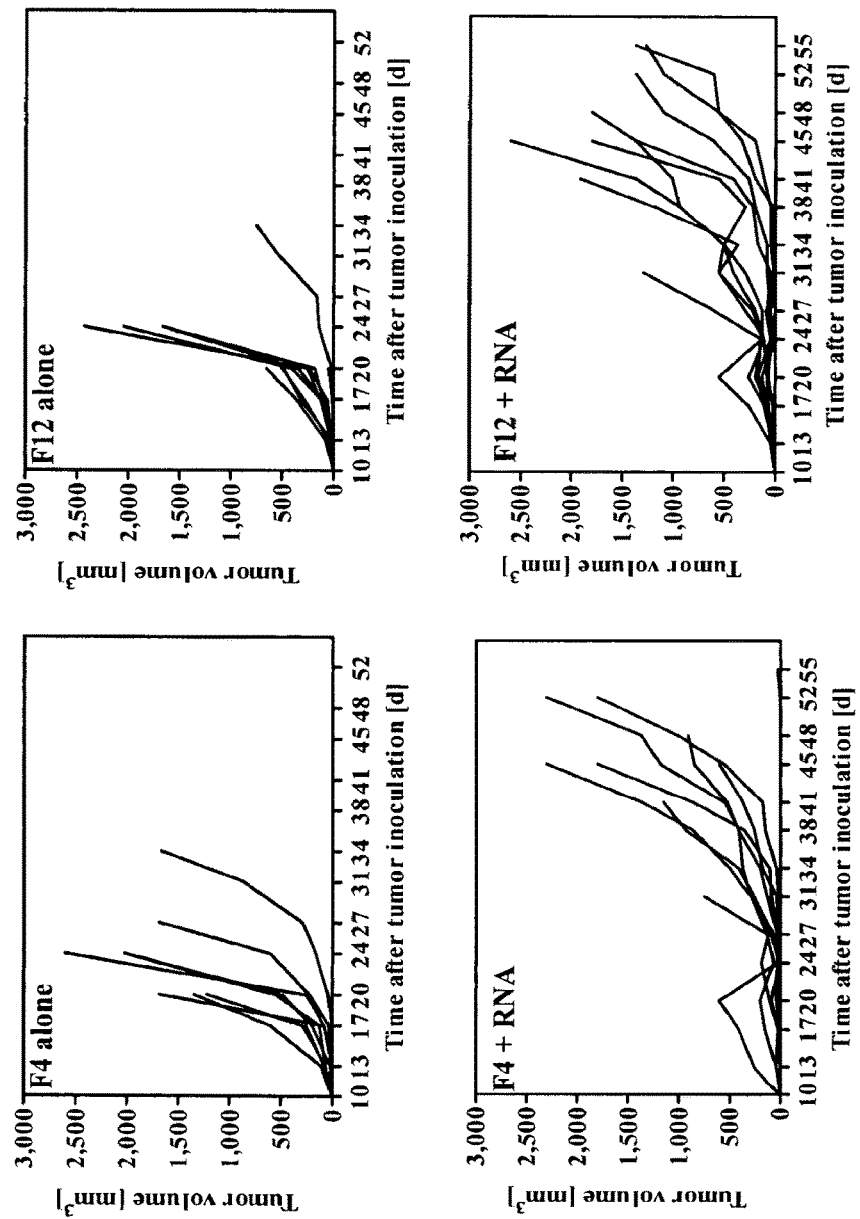

FIG. 24: Individual tumor growth after s.c. inoculation of 2×10$^5$B16-OVA tumor cells into the flanks of C57/Bl6 mice which received seven intravenous immunizations of SIINFEKL-RNA (40 µg) complexed with F4 or F12 liposomes with an F4:RNA ratio of 1.2:2. Liposomes alone without SIINFEKL-RNA were used as control treatment.

Figure 25:
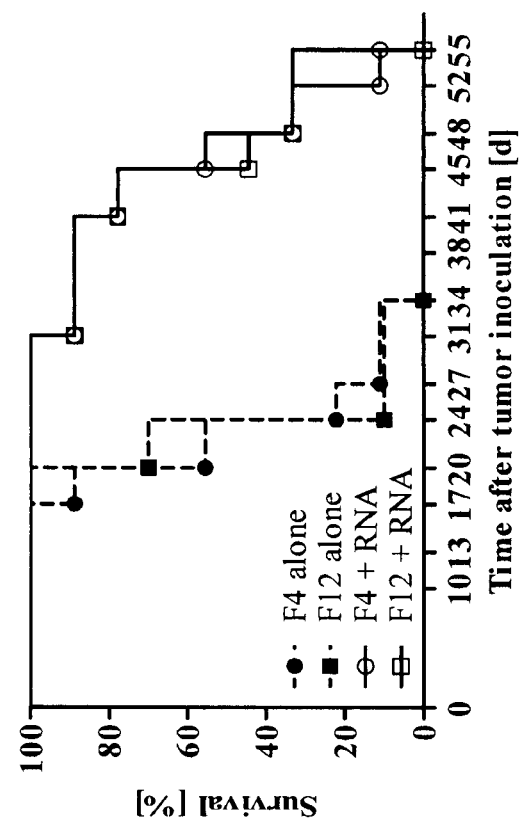

FIG. 25: Kaplan-Meier survival curves after s.c. inoculation of 2×10$^5$ B16-OVA tumor cells into the flanks of C57/Bl6 mice which received seven intravenous immunizations of SIINFEKL-RNA (40 µg) complexed with F4 or F12 liposomes with an F4:RNA ratio of 1.2:2. Liposomes alone without SIINFEKL-RNA were used as control treatment.

Figure 26:
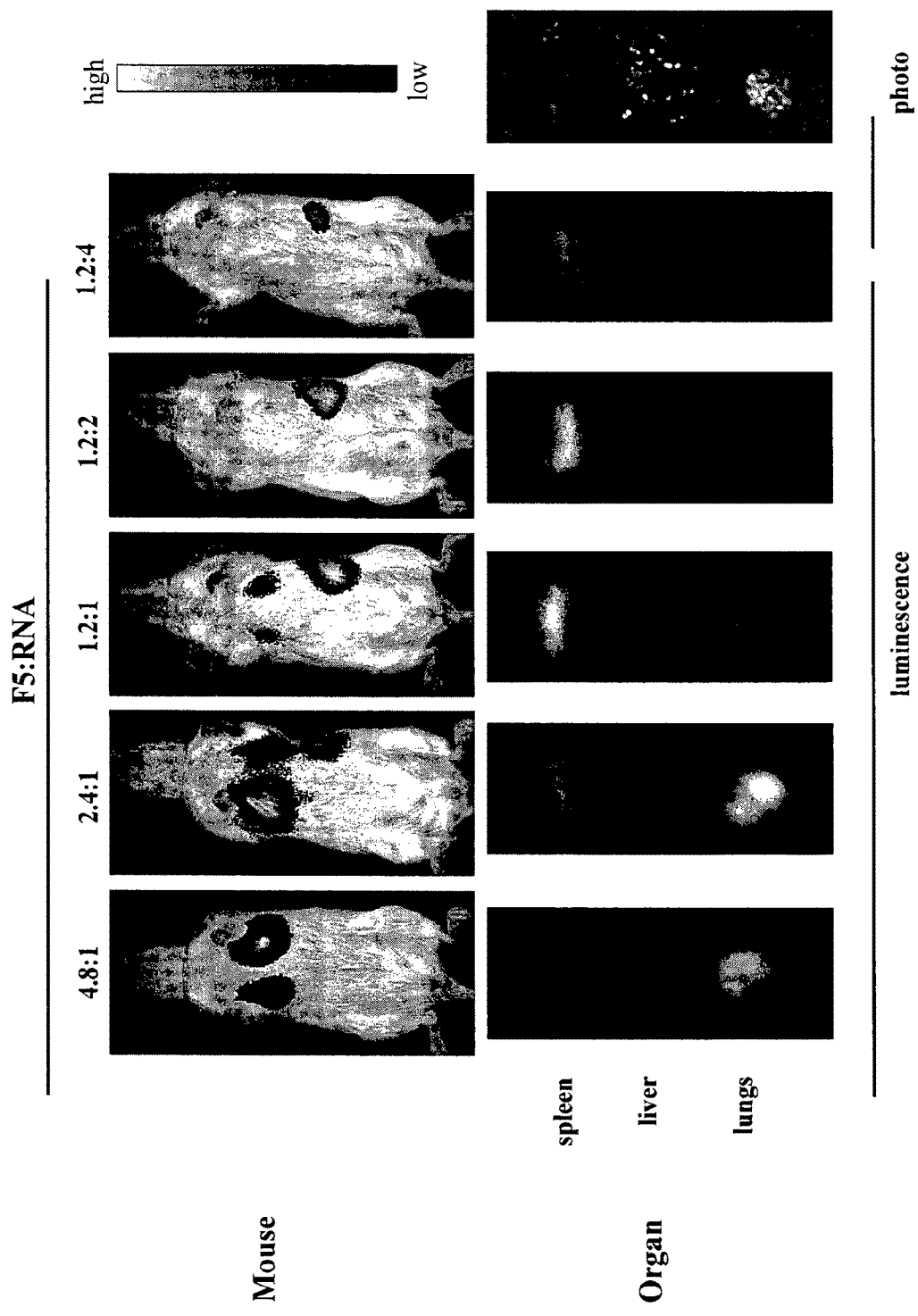

FIG. 26: Luciferase activities in vivo and ex vivo after injection into BALB/c mice of luciferase-RNA (20 µg) complexed with different amounts of F5 liposomes to yield F5:RNA ratios of 4.8:1, 2.4:1, 1.2:1, 1.2:2, 1.2:4.

Figure 27:
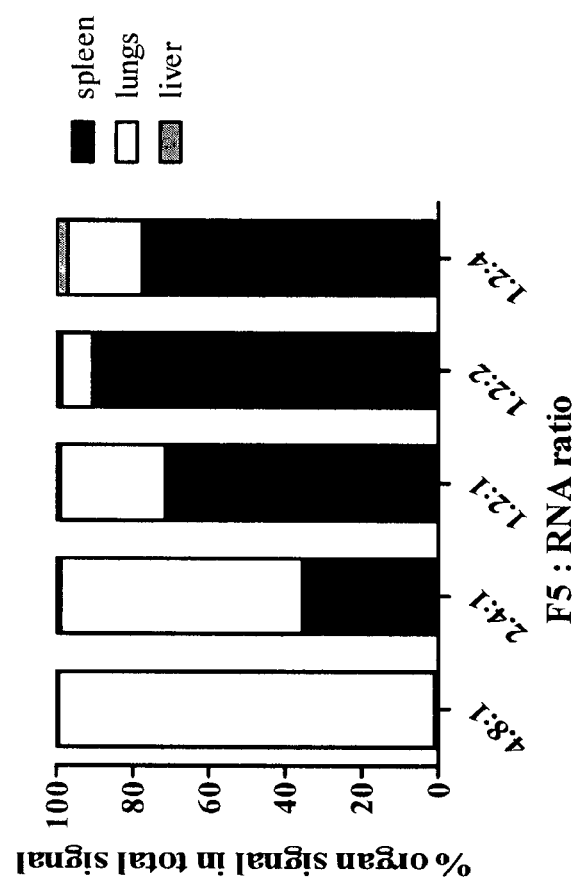

FIG. 27: Distribution of total luciferase signal among organs derived from the experiment depicted in FIG. 26.

Figure 28:
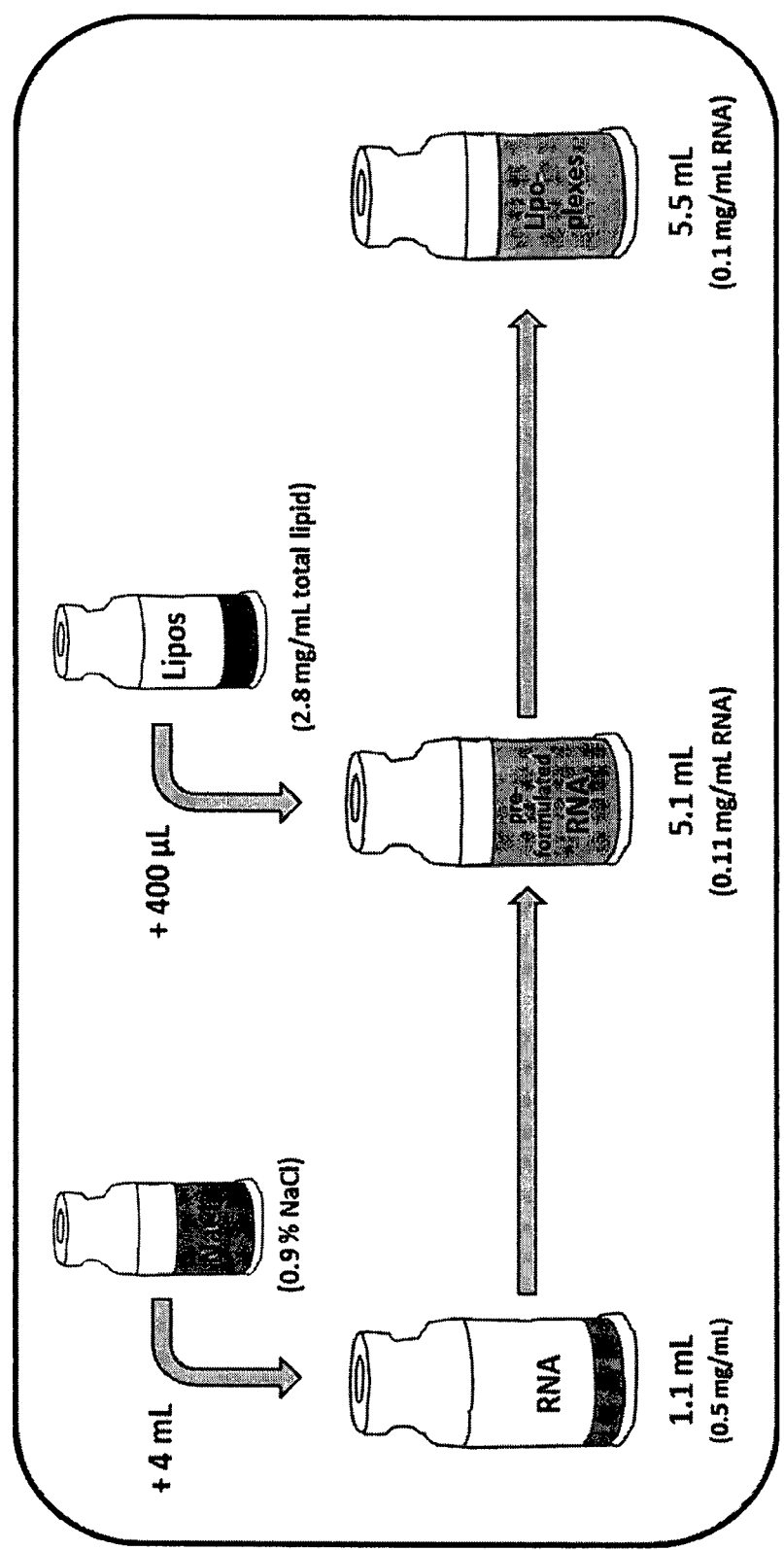

FIG. 28: Preformulation of RNA and reconstitution of RNA-lipoplex solution.

Figure 29:
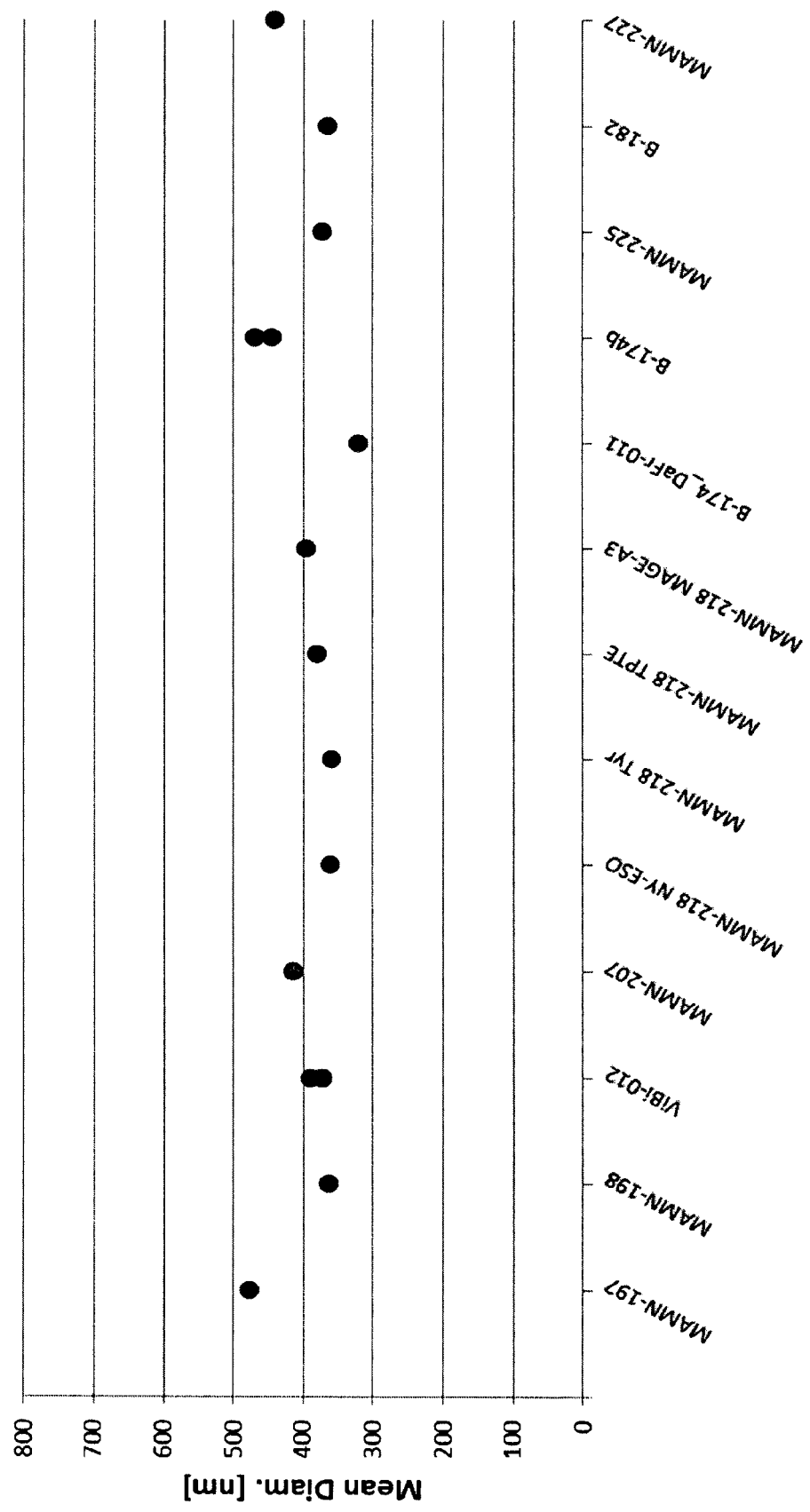

FIG. 29: Results of DLS measurements of RNA lipoplexes reconstituted according the clinical formulation protocol. Limited spread of received lipoplex particle sizes demonstrates the robustness of the procedure of mixing.

Figure 30:
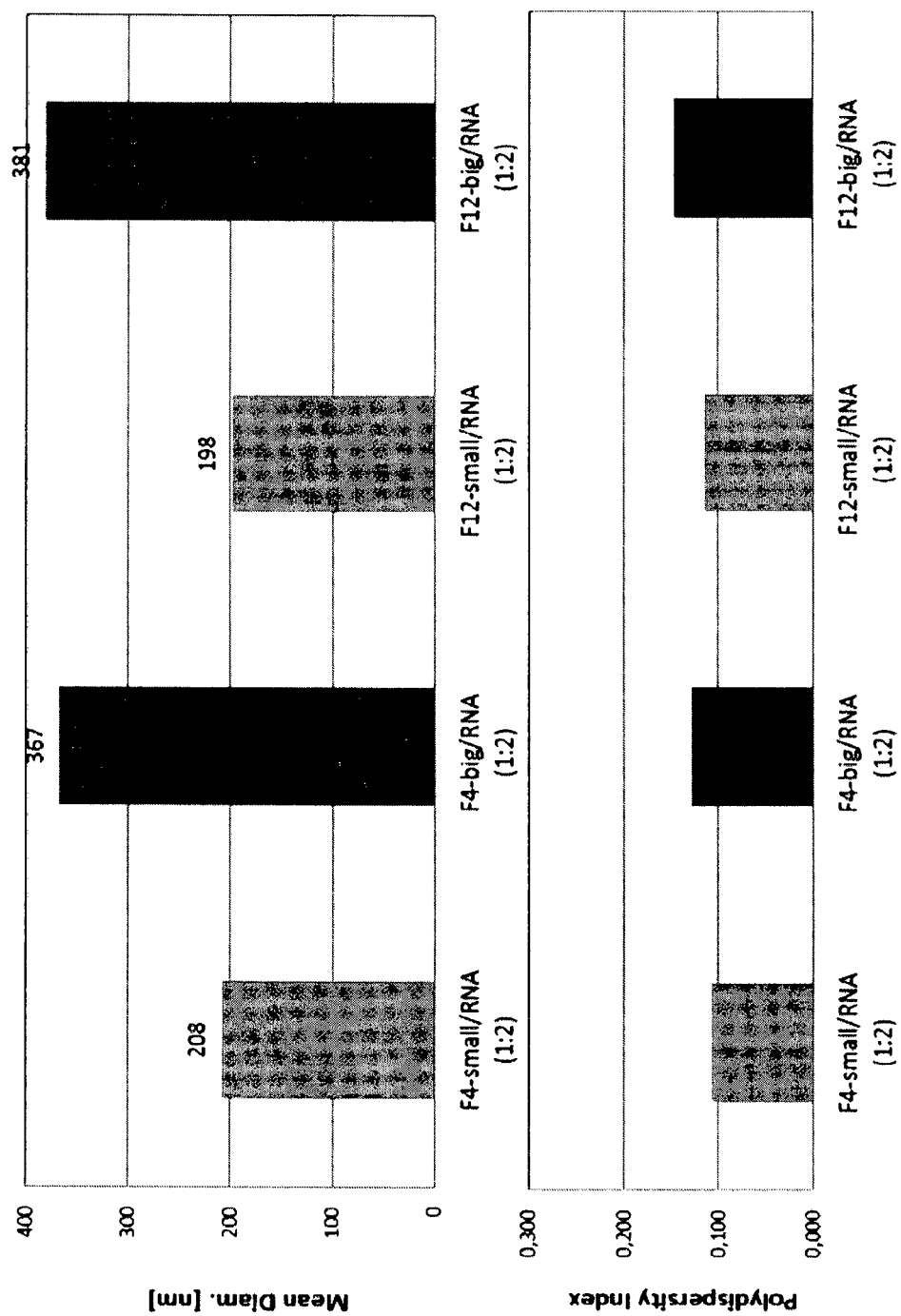

FIG. 30: Particle size and Polydispersity Index of 1:2 lipoplexes of extruded and non extruded liposomal precursors.

Figure 31:
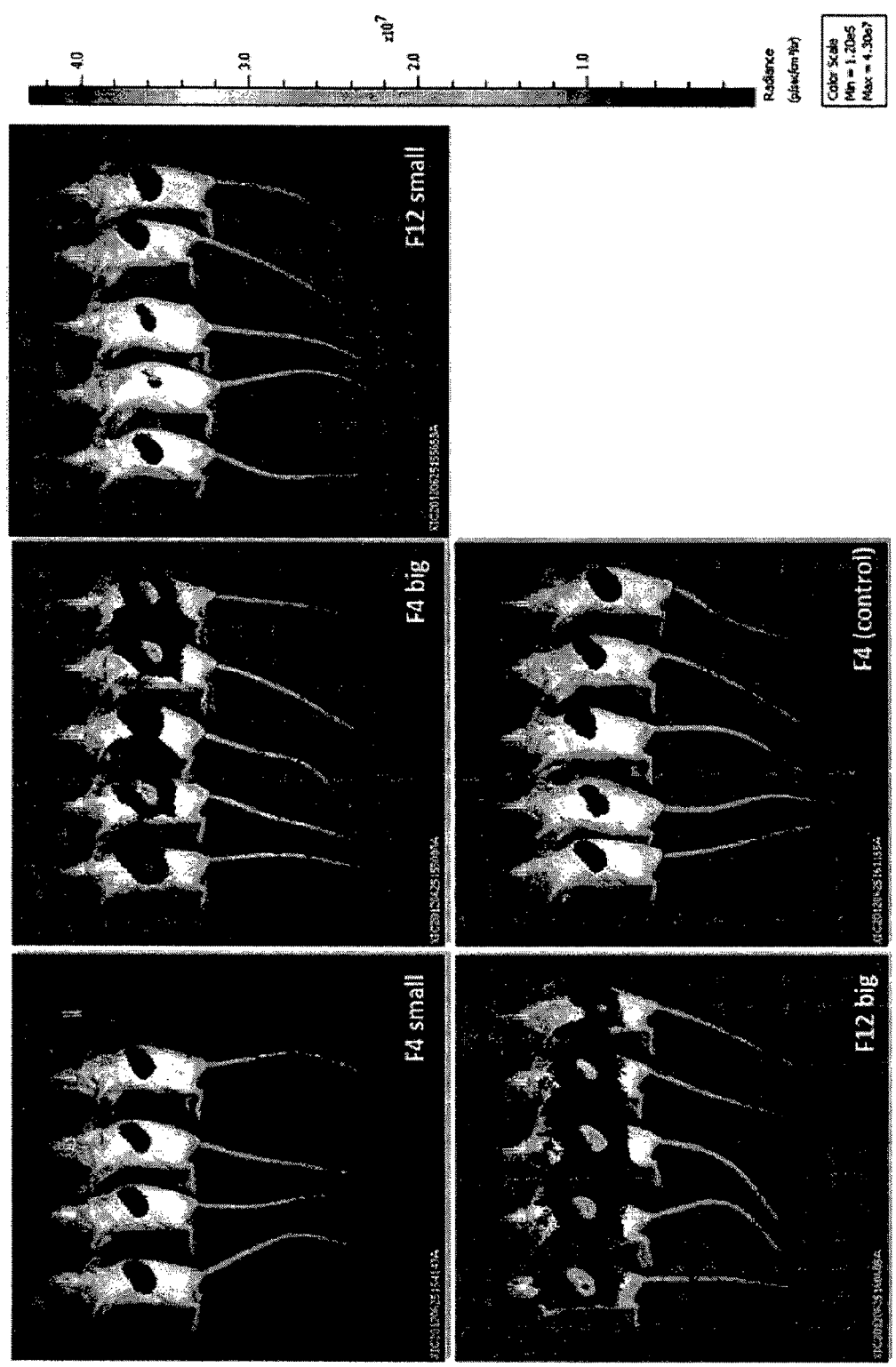

FIG. 31: Luciferase activities in vivo after injection into BALB/c mice of luciferace-RNA (20 µg) complexed with small or big liposomes in PBS to achieve lipoplexes different in size.

Figure 32:
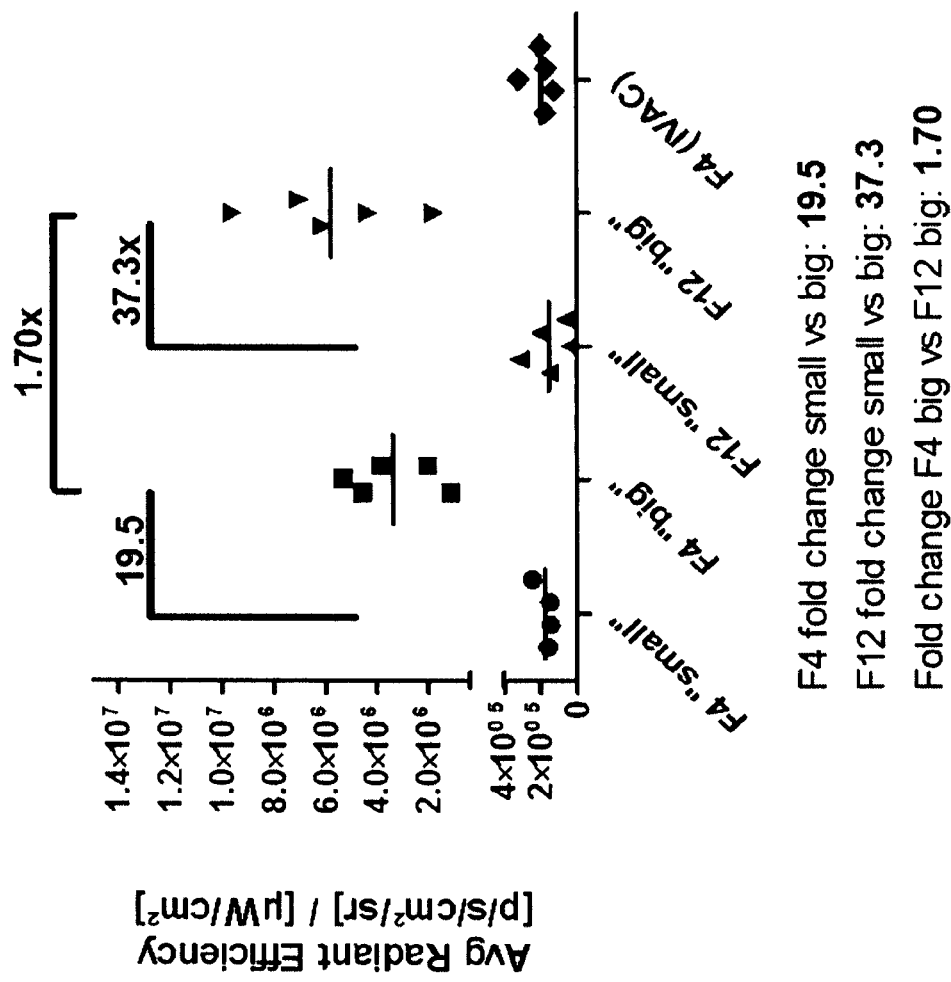

FIG. 32: Quantification of luciferase activities in spleens of mice after injection of Luciferase-RNA lipoplexes different in size. Lager lipoplexes, assembled from larger liposomes, have higher activity, independent from the lipid composition of the liposomes.

Figure 33:
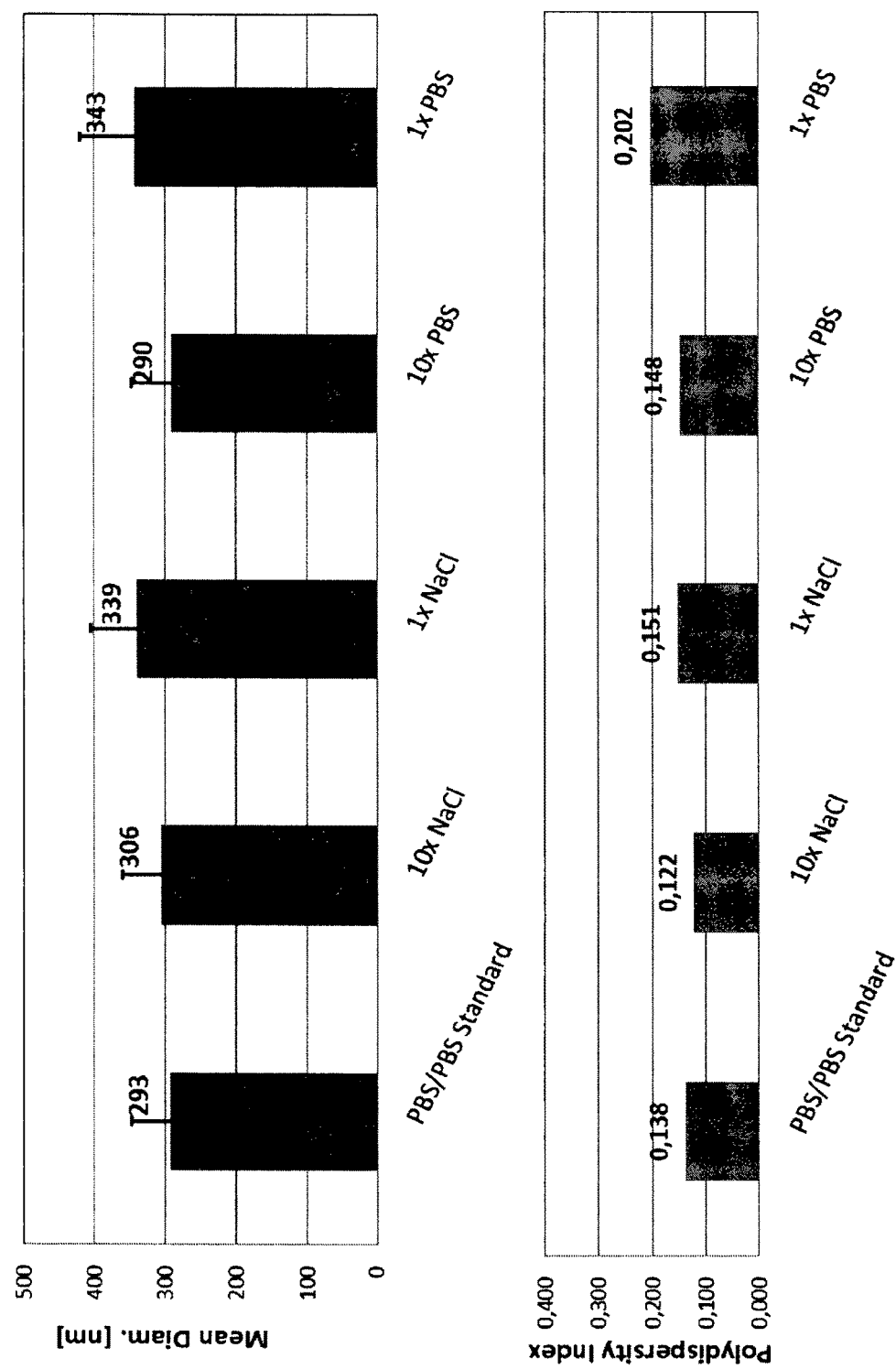

FIG. 33: Lipoplexes formed by using NaCl and PBS buffer in 'normal' and 10× concentrated form. In the latter case, a 10-fold lower volume was added to obtain the same final concentration. All lipoplexes have about the same size but those from concentrated solutions are a bit smaller.

Figure 34:
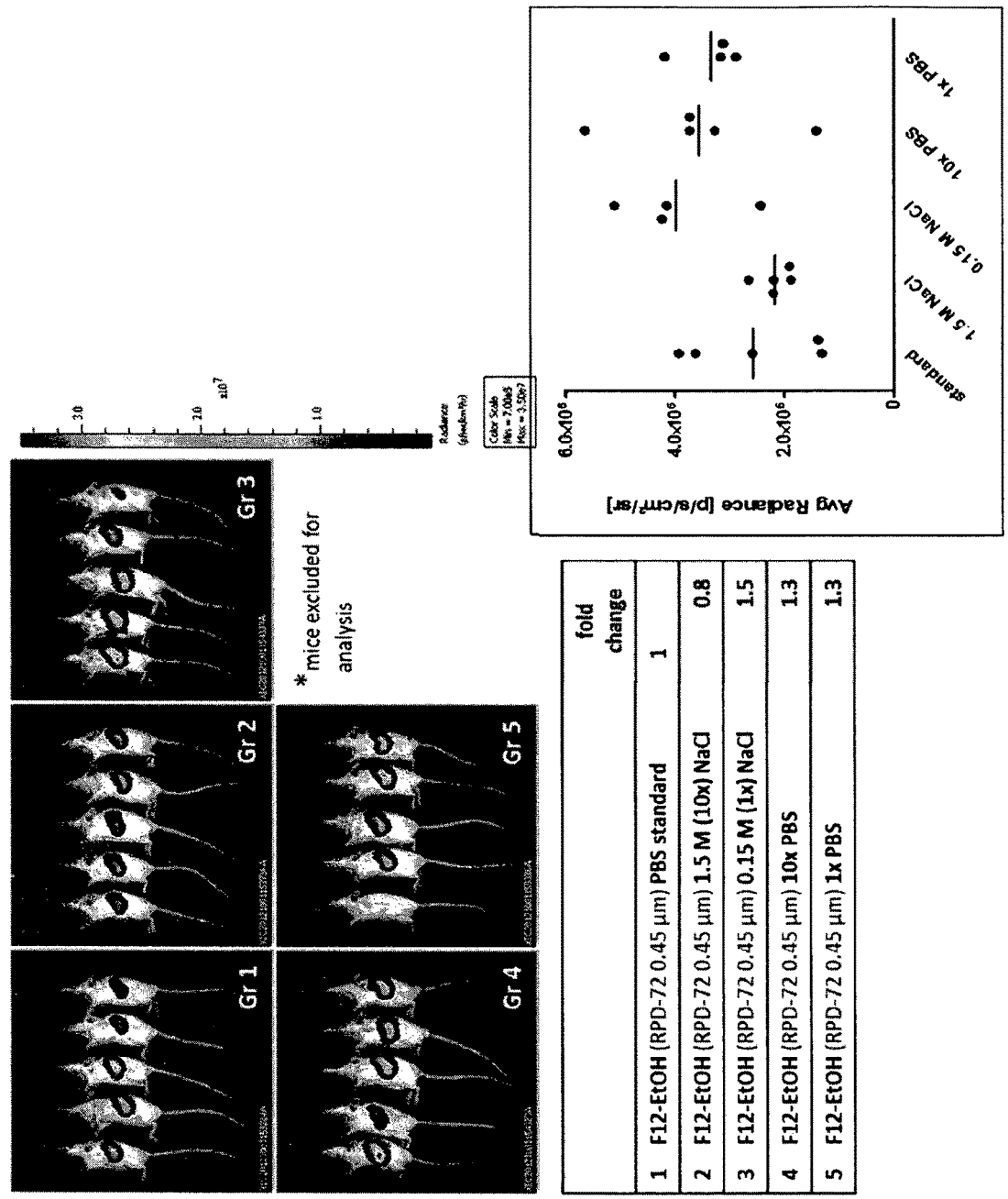

FIG. 34: Activity (luc expression) of the lipoplexes measured in FIG. 33. As a trend, the lipoplexes from non-concentrated buffers are higher in activity. Treatment with normal saline yields highest activity.

Figure 35:
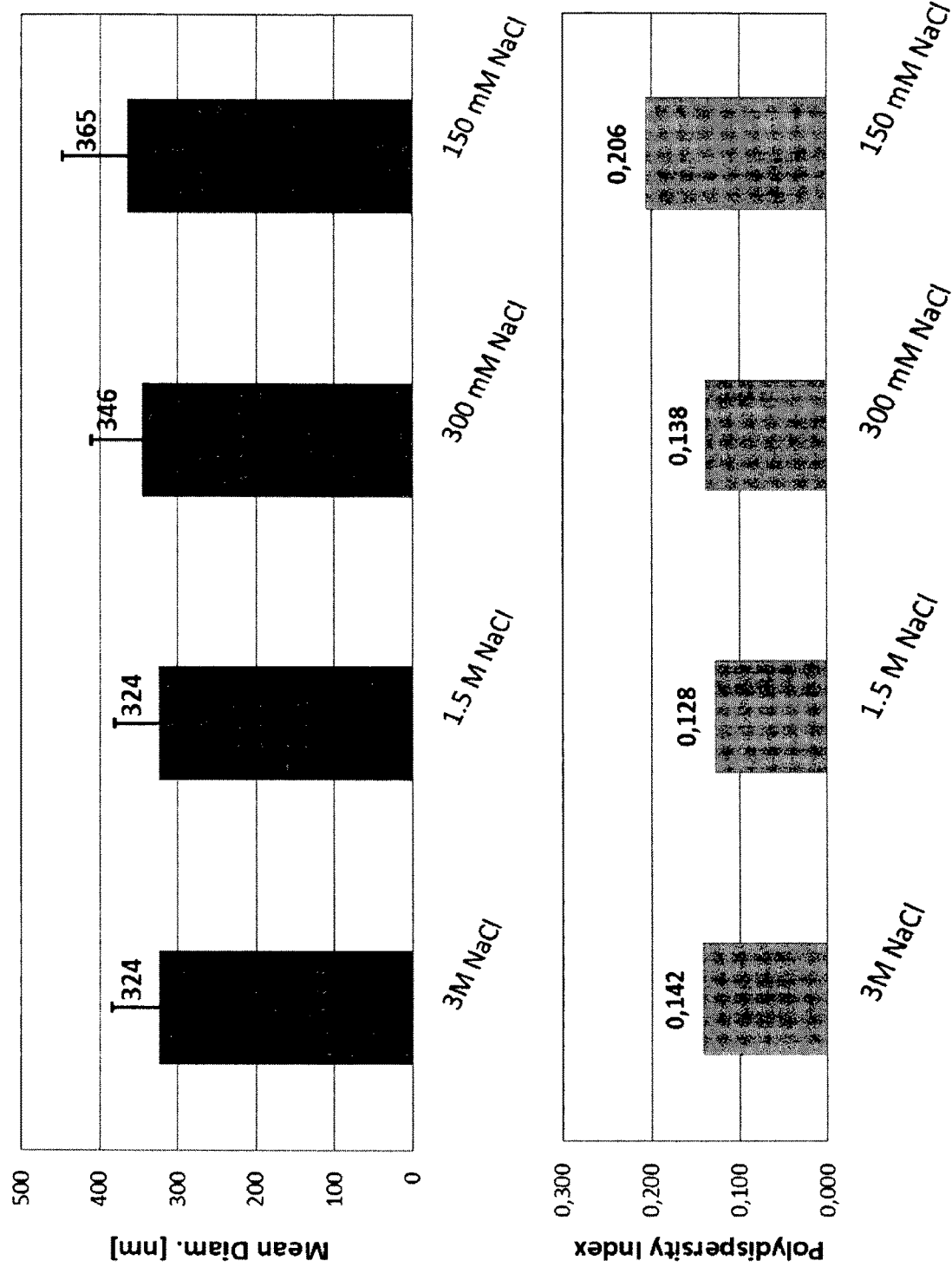

FIG. 35: Lipoplexes formed after addition of the NaCl to the RNA at different concentrations. The final NaCl concentration was in all cases the same, as from the concentrated solutions lower volumes were added. As a trend, the lipolex size increases with decreasing concentration of the added NaCl solution. As larger lipoplexes are higher in activity than smaller ones, use of 0.9% NaCl (150 mM) is considered to result in the best activity.

Figure 36:
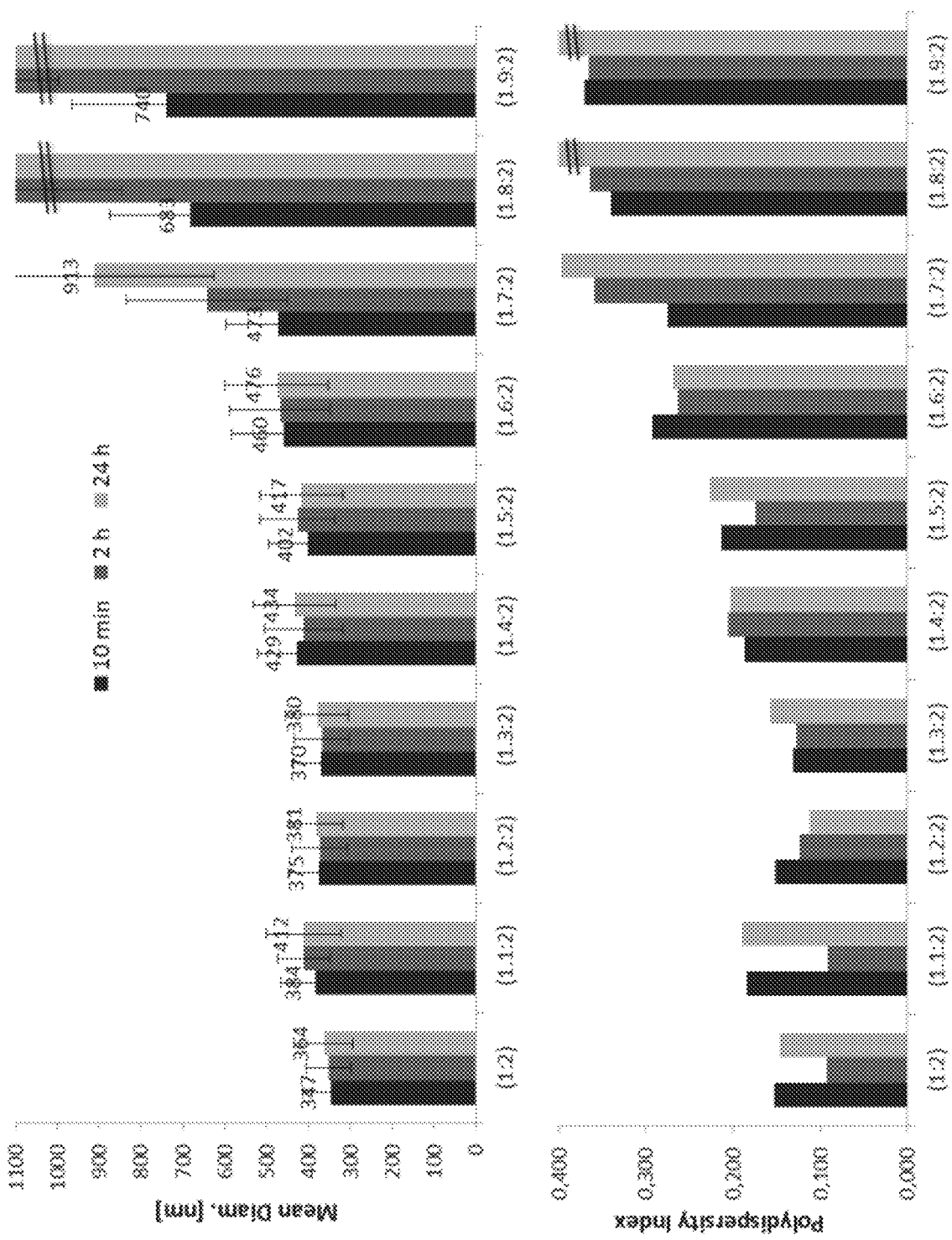

FIG. 36: Size (Zave) and Polydispersity Index (PI), for lipoplexes with different mixing ratios (DOTMA/nucleotide ratios), directly after reconstitution, and after 2 h and 24 h.

Figure 37:
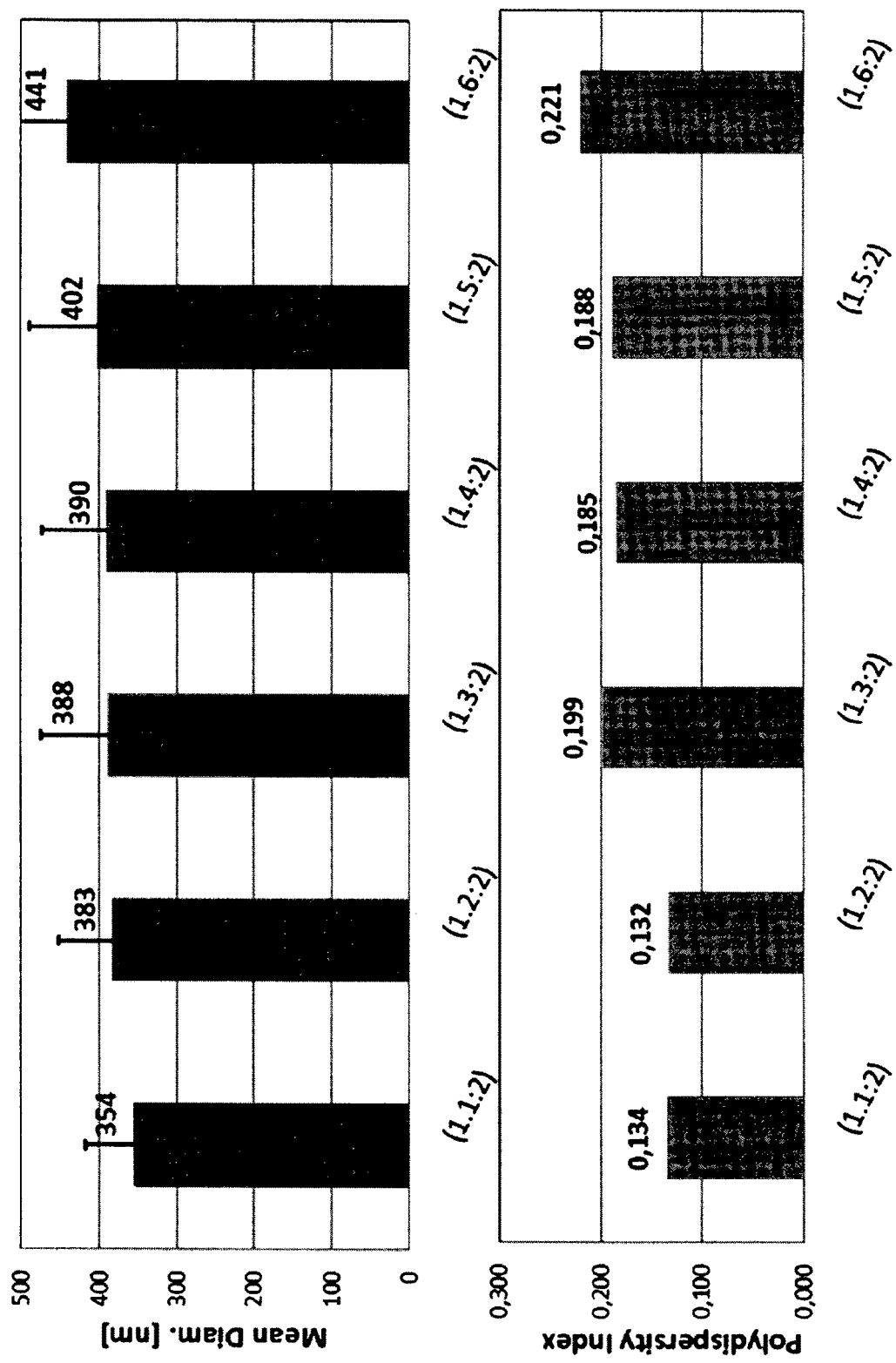

FIG. 37: Results of DLS measurements of RNA lipoplexes with different charge ratios tested in vivo.

Figure 38:
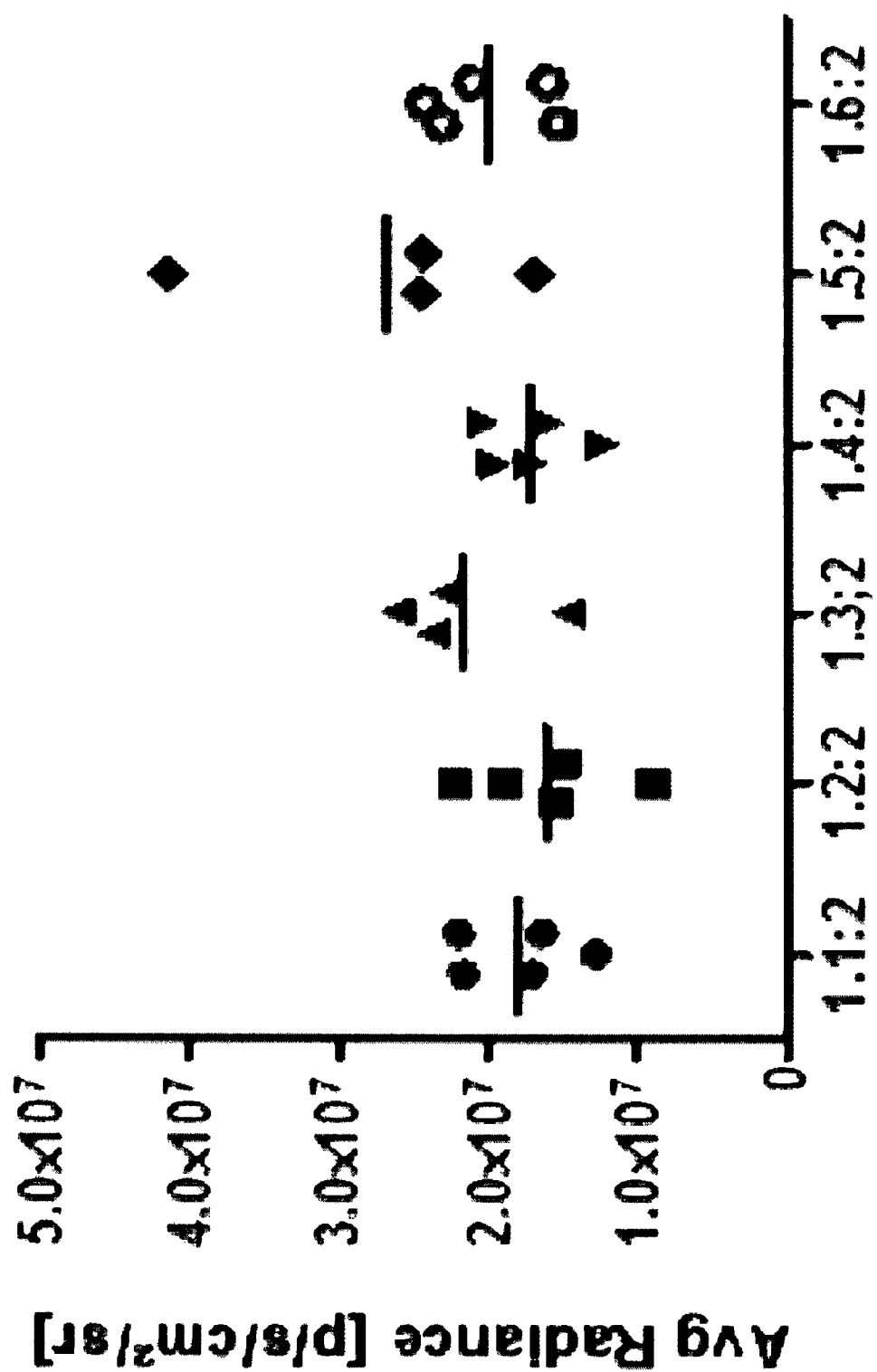

FIG. 38: Quantification of luciferase activities in spleens of mice after injection of Luciferase-RNA lipoplexes different in size.

EXAMPLES

The techniques and methods used herein are described herein or carried out in a manner known per se and as described, for example, in Sambrook et al., Molecular Cloning: A Laboratory Manual, 2$^{nd}$ Edition (1989) Cold Spring Harbor Laboratory Press, Cold Spring Harbor, N.Y. All methods including the use of kits and reagents are carried out according to the manufacturers' information unless specifically indicated.

Example 1: Materials and Methods

Liposome Preparation

Manufacturing of liposomes was performed by different protocols. The 'film method' or 'ethanol injection' was used for liposome preparation. For the film method, the lipids were dissolved in chloroform and put in appropriate amounts into a round bottom flask. The organic solvent was evaporated in a rotary evaporator and the dry film was reconstituted with water or buffer/excipient solution by gently shaking of the flask. Typically, a total lipid concentration of 5 mM was selected. For ethanol injection, the lipids were dissolved at suitable molar ratios in ethanol to a total concentration in the range of 100-400 mM. The ethanol solution was injected under stirring into water or the aqueous solution of buffers/excipients. The size of the liposomes was adjusted by extrusion across polycarbonate membranes of different pore size (50-400 nm), and/or they were filtered through commercially available sterile filters of 220-450 nm pore size, or filters for clinical use with other pore sizes (1 µm-5 µm) were used (Sartorius, Göttingen, Germany, Millipore, Schwalbach, Germany).

The final lipid concentration in the aqueous phase was between 5 mM and 25 mM. Lipid composition was controlled by HPLC analysis. Particle size and zeta potential were determined by dynamic light scattering.

Lipoplex Formation

Lipoplex formation was performed by different protocols. The detailed procedure is given with the individual experiments. For several experiments, direct incubation of RNA solutions with liposome solutions in water or in the presence of buffers or excipients was performed. Lipoplexes could also be formed by mixing of lipid solutions in ethanol with RNA solutions in water or aqueous buffer/excipient solutions. The selected preparation protocol depended on the desired particle characteristics and biological application and is further described with the respective experiments.

PCS Measurements

Particle size and zeta potential measurements were performed on a 380 ZLS submicron particle/zeta potential analyzer (PSS Nicomp, Santa Barbara, Calif.). Size was determined by Photon correlation spectroscopy (PCS) at a scattering angle of 90° with an equilibration time of 2 min and run times of 15 min. Auto correlation was performed using the intensity-weighted Gaussian analysis, which gives information about the mean diameter of the bulk population and the polydispersity index (PI).

Zeta Potential

Zeta potential was measured in water using electric field strength of 5 V/cm and an electrode spacing of 0.4 cm. The electrostatic mobility was converted to the zeta potential using the Helmholtz-Smoluchowski equation. All measurements were carried out at a temperature of 23° C.

Field-Flow-Fractionation

Asymmetrical Flow FFF (AF4) was performed using the Eclipse 3+ system equipped with a long channel (275 mm length) and the triple-angle MALS light scattering detector miniDAWN TREOS (Wyatt Technologie, Dernbach, Germany) using the following hardware/parameters:

Membrane: 10 kD regenerated cellulose (Microdyn Nadir, Wiesbaden, Germany)
Spacer: 250 µm spacer (wide 21.5 mm)
Solvent: 10 mM NaNO3
Detector flow: 1.0 mL/min
Focus flow: 1.5 mL/min
Injektion flow: 0.2 mL/min
Cross flow gradient: 4 mL/min (fixed for 15 min, than 4 mL/min to 0.1 mL/min in 20 min).

Animals

C57BL/6 and BALB/c mice were from Jackson Laboratories. Age (8-10 weeks old) and sex (female) matched animals were used throughout the experiments.

Cells and Cell Lines

B16-OVA is a B16-F10 melanoma cell line expressing the chicken ovalbumin gene (OVA). Human monocyte derived immature DCs (iDC) were differentiated from purified $CD14^+$ monocytes in the presence of IL-4 (1000 U/ml) and GM-CSF (1000 U/ml) for 5 days.

RNA Constructs and In Vitro Transcription

All plasmids for in vitro transcription of naked antigen-encoding RNA were based on the pST1-2hBgUTR-A120 backbone which feature a 3' human β-globin UTR (hBgUTR) and a poly(A) tail of 120 nucleotides and allow generation of pharmacologically improved in vitro transcribed RNA. The SIINFEKL construct contains aa 257-264 of chicken OVA. HA construct was a codon optimized partial sequence of influenza HA (aa 60-285 fused to aa 517-527; influenza strain A/PR/8/34) designed to combine major immunodominant MHC epitopes. pSTI-Luciferase-A120 (Luc) contains the firefly luciferase gene (15). RNA was generated by in vitro transcription. Labeling of RNA with Cy5-UTP (Cy5-RNA) was conducted according to the manufacturer's instructions (Amersham Biosciences, Buckinghamshire, UK) using the HA construct as template.

Preparation and Injection of Lipoplexes

Unless otherwise stated, as standard protocol, RNAs and Liposomes were prediluted in 1× RNase free phosphate buffered saline (PBS) (Ambion) to a final volume of 100 µl prior to mixing. 10 minutes after mixing of diluted RNA and liposome, 200 µl lipoplex solution was injected per mouse intravenously. For some experiments, PBS was replaced with 154 mM RNase free NaCl (Ambion)

Flow Cytometric Analysis

Monoclonal antibodies for flow cytometry were from BD Pharmingen. Hypotonicly lysed blood samples were incubated at 4° C. with specific mABs. Spleen cells were obtained by digestion with collagenase (1 mg/ml; Roche). Quantification of SIINFEKL-specific $CD8^+$ cells with H-2 $K^b$/SIINFEKL tetramer (Beckman-Coulter) was previously described. Flow cytometric data were acquired on a FACS-Canto II analytical flow cytometer and analyzed by using FlowJo (Tree Star) software.

Electroporation

50 µl of RNA solution was electroporated into iDCs with electoporation parameters of 270V and 150 µF using BioRad electroporator.

In Vivo Bioluminescence Imaging (BLI)

Uptake and translation of Luc-RNA were evaluated by in vivo bioluminescence imaging using the IVIS Lumina imaging system (Caliper Life Sciences). Briefly, an aqueous solution of D-luciferin (150 mg/kg body weight) (BD Biosciences) was injected i.p. 6 h after administration of RNA lipoplexes. 5 min thereafter, emitted photons were quantified (integration time of 1 min). In vivo bioluminescence in regions of interest (ROI) were quantified as average radiance (photons/sec/cm$^2$/sr) using IVIS Living Image 4.0 Software. The intensity of transmitted light originating from luciferase expressing cells within the animal was represented as a grayscale image, where black is the least intense and white the most intense bioluminescence signal. Grayscale reference images of mice were obtained under LED low light illumination. The images were superimposed using the Living Image 4.0 software.

ELISA

Mouse IFN-α (PBL) and TNFa (eBioscience) was detected in mouse sera using standard ELISA assay according to manufacturer's instructions.

Tumor Experiments

To determine protective immunity, mice received three immunizations. Thereafter, 2×105 B16-OVA tumor cells were inoculated s.c. into the flanks of C57BL/6 mice. For assessment of therapeutic immunity, first same numbers of tumor cells were inoculated. Immunizations were then initiated after tumors had reached a diameter of 2 to 3 mm. Tumor sizes were measured every three days. Animals were sacrificed when the diameter of the tumor exceeded 15 mm.

Example 2: Effect of Buffers/Ions on Particle Sizes and PI of RNA Lipoplexes

Lipoplexes of liposomes and RNA at different charge ratios +/− between the cationic (positively charged) lipid DOTMA and the negatively charged RNA were prepared. The physiochemical characteristics of the liposomes were investigated by dynamic light scattering (PCS) and zeta potential measurements.

The use of buffer which is often necessary for pharmaceutical applications and ions can lead to aggregation of lipoplexes which makes them unsuitable for parenteral application to patients. In order to evaluate these effects on the average diameter of lipoplexes, the particle characteristics of lipoplexes of DOTMA/DOPE (F4) liposomes [DOTMA/DOPE (1:1 mol:mol)] and RNA at different charge ratios were determined under four buffer conditions, namely, water, PBS buffer, PBS plus 2.2 mM $CaCl_2$, and PBS plus 22 mM $CaCl_2$. For the measurements, briefly, lipoplexes were formed by adding of RNA to preformed liposomes, subsequently the buffers were added. The final RNA concentration was selected to about 100 µg/ml. All other concentrations were adjusted accordingly or selected as given in the figures. Particle sizes are shown in FIG. 1. The DOTMA/RNA charge ratio is given on the x-axis of each chart.

(a) In water, lipoplexes of defined particle sizes (mean size less than 300 nm), with low polydispersity indices (<0.3) were obtained. The measured particle sizes were only slightly affected by the charge ratio. However, negatively charged particles are smaller (mean size 100 to 200 nm) and more stable (PI<0.15) than uncharged particles (mean size 200 to 250 nm, PI<0.2).

(b) In PBS buffer, the same effect is more prominent. Lipoplexes with a positive or neutral charge ratio form larger particles (partially stabilized by the positive charges). Lipoplexes with a neutral charge ratio are building unstable aggregates. In contrast, negatively charged lipoplexes are both stable (as indicated by a low PI<0.2) and compact with average particle sizes of 250 nm and less.

(c) After addition of $CaCl_2$ an increase in the particle sizes is observable. However, at physiological $Ca^{++}$ concentrations (shown: 2.2 mM; in some cell types the physiological concentration can be up to 5 mM, rarely up to 10 mM) negatively charged particles still have defined sizes below 500 nm with a polydispersity index not exceeding 0.6. For the sample with excess positive charge the size increased almost to 1000 nm.

(d) Addition of 22 mM $CaCl_2$ to the samples b) (PBS) induced aggregation/flocculation under all conditions, supposedly due to formation of calcium phosphate particles.

These results demonstrate that in buffered solutions such as i.e. in PBS buffer and/or in the presence of $CaCl_2$, positive or neutral charge ratios are poorly suited for the production of stable liposomal formulations. The stability of lipoplexes highly depends on the charge ratio +/− between the cationic DOTMA lipid and the charged RNA. In addition, both the ionic strength of the formulation buffer and the presence of bivalent cations have strong influences on particle sizes. Under physiological conditions (i.e. pH 7.4; 2.2 mM $Ca^{++}$), a negative charge ratio appears to be imperative due to the instability of neutral or positively charged lipoplexes. For lipoplexes with excess negative charge the lowest trend for aggregation was observed.

Example 3: Effect of Positive Charge on Stability of RNA Lipoplexes

For an additional evaluation of a potential beneficial/detrimental effect of positive charges on the stability of lipoplexes (see e.g. FIGS. 1 b and c), particle sizes of lipoplexes of DOTMA/Chol liposomes (F5) [DOTMA/Chol (1:1 mol:mol)] and RNA with DOTMA/RNA charge ratios of 1/1 and 2/1 were measured in different buffers (see FIG. 2). For comparison, also the size of the pure liposomes was measured.

In 150 mM sodium chloride as well as in PBS buffer a positive 2/1 DOTMA/RNA charge ratio leads to largely increased/aggregated particle sizes with a polydispersity index greater than 0.4. This result indicates that positive charges are not suitable to stabilize lipoplexes and that aggregation has to be expected for the positively charged lipoplexes also under physiological conditions.

Example 4: Influence of Pre-Compaction of RNA Mediated by Bivalent Cations on the Particle Size of RNA Lipoplexes To test the influence of pre-compaction of RNA using divalent cations prior to the complexation, the particle size of F5/RNA lipoplexes at charge ratios (1/1) and (1/2) were determined after compaction of the RNA with different amounts of $CaCl_2$. Contrary to Examples 2 and 3 here the ions were added to the RNA prior to lipoplex formation. The final liposome concentration was in all cases 100 µM, and the RNA concentration was adjusted accordingly. Because for the F5/RNA 1/2 the RNA concentration was doubled, here also the $CaCl_2$ concentration was doubled.

After pre-treatment of the uncharged RNA/F5 (1:1) lipoplexes with physiological concentrations of $CaCl_2$ (i.e. 2.2 mM), the average size of the resulting lipoplex particle is inflated (i.e. to 1.2 µm); see FIG. 3. Due to this large size, such particles are not ideally suited for pharmaceutical compositions and/or the delivery of RNA into cells. In contrast, both pre-compaction experiments with negatively charged lipoplexes and low/high concentrations (low: 0.3 mM; high: 4.4 mM) of $CaCl_2$ produced small-sized particles of approximately 200 (350) nm.

These results indicate that RNA can be precondensed with bivalent ions. Due to this precondensation step, lipoplexes with defined and compact particle sizes can be formed at negative charge ratios; aggregation or substantial increase of particle size can be prevented.

Example 5: Physico-Chemical Characterization of RNA Lipoplexes

In FIG. 4, results from physico-chemical characterization of RNA lipoplexes with F4 (DOTMA/DOPE) at different charge ratios +/− between DOTMA and RNA are given. As can be seen for negatively charged lipoplexes, at +/− ratios of 1/1 and above, the particle size is constant at about 200 nm. The zeta potential decreases monotonously from +/−2/1 to 1/1, and it remains constant at higher excess negative charge. These results suggest that important particle characteristics, namely particle size and zeta potential, are invariant with excess RNA, starting from the 1/1 ratio. In this range, colloidal stable particles of well-defined size can be manufactured. Similar results can also be obtained in the presence of ions and buffers (PBS).

Example 6: Effect of Buffer Composition on Stability/Particle Size of Negatively Charged RNA Lipoplexes The stability of lipoplexes in different buffers was further investigated to detail. To test if an excess of negative charge leads to colloidal stable lipoplexes in potential relevant buffer systems, particle sizes of F4/Luc-RNA lipoplexes at the charge ratio (1/2) in water and after addition of concentrated buffer to PBS (lx), sodium chloride (150 mM), glucose (5%) or phosphate buffered glucose were determined (see FIG. 5).

Under all tested conditions, particle sizes are not exceeding 300 nm with PI values of clearly less than 0.4. These results suggest that, if manufactured according to the present invention, RNA lipoplexes with a charge ratio of 1/2 (excess of negatively charged RNA) are colloidally stable under different buffer conditions.

Example 7: Correlation of Negative Charge Ratio and Particle Size/Stability

The colloidal stability of the lipoplexes at the ratio between (1/1) and (1/2) was further investigated. Particle sizes of F4/RNA lipoplexes with charge ratios between 1:1.8 and 1:1.2 were measured in water; see FIG. 6.

These results suggest that in the range of the tested charge ratios the particle size of lipoplexes are invariant to minor changes in excess RNA. In connection with the tested (negative) charge ratios of 1:1.2 to 1:1.8, particles sizes are generally in the 100 to 200 nm range with PI values of less than 0.2.

Example 8: Effect of Extrusion on Mean Particle Size and PI Values of RNA Lipoplexes In this experiment it is shown that lipoplexes of different size can be produced. In order to determine the effect of an additional extrusion step on mean particle size and PI values of liposomes or RNA lipoplexes, extrusion experiments (using a polycarbonate membrane with different pore diameters) were performed. Results from particle sizing of RNA lipoplexes with un-extruded F4 (DOTMA/DOPE) and with extruded F4 in water or PBS are shown in FIG. 7.

The experiments demonstrate that, in addition to the already described size range of 200-300 nm, also larger and smaller particles can be produced. Here, as an example particles with size in the range of 400-500 nm and <100 nm were are given.

Whereas non-extruded RNA lipoplexes show average particle sizes between 400 and 500 nm, extruding of RNA lipoplexes generally leads to significantly smaller particles with sizes of less than 200 nm. In contrast, the effect of extrusion on the polydispersity is marginal; both extruded and non-extruded liposomes lead to discrete, well defined particles (with PI values between 0.1 and 0.3), if complexed with RNA.

Example 9: Effect of Lyophilization on the Particle Characteristics

Lipoplexes are not stable in liquid suspension for long-term storage and aggregate. Lyophilization is one technique to address this challenge. The effect of lyophilization on the particle characteristics was investigated. Particle sizes of DOTMA/DOPE liposomes (F4) were determined before lyophilization and after lyophilization and reconstitution with water (see FIG. 8).

These results suggest, that the lipoplexes can be lyophilized without affection the particle characteristics.

Example 10: Effect of DOTMA/DOPE Ratio on the Particle Characteristics

Liposomes and lipoplexes with different DOTMA/DOPE ratios were manufactured. Liposomes with very high DOPE fraction (90 mol %) were unstable in PBS (FIG. 9). For lipoplexes, already at a DOPE fraction of 70 mol %, the particle size significantly increased (FIG. 10). All other compositions were stable.

Example 11: In Vivo Administration of RNA Lipoplexes

BALB/c mice (n=3) were injected intravenously with Luciferase-RNA (20 µg) complexed with different amounts of F4 liposomes to yield F4:RNA ratios of 4.8:1, 2.4:1, 1.2:1, 1.2:2, 1.2:4. Luciferase activities in vivo and ex vivo were assessed via in vivo imaging 6 hours after lipoplex injection and representative mice and organ sets are shown in FIG. 11. FIG. 12 shows the distribution of total luciferase signal among organs derived from the experiment depicted in FIG. 11.

F4 (DOTMA:DOPE) goes more to lungs (a little spleen) at the ratio of F4:RNA of 4.8:1, to both lungs and spleen at the ratio of F4:RNA of 2.4:1 and exclusively to spleen at ratios of F4:RNA of 1.2:1, 1.2:2, 1.2:4. Thus, neutral and anionic lipoplexes target specifically to spleen whereas cationic lipoplexes primarily target lung (wrt to protein expression). No expression in liver was detected.

BALB/c mice (n=5) were injected intravenously with Luciferase-RNA (20 µg) complexed with F11 or F12 liposomes with an Fx:RNA ratio of 1.2:2 [F11: DOTMA/DOPE (1:2 mol:mol); F12: DOTMA/DOPE (2:1 mol:mol)]. Luciferase activities in vivo and ex vivo were assessed via in vivo imaging 6 hours after lipoplex injection and representative mice and organ sets are shown in FIG. 13. F4 derivatives F11 and F12 also target to spleen at an liposome: RNA ratio of 1.2:2.

BALB/c mice (n=5) were injected intravenously with Luciferase-RNA (20 µg) complexed with F2 or F5 liposomes with an Fx:RNA ratio of 1:1 [F2: DOTAP/DOPE (1:1 mol:mol); F5: DOTMA/Chol (1:1 mol:mol)]. Luciferase activities in vivo and ex vivo were assessed via in vivo imaging 6 hours after lipoplex injection and representative mice and organ sets are shown in FIG. 14. At liposome:RNA ratio of 1:1, while F2 targets to spleen, F5 targets to both spleen and lungs.

Luciferase-RNA (20 µg) diluted in 1×PBS (A) or undiluted in water (B and C) was complexed with F4 liposomes diluted in 1×PBS (B) or undiluted in water (A and C) with an F4:RNA ratio of 1.2:2. The final PBS concentrations of all complexes were set to 1×PBS. BALB/c mice (n=5) were then injected intravenously with A, B or C and luciferase activities in spleens of mice were quantified via in vivo imaging (Mean+SD); see FIG. 15.

As a standard mixing protocol, both liposomes and RNA are diluted in PBS (1×PBS final conc.) and then mixed at equal volumes. Predilution of only RNA is as good as standard protocol. All other protocols lacking predilution of RNA in PBS yielded poorer results. Presence of ions in RNA solution prior to complexation is preferred for achieving good results Luciferase-RNA (20 µg) precomplexed with 0.125 or 1 mM $CaCl_2$ or without precomplexation was mixed via standard protocol with F4 liposomes with an F4:RNA ratio of 1.2:2. BALB/c mice (n=5) were injected intravenously with these formulations and luciferase activities in vivo were quantified from spleens of mice (Mean+SD); see FIG. 16.

Precondensation of RNA with 1 mM $CaCl_2$ when PBS is used as a buffer increases the luciferase signal 3-fold (Higher concentrations of $CaCl_2$ in the presence of PBS leads to large particles-aggregates). Precondensation of RNA with $Ca^{2+}$ helps to increase the luciferase signal.

Luciferase-RNA (20 µg) or F4 liposomes diluted in 1×PBS or 154 mM NaCl were mixed with an F4:RNA ratio of 1.2:2. BALB/c mice (n=5) were injected intravenously with these formulations and luciferase activities in vivo were quantified from spleens of mice (Mean+SD); see FIG. 17.

Using standard mixing protocol, replacement of PBS with isoosmolar NaCl worked as good as PBS.

Luciferase-RNA (20 µg) precomplexed with 1-4 mM $CaCl_2$ was mixed using standard protocol with F4 liposomes with an F4:RNA ratio of 1.2:2 using 154 mM NaCl instead of 1×PBS as dilution buffer. BALB/c mice (n=5) were injected intravenously with these formulations and luciferase activities in vivo were quantified from spleens of mice (Mean+SD); see FIG. 18.

When PBS is replaced with NaCl, 2 mM $CaCl_2$ can be used leading to 4.5-fold increase (higher concentrations of $CaCl_2$ do not further increase the signal).

Luciferase-RNA (5 µg) was incubated in 25 or 50% mouse serum for 30 min. and then electroporated into human monocyte derived immature DCs. Luciferase activity was assessed 18 h later via standard in vitro luciferase assay (Mean+SD); see FIG. 19A. Luciferase-RNA (20 µg) was complexed via standard protocol with F4 liposomes with an F4:RNA ratio of 1.2:2 and then incubated in the presence or absence of 50% mouse serum for 30 min.

BALB/c mice (n=5) were injected intravenously with these formulations and luciferase activities in vivo were quantified from spleens of mice (Mean+SD); see FIG. 19B.

Naked RNA is degraded in the presence of serum. Complexation of RNA with F4 liposomes protect it from RNase mediated degradation in serum.

BALB/c mice (n=3) were injected intravenously with Cy5-RNA (40 µg) complexed with F4 liposomes labeled with Rhodamine (F4-rho) (1.2:2; Liposome:RNA). Uptake of Cy5-RNA or F4-rho by cell populations in spleen was assessed by flow cytometry 1 hour after lipoplex injection; see FIG. 20.

As professional antigen presenting cells (APCs), splenic DCs and macrophages efficiently internalized the liposome encapsulated RNA and the liposome itself while B and T cells hardly internalized neither the liposome encapsulated RNA nor the liposome itself. Thus, RNA lipoplexes are selectively internalized by splenic APCs C57BL/6 mice (n=3) were injected with HA-RNA (40 µg) complexed with F4 (1.2:2; Liposome:RNA), F4 alone or PBS (as control); see FIG. 21. (A) Maturation status of dendritic cells (revealed by upregulation of CD86 and CD40) in spleen was determined by flow cytometry 24 hours after treatments (Mean+SD). (B) Serum concentrations of IFNa and TNFa were assessed via ELISA 6 and 24 hours after treatments (Mean+SD).

As revealed by upregulation of activation markers (CD86, CD40) on DCs, RNA-F4 lipoplexes actived splenic DCs while liposome alone did not. Interestingly, although RNA-F4 lipoplexes were detected in 5-10% of splenic DCs in a previous experiment, all DCs were activated in spleen implying for the existence of an inflammatory milieu in spleen upon delivery. In all animals injected with RNA-lipoplexes, we could detect a high amount of IFNa in blood 6 h (also after 24 h although in much lower quantities). We could also detect TNFa but at very moderate levels in all animals injected with RNA-lipoplexes (only after 6 h). The secretion of cytokines is specific to RNA-lipoplexes as neither the PBS nor the liposome alone did not lead to any significant cytokine secretion (baseline). Thus, RNA lipoplexes activate splenic DCs leading to systemic inflammation C57BL/6 mice (n=5) were immunized intravenously with SIINFEKL-RNA (20 or 40 µg) complexed with F4 liposomes at different liposome:RNA ratios on days 0, 3, 8 and 15; see FIG. 22. (A) The frequencies of antigen specific CD8+ T cells were determined via SIINFEKL-MHC tetramer staining 5 days after the last immunization (Day 20) (Mean+SD). (B) Memory recall responses were assessed via SIINFEKL-MHC tetramer staining on Day 62 after another injection of F4-RNA lipoplexes on Day 57 (Mean+SD).

High order of antigen-specific T cell immunity could be generated after repetitive immunization with F4 lipoplexes (A). 6 weeks after the last immunization (d57), a boost lipoplex injection was able to expand CD8 T cell memory formed in the former injections (B). F4 (1.2:1) complexes formed aggregates while F4 (1.2:2) complexes were clear. Preferred is F4 (1.2:2) with 40 µg RNA. Thus, strong T cell effector and memory responses can be generated with RNA-lipoplexes On days 0, 3 and 8, C57BL/6 mice (n=3) received three intravenous immunizations of SIINFEKL-RNA (40 µg) complexed with F4 liposomes with an F4:RNA ratio of 1.2:2 or left untreated. On day 14, 2×10$^5$ B16-OVA tumor cells were injected s.c. into the flanks. Kaplan-Meier survival curves are shown in FIG. 23.

Complete protection was achieved with RNA lipoplex administration in the prophylactic B16-OVA model.

2×10$^5$ B16-OVA tumor cells were inoculated s.c. into the flanks of C57/Bl6 mice (n=10, d0). At day 10 (tumor diameter 2-3 mm), mice received seven intravenous immunizations of SIINFEKL-RNA (40 µg) complexed with F4 or F12 liposomes with an F4:RNA ratio of 1.2:2 (on days 10, 13, 17, 24, 31, 38, 45). Liposomes alone without SIINFEKL-RNA were used as control treatment. Individual tumor growth and Kaplan-Meier survival curves are shown in FIGS. 24 and 25, respectively.

In a therapeutic model, significantly delayed tumor growth for F4+RNA or F12+RNA groups was detected. Shrinkage of tumors after three immunizations were observed for both groups.

BALB/c mice (n=3) were injected intravenously with Luciferase-RNA (20 µg) complexed with different amounts of F5 liposomes to yield F5:RNA ratios of 4.8:1, 2.4:1, 1.2:1, 1.2:2, 1.2:4. Luciferase activities in vivo and ex vivo were assessed via in vivo imaging 6 hours after lipoplex injection and representative mice and organ sets are shown in FIG. 26. FIG. 27 shows the distribution of total luciferase signal among organs derived from the experiment depicted in FIG. 26.

F5 (DOTMA:Chol) goes to lungs at the ratio of F5:RNA of 4.8:1, to primarily lungs but also to spleen at the ratio of F5:RNA (2.4:1), to primarily spleen but also to lungs at the ratio of F5:RNA (1.2:1) and to exclusively to spleen at ratios of F5:RNA (1.2:2, 1.2:4). Neutral and anionic lipoplexes target more specifically to spleen whereas cationic lipoplexes primarily target lung (wrt to protein expression). No expression in liver was detected.

Example 12: Clinical Formulation of Lipoplexes

The formulation following the previously established protocol consists of two steps, namely the preformulation of a given RNA by using isotonic sodium chloride solution as diluent and the lipoplex formation by adding a defined amount of liposomes. For preformulation, first 4 ml sodium chloride (0.9% w/w in water) solution will be taken out of the NaCl vial by a syringe and added to the RNA. Then, 400 µL of liposomes (2.8 mg/mL total lipid in water) will be taken out of the liposome vial and injected using a cannula (inner diameter of 0.9 mm) into the solution of RNA and sodium chloride. The obtained RNA lipoplex formulation (5.5 ml) can be administered either, by direct parenteral injection of the desired dose as well as after preparation of an intravenous infusion. To this end, from the RNA lipoplex formulation, 5.0 mL will be taken and diluted to an infusion bag containing 50 ml of isotonic sodium chloride solution. By this protocol, lipoplex formulations with particle sizes of about 300 to 500 nm are obtained in a robust and reproducible manner; see FIG. 28.

Materials and components which may be used are as follows:

Components:
RNA: 0.5 mg/ml in 10 mM HEPES and 0.1 mM EDTA
Diluent: 0.9% NaCl
Liposomes: 2.68 mM DOTMA, 1.34 mM DOPE, particle size ($Z_{ave}$) 300-500 nm Syringes:
5 mL syringes: (e.g. Omnifix, 5 mL, Luer Lock, B. Braun Melsungen AG (Melsungen, Germany)
1 mL syringe: Injekt-F Tuberculin, 1 mL, Luer Lock, B. Braun Melsungen AG (Melsungen, Germany)

Needles:
0.9×44 mm, 20 G 1½", BD Microlance 3, Becton Dickinson S.A. (Fraga, Spain)

The sizes of the RNA lipoplex particles produced according to the above procedure range from 300 nm to 500; see FIG. 29.

Example 13: Effect of Particle Size

It is demonstrated, that the activity of the lipoplexes increases with increasing size. The size of the liposomes used for formation of lipoplexes affects also the size of the lipoplexes. Larger liposomes lead also to larger lipoplexes.

The particle characteristics of RNA lipoplexes reconstituted using F4 (DOTMA/DOPE 50:50 mol/mol) and F12 (DOTMA/DOPE 66.7:33.3 mol/mol) were investigated realizing different sizes of precursor. For that, particle sizing of lipoplexes with extruded liposomes and non-extruded, 0.45 μm filtered liposomes was performed.

TABLE 1

Sizes of liposomes used for lipoplex formation

| Formulation | Size extruded | Size not extruded |
|---|---|---|
| F4 | 164 nm | 582 nm |
| F12 | 163 nm | 637 nm |

Results for the lipoplexes are shown in FIG. 30. It is demonstrated that lipoplexes of different sizes can be produced by using precursors of different sizes.

The results from FIGS. 31 and 32 indicate that the bigger the liposomes the bigger the formed lipoplexes in these experiment the higher the observed luciferase signal.

Example 14: Sodium Chloride Buffer

Several experiments have shown that addition of PBS buffer to the RNA prior to addition of liposomes, leads to an increase of the activity of the lipoplexes. Here it is demonstrated, that instead of PBS, normal saline solution (0.9% eg. 150 mM NaCl) can be used for RNA condensation. Such NaCl solution is available as approved medicinal drug product, which facilitates logistics and handling for the lipoplex-IMP. It is further demonstrated, that also concentrated solutions of NaCl and PBS can be used for RNA condensing, resulting in equivalent activity of the later formed lipoplexes. Furthermore detailed size measurements are shown, where differently concentrated NaCl solutions were added to RNA prior to lipoplex formation. In general, lipoplex size increases with decreasing concentration of the added NaCl solution; see FIG. 35. As increasing size is correlated to increasing activity (see Example 13), addition of the normal saline, and not the concentrated saline is considered to yield higher activity.

To test the influence of pre-formulation of RNA using common buffers prior to the assembling, the particle size of lipoplexes at a charge ratio 1:2 were determined after treatment of the RNA with different concentrated PBS buffers or sodium chloride solutions; see FIGS. 33 and 34.

The prior mixing protocol, where both liposomes and RNA are treated in PBS (1x PBS final conc.) and then mixed at equal volumes, can be replaced by a simpler mixing with normal sodium chloride solution (0.9%), which is commercially available as an approved medicinal drug product. As mixing protocol for the lipoplex-IMP, RNA is preformulated with isotonic saline solution and then mixed with the liposomes in water.

The results suggest that the monovalent ion can be added at different concentrations in order to obtain the same final ionic strength in the lypoplex formulation without significantly affecting the lipoplex properties.

Example 15: Liposome/RNA Charge Ratio

The charge ratio (ratio cationic lipid to nucleotide) of 1.3 to 2 is suitable regarding the physicochemical characteristics and the biological activity. At this ratio, a higher fraction of RNA is assumed to be included in the lipoplexes as for the ratio 1:2.

The colloidal stability, the particle characteristics and the Luciferase activity of lipoplexes of non-extruded liposomes were further investigated. Lipoplexes were assembled in isotonic saline solution with liposome/RNA charge ratios between 1:2 and 1.9:2, see FIGS. 36 and 37. For lipoplexes, at a charge ratio of 1.7:2 the particle sizes significantly increased over time. In accordance with lipoplexes of extruded liposomes, lipoplexes with a charge ratio between 1:2 and 1.6:2 are invariant to minor changes in excess RNA and show particle sizes in the 350 to 480 nm range with PI values of less than 0.3.

As demonstrated in FIG. 38, liposome/RNA charge ratios between 1.1:2 and 1.6:2 result in good activity in the spleen.

All ratios deliver RNA exclusively to spleen without significant changes in performance between the different lipid/RNA ratio.

We claim:

1. A pharmaceutical composition comprising nanoparticles that comprise:
   (i) at least one cationic lipid, and
   (ii) at least one RNA molecule encoding at least one antigen,
   wherein, at physiological pH, an overall charge ratio of positive charges to negative charges of the nanoparticles is between 1:1.2 (0.83) and 1:2 (0.5), wherein the positive charges are contributed by the at least one cationic lipid, and the negative charges are contributed by the at least one RNA molecule;
   a polydispersity index of the nanoparticles is 0.5 or less as measured by dynamic light scattering; and
   the nanoparticles have an average diameter in the range of from about 250 nm to about 700 nm as measured by dynamic light scattering.

2. The pharmaceutical composition of claim 1, wherein at physiological pH the overall charge ratio of positive charges to negative charges of the nanoparticles is between 1.6:2 (0.8) and 1:2 (0.5).

3. The pharmaceutical composition of claim 1, wherein at physiological pH the overall charge ratio of positive charges to negative charges of the nanoparticles is between 1.6:2 (0.8) and 1.1:2 (0.55).

4. The pharmaceutical composition of claim 1, wherein at physiological pH the overall charge ratio of positive charges to negative charges of the nanoparticles is 1.3:2 (0.65).

5. The pharmaceutical composition of claim 1, wherein the polydispersity index of the nanoparticles is 0.4 or less as measured by dynamic light scattering.

6. The pharmaceutical composition of claim 1, wherein the polydispersity index of the nanoparticles is 0.3 or less as measured by dynamic light scattering.

7. The pharmaceutical composition of claim 1, wherein the nanoparticles have a zeta potential of from 0 mV to −50 mV.

8. The pharmaceutical composition of claim 1, wherein the nanoparticles have a zeta potential of from −10 mV to −30 mV.

9. The pharmaceutical composition of claim 1, wherein the nanoparticles have an average diameter in the range of from about 250 nm to about 550 nm as measured by dynamic light scattering.

10. The pharmaceutical composition of claim 1, wherein the at least one cationic lipid comprises 1,2-di-O-octadecenyl-3-trimethylammonium propane (DOTMA) and/or 1,2-dioleoyl-3-trimethylammonium-propane (DOTAP).

11. The pharmaceutical composition of claim 1, wherein the at least one cationic lipid comprises DOTMA.

12. The pharmaceutical composition of claim 1, wherein the at least one cationic lipid forms a complex with and/or encapsulates the at least one RNA molecule.

13. The pharmaceutical composition of claim 1, wherein the at least one cationic lipid is comprised in a vesicle encapsulating the at least one RNA molecule.

14. The pharmaceutical composition of claim 1, wherein the nanoparticles further comprise at least one helper lipid.

15. The pharmaceutical composition of claim 14, wherein the at least one helper lipid is a neutral lipid.

16. The pharmaceutical composition of claim 14, wherein the at least one helper lipid comprises 1,2-di-(9Z-octadecenoyl)-sn-glycero-3-phosphoethanolamine (DOPE), cholesterol (Chol) and/or 1,2-diolcoyl-sn-glycero-3-phosphocholine (DOPC).

17. The pharmaceutical composition of claim 14, wherein the at least one helper lipid comprises DOPE.

18. The pharmaceutical composition of claim 14, wherein a molar ratio of the at least one cationic lipid to the at least one helper lipid is from 9:1 to 3:7.

19. The pharmaceutical composition of claim 18, wherein the molar ratio of the at least one cationic lipid to the at least one helper lipid is from 4:1 to 1:2, 4:1 to 2:3, 7:3 to 1:1, or 2:1 to 1:1.

20. The pharmaceutical composition of claim 18, wherein the molar ratio of the at least one cationic lipid to the at least one helper lipid is about 2:1.

21. The pharmaceutical composition of claim 14, wherein the at least one cationic lipid is DOTMA and the at least one helper lipid is DOPE.

22. The pharmaceutical composition of claim 21, wherein the molar ratio of DOTMA to DOPE is about 2:1.

23. The pharmaceutical composition of claim 14, wherein:
at physiological pH the overall charge ratio of positive charges to negative charges of the nanoparticles is between 1:1.2 (0.83) and 1:2 (0.5);
the nanoparticles have an average diameter in the range of from about 250 nm to about 550 nm as measured by dynamic light scattering; and
the molar ratio of the at least one cationic lipid to the at least one helper lipid is from 9:1 to 3:7.

24. The pharmaceutical composition of claim 23, wherein:
at physiological pH the overall charge ratio of positive charges to negative charges of the nanoparticles is 1.3:2 (0.65);
the nanoparticles have an average diameter in the range of from about 300 nm to about 500 nm as measured by dynamic light scattering; and
the at least one cationic lipid is DOTMA and the at least one helper lipid is DOPE, and the molar ratio of DOTMA to DOPE is about 2:1.

25. The pharmaceutical composition of claim 1, wherein the nanoparticles are lipoplexes comprising DOTMA and DOPE in a molar ratio of 8:2 to 3:7, and wherein the charge ratio of positive charges in DOTMA to negative charges in the at least one RNA molecule is 1.6:2 (0.8) to 1:2 (0.5).

26. The pharmaceutical composition of claim 25, wherein the lipoplexes comprise DOTMA and DOPE in a molar ratio of 7:3 to 5:5 and wherein the charge ratio of positive charges in DOTMA to negative charges in the at least one RNA molecule is about 1.3:2 (0.65).

27. The pharmaceutical composition of claim 1, wherein the nanoparticles are lipoplexes comprising DOTMA and Cholesterol in a molar ratio of 8:2 to 3:7, and wherein the charge ratio of positive charges in DOTMA to negative charges in the at least one RNA molecule is 1.6:2 (0.8) to 1:2 (0.5).

28. The pharmaceutical composition of claim 27, wherein the lipoplexes comprise DOTMA and Cholesterol in a molar ratio of 7:3 to 5:5 and wherein the charge ratio of positive charges in DOTMA to negative charges in the at least one RNA molecule is about 1.3:2 (0.65).

29. The pharmaceutical composition of claim 1, wherein the nanoparticles are lipoplexes comprising DOTAP and DOPE in a molar ratio of 8:2 to 3:7, and wherein the charge ratio of positive charges in DOTAP to negative charges in the at least one RNA molecule is 1.6:2 (0.8) to 1:2 (0.5).

30. The pharmaceutical composition of claim 29, wherein the lipoplexes comprise DOTAP and DOPE in a molar ratio of 7:3 to 5:5 and wherein the charge ratio of positive charges in DOTAP to negative charges in the at least one RNA molecule is about 1.3:2 (0.65).

31. The pharmaceutical composition of claim 1, wherein the nanoparticles are produced by a process comprising a step of incubating the at least one RNA molecule with bivalent cations prior to incorporation into said nanoparticles and/or by incubating the at least one RNA molecule with monovalent ions prior to incorporation into said nanoparticles and/or by incubating the at least one RNA molecule with one or more buffers prior to incorporation into said nanoparticles.

32. The pharmaceutical composition of claim 1, wherein the at least one antigen is a disease-associated antigen or elicits an immune response against a disease-associated antigen or cells expressing a disease-associated antigen.

33. The pharmaceutical composition of claim 1, wherein the at least one antigen is a tumor antigen or an antigen from an infectious agent.

34. The pharmaceutical composition of claim 1, wherein the at least one RNA molecule is or comprises mRNA.

35. The pharmaceutical composition of claim 1, wherein the at least one RNA molecule encoding at least one antigen comprises an unmasked poly-A sequence.

36. The pharmaceutical composition of claim 35, wherein the unmasked poly-A sequence has a length of about 120 nucleotides.

37. The pharmaceutical composition of claim 1, wherein the at least one RNA molecule encoding at least one antigen comprises a 3'UTR.

38. The pharmaceutical composition of claim 1, wherein the at least one RNA molecule encoding at least one antigen further comprises a 5'-cap.

39. The pharmaceutical composition of claim 38, wherein the 5' cap comprises:

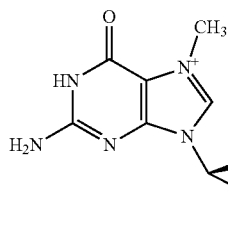 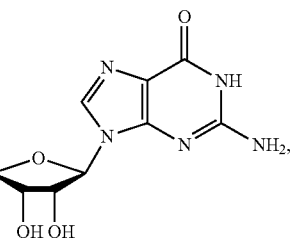

wherein:
$R_1$ and $R_2$ are each independently hydroxyl or methoxy; and
W, X, and Y are each independently selected form the group consisting of oxygen, sulfur, selenium and $BH_3$.

40. The pharmaceutical composition of claim 39, wherein:
(a) $R_1$ and $R_2$ are OH, and W, X, and Y are oxygen;
(b) one of $R_1$ and $R_2$ is OH, the other $R_1$ and $R_2$ is methoxy, and W, X, and Y are oxygen;
(c) $R_1$ and $R_2$ are OH, X is sulfur, and W and Y are oxygen; or
(d) $R_2$ is OH, $R_1$ is methoxy, one of W, X, and Y is sulfur, and the other two of W, X, and Y are oxygen.

41. The pharmaceutical composition of claim 39, wherein $R_2$ is OH, $R_1$ is methoxy, X is sulfur, and W and Y are oxygen.

42. The pharmaceutical composition of claim 1, wherein the pharmaceutical composition further comprises one or more pharmaceutically acceptable carriers, diluents, excipients, and/or adjuvants.

43. A method of treating or preventing a disease involving an antigen in a subject comprising administering to the subject the pharmaceutical composition of claim 1, wherein the antigen is a disease-associated antigen or elicits an immune response against a disease-associated antigen or cells expressing a disease-associated antigen, whereby the disease in the subject is treated or the subject is prevented from developing the disease.

44. A pharmaceutical composition comprising nanoparticles that comprise:
(i) at least one cationic lipid,
(ii) at least one RNA molecule encoding at least one antigen, and
(iii) at least one helper lipid,
wherein, at physiological pH, an overall charge ratio of positive charges to negative charges of the nanoparticles is 1.3:2 (0.65), wherein the positive charges are contributed by the at least one cationic lipid, and the negative charges are contributed by the at least one RNA molecule;
a polydispersity index of the nanoparticles is 0.5 or less as measured by dynamic light scattering;
the nanoparticles have an average diameter in the range of from about 250 nm to about 700 nm as measured by dynamic light scattering;
the at least one cationic lipid is DOTMA;
the at least one helper lipid is DOPE; and
a molar ratio of DOTMA to DOPE is about 2:1.

* * * * *